(12) United States Patent
Mogensen et al.

(10) Patent No.: US 7,202,213 B2
(45) Date of Patent: Apr. 10, 2007

(54) COMBINATION THERAPY USING A DUAL PPAR-α/PPAR-γ ACTIVATOR AND A GLP-1 DERIVATIVE FOR THE TREATMENT OF METABOLIC SYNDROME AND RELATED DISEASES AND DISORDERS

(75) Inventors: John Patrick Mogensen, Herlev (DK); Per Sauerberg, Farum (DK); Paul Stanley Bury, Kobenhavn (DK); Lone Jeppesen, Virum (DK); Ingrid Pettersson, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 721 days.

(21) Appl. No.: 10/442,284

(22) Filed: May 20, 2003

(65) Prior Publication Data

US 2003/0199451 A1 Oct. 23, 2003

Related U.S. Application Data

(63) Continuation of application No. 09/771,217, filed on Jan. 26, 2001, now Pat. No. 6,569,901.

(60) Provisional application No. 60/245,370, filed on Nov. 2, 2000, provisional application No. 60/217,903, filed on Jul. 13, 2000, provisional application No. 60/181,056, filed on Feb. 8, 2000.

(30) Foreign Application Priority Data

| Jan. 28, 2000 | (DK) | ............................. 2000 00137 |
| Jul. 7, 2000 | (DK) | ............................. 2000 01065 |
| Oct. 25, 2000 | (DK) | ............................. 2000 01593 |

(51) Int. Cl.
*A61K 38/00* (2006.01)

(52) U.S. Cl. ....................................................... 514/12

(58) Field of Classification Search ................... None
See application file for complete search history.

(56) References Cited

U.S. PATENT DOCUMENTS

| 6,150,413 A | 11/2000 | Bernardon et al. | .......... 514/568 |
| 6,191,102 B1 * | 2/2001 | DiMarchi et al. | ............... 514/2 |
| 6,214,820 B1 | 4/2001 | Jeppesen et al. | ........ 514/211.11 |

FOREIGN PATENT DOCUMENTS

| EP | 0551035 A1 | 7/1993 |
| EP | 0879814 A1 | 11/1998 |
| EP | 0903343 A1 | 3/1999 |
| WO | WO 94/01420 | 1/1994 |
| WO | WO 95/03313 | 2/1995 |
| WO | WO 96/04260 | 2/1996 |
| WO | WO 96/04261 | 2/1996 |
| WO | WO 97/25042 | 7/1997 |
| WO | WO 97/36579 | 10/1997 |
| WO | WO 99/08501 | 2/1999 |
| WO | WO 99/16758 | 4/1999 |
| WO | WO 99/19313 | 4/1999 |
| WO | WO 99/20614 | 4/1999 |
| WO | WO 99/38850 | 8/1999 |
| WO | WO 99/43705 A1 * | 10/1999 |

* cited by examiner

*Primary Examiner*—Paul A. Zucker
(74) *Attorney, Agent, or Firm*—Rosemarie R. Wilk-Orescar; Marc A. Began; Reza Green

(57) ABSTRACT

The present invention relates to a pharmaceutical composition comprising a dual Peroxisome Proliferator-Activated Receptor-alpha/Peroxisome Proliferator-Activated Receptor-gama activator (PPAR-α/PPAR-γ) and a Glucagon Like Peptide-1 (GLP-1) derivative for treating, preventing and reducing the risk of developing Type 2 diabetes, insulin resistance, dyslipidemia, obesity, hypertension and other related diseases and disorders.

62 Claims, No Drawings

COMBINATION THERAPY USING A DUAL PPAR-α/PPAR-γ ACTIVATOR AND A GLP-1 DERIVATIVE FOR THE TREATMENT OF METABOLIC SYNDROME AND RELATED DISEASES AND DISORDERS

CROSS REFERENCE TO RELATED APPLICATIONS

This application is a continuation of Ser. No. 09/771,217, filed Jan. 26, 2001, now U.S. Pat. No. 6,569,901, which claims benefit of 60/181,056, filed Feb. 8, 2000, 60/217,903, filed Jul. 13, 2000 and 60/245,370, filed Nov. 2, 2000.

FIELD OF THE INVENTION

The present invention relates to a pharmaceutical composition comprising a dual Peroxisome Proliferator-Activated Receptor-alpha/Peroxisome Proliferator-Activated Receptor-gama activator (PPAR-α/PPAR-γ) and a Glucagon Like Peptide-1 (GLP-1) derivative for treating, preventing and reducing the risk of developing Type 2 diabetes, insulin resistance, dyslipidemia, obesity, hypertension and other related diseases and disorders.

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. WO91/19702, WO 95/03038, WO 96/04260, WO 94/13650, WO 94/01420, WO 97/36579, WO 97/25042, WO 95/17394, WO 99/08501, WO 99/19313 and WO 99/16758).

Peptides are widely used in medical practice, and since they can be produced by recombinant DNA technology it can be expected that their importance will increase also in the years to come. When native peptides or analogues thereof are used in therapy it is generally found that they have a high clearance. A high clearance of a therapeutic agent is inconvenient in cases where it is desired to maintain a high blood level thereof over a prolonged period of time since repeated administrations will then be necessary. Examples of peptides which have a high clearance are: ACTH, corticotropin-releasing factor, angiotensin, calcitonin, insulin, glucagon, glucagon-like peptide-1, glucagon-like peptide-2, insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opiods and analogues thereof, superoxide dismutase, interferon, asparaginase, arginase, arginine deaminase, adenosine deaminase and ribonuclease. In some cases it is possible to influence the release profile of peptides by applying suitable pharmaceutical compositions, but this approach has various shortcomings and is not generally applicable.

The hormones regulating insulin secretion belong to the so-called enteroinsular axis, designating a group of hormones, released from the gastrointestinal mucosa in response to the presence and absorption of nutrients in the gut, which promote an early and potentiated release of insulin. The enhancing effect on insulin secretion, the so-called incretin effect, is probably essential for a normal glucose tolerance. Many of the gastrointestinal hormones, including gastrin and secretin (cholecystokinin is not insulinotropic in man), are insulinotropic, but the only physiologically important ones, those that are responsible for the incretin effect, are the glucose-dependent insulinotropic polypeptide, GIP, and glucagon-like peptide-1 (GLP-1). Because of its insulinotropic effect, GIP, isolated in 1973 (1) immediately attracted considerable interest among diabetologists. However, numerous investigations carried out during the following years clearly indicated that a defective secretion of GIP was not involved in the pathogenesis of insulin dependent diabetes mellitus (IDDM) or non insulin-dependent diabetes mellitus (NIDDM) (2). Furthermore, as an insulinotropic hormone, GIP was found to be almost ineffective in NIDDM (2). The other incretin hormone, GLP-1 is the most potent insulinotropic substance known (3). Unlike GIP, it is surprisingly effective in stimulating insulin secretion in NIDDM patients. In addition, and in contrast to the other insulinotropic hormones (perhaps with the exception of secretin) it also potently inhibits glucagon secretion. Because of these actions it has pronounced blood glucose lowering effects particularly in patients with NIDDM.

GLP-1, a product of the proglucagon (4), is one of the youngest members of the secretin-VIP family of peptides, but is already established as an important gut hormone with regulatory function in glucose metabolism and gastrointestinal secretion and metabolism (5). The glucagon gene is processed differently in the pancreas and in the intestine. In the pancreas (9), the processing leads to the formation and parallel secretion of 1) glucagon itself, occupying positions 33-61 of proglucagon (PG); 2) an N-terminal peptide of 30 amino acids (PG (1-30)) often called glicentin-related pancreatic peptide, GRPP (10, 11); 3) a hexapeptide corresponding to PG (64-69); 4) and, finally, the so-called major proglucagon fragment (PG (72-158)), in which the two glucagon-like sequences are buried (9). Glucagon seems to be the only biologically active product. In contrast, in the intestinal mucosa, it is glucagon that is buried in a larger molecule, while the two glucagon-like peptides are formed separately (8). The following products are formed and secreted in parallel: 1) glicentin, corresponding to PG (1-69), with the glucagon sequence occupying residues Nos. 33-61 (12); 2) GLP-1(7-36)amide (PG (78-107))amide (13), not as originally believed PG (72-107)amide or 108, which is inactive). Small amounts of C-terminally glycine-extended but equally bioactive GLP-1(7-37), (PG (78-108)) are also formed (14); 3) intervening peptide-2 (PG (111-122)amide) (15); and 4) GLP-2 (PG (126-158)) (15, 16). A fraction of glicentin is cleaved further into GRPP (PG (1-30)) and oxyntomodulin (PG (33-69)) (17, 18). Of these peptides, GLP-1, has the most conspicuous biological activities.

Being secreted in parallel with glicentin/enteroglucagon, it follows that the many studies of enteroglucagon secretion (6, 7) to some extent also apply to GLP-1 secretion, but GLP-1 is metabolised more quickly with a plasma half-life in humans of 2 min (19). Carbohydrate or fat-rich meals stimulate secretion (20), presumably as a result of direct interaction of yet unabsorbed nutrients with the microvilli of the open-type L-cells of the gut mucosa. Endocrine or neural mechanisms promoting GLP-1 secretion may exist but have not yet been demonstrated in humans.

The incretin function of GLP-1(29-31) has been clearly illustrated in experiments with the GLP-1 receptor antagonist, exendin 9-39, which dramatically reduces the incretin effect elicited by oral glucose in rats (21, 22). The hormone interacts directly with the β-cells via the GLP-1 receptor (23) which belongs to the glucagon/VIP/calcitonin family of G-protein-coupled 7-transmembrane spanning receptors. The importance of the GLP-1 receptor in regulating insulin secretion was illustrated in recent experiments in which a targeted disruption of the GLP-1 receptor gene was carried out in mice. Animals homozygous for the disruption had greatly deteriorated glucose tolerance and fasting hyperglycaemia, and even heterozygous animals were glucose intolerant (24). The signal transduction mechanism (25) primarily involves activation of adenylate cyclase, but elevations of intracellular $Ca^{2+}$ are also essential (25, 26). The action of the hormone is best described as a potentiation of glucose stimulated insulin release (25), but the mechanism that couples glucose and GLP-1 stimulation is not known. It may involve a calcium-induced calcium release (26, 27). As already mentioned, the insulinotropic action of GLP-1 is preserved in diabetic β-cells. The relation of the latter to its ability to convey "glucose competence" to isolated insulin-secreting cells (26, 28), which respond poorly to glucose or GLP-1 alone, but fully to a combination of the two, is also not known. Equally importantly, however, the hormone also potently inhibits glucagon secretion (29). The mechanism is not known, but seems to be paracrine, via neighbouring insulin or somatostatin cells (25). Also the glucagonostatic action is glucose-dependent, so that the inhibitory effect decreases as blood glucose decreases. Because of this dual effect, if the plasma GLP-1 concentrations increase either by increased secretion or by exogenous infusion the molar ratio of insulin to glucagon in the blood that reaches the liver via the portal circulation is greatly increased, whereby hepatic glucose production decreases (30). As a result blood glucose concentrations decrease. Because of the glucose dependency of the insulinotropic and glucagonostatic actions, the glucose lowering effect is self-limiting, and the hormone, therefore, does not cause hypoglycaemia regardless of dose (31). The effects are preserved in patients with diabetes mellitus (32), in whom infusions of slightly supraphysiological doses of GLP-1 may completely normalise blood glucose values in spite of poor metabolic control and secondary failure to sulphonylurea (33). The importance of the glucagonostatic effect is illustrated by the finding that GLP-1 also lowers blood glucose in type-1 diabetic patients without residual β-cell secretory capacity (34).

In addition to its effects on the pancreatic islets, GLP-1 has powerful actions on the gastrointestinal tract. Infused in physiological amounts, GLP-1 potently inhibits pentagastrin-induced as well as meal-induced gastric acid secretion (35, 36). It also inhibits gastric emptying rate and pancreatic enzyme secretion (36). Similar inhibitory effects on gastric and pancreatic secretion and motility may be elicited in humans upon perfusion of the ileum with carbohydrate- or lipid-containing solutions (37, 38). Concomitantly, GLP-1 secretion is greatly stimulated, and it has been speculated that GLP-1 may be at least partly responsible for this so-called "ileal-brake" effect (38). In fact, recent studies suggest that, physiologically, the ileal-brake effects of GLP-1 may be more important than its effects on the pancreatic islets. Thus, in dose response studies GLP-1 influences gastric emptying rate at infusion rates at least as low as those required to influence islet secretion (39).

GLP-1 seems to have an effect on food intake. Intraventricular administration of GLP-1 profoundly inhibits food intake in rats (40, 42). This effect seems to be highly specific. Thus, N-terminally extended GLP-1(PG 72-107) amide is inactive and appropriate doses of the GLP-1 antagonist, exendin 9-39, abolish the effects of GLP-1(41). Acute, peripheral administration of GLP-1 does not inhibit food intake acutely in rats (41, 42). However, it remains possible that GLP-1 secreted from the intestinal L-cells may also act as a satiety signal.

Not only the insulinotropic effects but also the effects of GLP-1 on the gastrointestinal tract are preserved in diabetic patients (43), and may help curtailing meal-induced glucose excursions, but, more importantly, may also influence food intake. Administered intravenously, continuously for one week, GLP-1 at 4 ng/kg/min has been demonstrated to dramatically improve glycaemic control in NIDDM patients without significant side effects (44). The peptide is fully active after subcutaneous administration (45), but is rapidly degraded mainly due to degradation by dipeptidyl peptidase IV-like enzymes (46, 47).

The amino acid sequence of GLP-1 is given i.a. by Schmidt et al. (*Diabetologia* 28 704–707 (1985). Although the interesting pharmacological properties of GLP-1(7-37) and analogues thereof have attracted much attention in recent years only little is known about the structure of these molecules. The secondary structure of GLP-1 in micelles has been described by Thorton et al. (*Biochemistry* 33 3532-3539 (1994)), but in normal solution, GLP-1 is considered a very flexible molecule. Surprisingly, we found that derivatisation of this relatively small and very flexible molecule resulted in compounds whose plasma profile were highly protracted and still had retained activity.

GLP-1 and analogues of GLP-1 and fragments thereof are potentially useful i.a. in the treatment of type 1 and type 2 diabetes. However, the high clearance limits the usefulness of these compounds, and thus there still is a need for improvements in this field.

SUMMARY OF THE INVENTION

Accordingly, it is one object of the present invention to provide a pharmaceutical composition comprising a dual Peroxisome Proliferator-Activated Receptor-alpha/Peroxisome Proliferator-Activated Receptor-gama activator (PPAR-α/PPAR-γ) and a Glucagon Like Peptide-1 (GLP-1) derivative.

The invention further provides a method useful for treating, preventing and reducing the risk of developing Type 2 diabetes, metabolic syndrome, insulin resistance, dyslipidemia, obesity, hypertension and other related diseases and disorders comprising administering to a mammal in need of such treatment an effective amount of a combination, or pharmaceutical composition comprising such combination, of a dual PPAR-α/PPAR-γ activator and a GLP-1 derivative.

The invention further provides a kit comprising a dual PPAR-α/PPAR-γ activator and a pharmaceutically acceptable carrier, vehicle, or diluent in a first unit dosage form; an amount of a GLP-1 derivative and a pharmaceutically acceptable carrier, vehicle, or diluent in a second unit dosage form; and a container.

DETAILED DESCRIPTION OF THE INVENTION

Accordingly, an object of the present invention provides a pharmaceutical composition comprising a glucagon like peptide-1 (GLP-1) derivative and a dual Peroxisome Proliferator-Activated Receptor-a/Peroxisome Proliferator-Activated Receptor-γ (PPAR-α/PPAR-γ) activator.

Another object of the present invention provides a combination therapy pharmaceutical composition wherein the dual PPAR-α/PPAR-γ activator is a compound of formula (I)

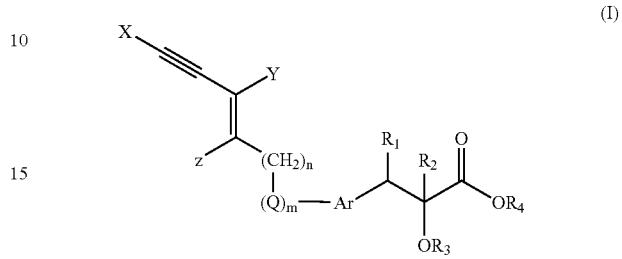

(I)

wherein X is hydrogen or
X is $C_{1-2}$-alkyl, $C_{2-12}$-alkenyl, $C_{2-12}$-alkynyl, aryl, heteroaryl, aralkyl, heteroaralkyl or heterocyclyl each of which is optionally substituted with one or more substituents selected from halogen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryloxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and Y is hydrogen or
Y is $C_{1-12}$-alkyl, $C_{2-12}$-alkenyl, $C_{2-12}$-alkynyl, $C_{4-12}$-alkenynyl, aryl, heteroaryl, aralkyl or heteroaralkyl each of which is optionally substituted with one or more substituents selected from halogen, $C_{1-6}$-alkyl, perhalomethyl, hydroxy, aryl, heteroaryl, amino, carboxy or $C_{1-6}$-alkylester; and Z is hydrogen, halogen, hydroxy or
Z is $C_{1-6}$-alkyl or $C_{1-6}$-alkoxy each of which is optionally substituted with one or more substituents selected from $C_{1-6}$-alkoxy, halogen, hydroxy, carboxy, amino or cyano; and Q is O, S or $NR_5$, wherein $R_5$ is hydrogen, $C_{1-6}$-alkyl, $C_{2-6}$-alkenyl, $C_{2-6}$-alkynyl, $C_{4-6}$-alkenynyl, aralkyl or heteroaralkyl and wherein $R_5$ is optionally substituted with one or more substituents selected from halogen, hydroxy, $C_{1-6}$-alkoxy, amino or carboxy; and Ar is arylene, heteroarylene or a divalent heterocyclic group each of which can be optionally substituted with one or more substituents selected from $C_{1-6}$-alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy, cyano, carboxy or $C_{1-6}$alkylester; and $R_4$ is hydrogen, $C_{1-6}$-alkyl, $C_{2-6}$-alkenyl, $C_{2-6}$-alkynyl, $C_{4-6}$-alkenynyl or aryl;

n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers, racemic mixture, or polymorphs.

Another object of the present invention provides a combination therapy pharmaceutical composition of formula (I) wherein X is aryl, heteroaryl or heterocyclyl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

Another object of the present invention provides a combination therapy pharmaceutical composition of formula (I) wherein X is aryl, heteroaryl or heterocyclyl each of which is optionally substituted with one or more substituents selected from halogen, perhalomethyl, $C_{1-6}$alkoxy, $C_{1-6}$-alkylthio, aryl, aryloxy, arylthio, aralkyl, aralkoxy, heteroaryl, heteroaralkyl, heteroaryloxy or heteroaralkoxy.

Another object of the present invention provides a combination therapy pharmaceutical composition of formula (I) wherein X is aryl optionally substituted with one or more substituents selected from halogen, perhalomethyl, $C_{1-6}$alkoxy, $C_{1-6}$alkylthio, aryl, aryloxy, arylthio, aralkyl, aralkoxy, heteroaryl, heteroaralkyl, heteroaryloxy or heteroaralkoxy.

Another object of the present invention provides a combination therapy pharmaceutical composition of formula (I) wherein X is phenyl or naphthyl each of which is optionally substituted with one or more substituents selected from halogen or perhalomethyl.

Another object of the present invention provides a combination therapy pharmaceutical composition of formula (I) wherein X is phenyl optionally substituted with one or more substituents selected from halogen.

Another object of the present invention provides a combination therapy pharmaceutical composition of formula (I) wherein X is phenyl.

Another object of the present invention provides a combination therapy pharmaceutical composition of formula (I) wherein X is heteroaryl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

Another object of the present invention provides a combination therapy pharmaceutical composition of formula (I) wherein X is heterocyclyl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

Another object of the present invention provides a combination therapy pharmaceutical composition of formula (I) wherein Y is hydrogen, $C_{1-12}$-alkyl or aryl.

Another object of the present invention provides a combination therapy pharmaceutical composition of formula (I) wherein Y is hydrogen or methyl.

Another object of the present invention provides a combination therapy pharmaceutical composition of formula (I) wherein Y is hydrogen.

Another object of the present invention provides a combination therapy pharmaceutical composition of formula (I) wherein Z is hydrogen or $C_{1-6}$-alkoxy.

Another object of the present invention provides a combination therapy pharmaceutical composition of formula (I) wherein Z is hydrogen.

Another object of the present invention provides a combination therapy pharmaceutical composition of formula (I) wherein Q is O.

Another object of the present invention provides a combination therapy pharmaceutical composition of formula (I) wherein Ar is arylene optionally substituted with one or more substituents selected from $C_{1-6}$-alkyl or $C_{1-6}$-alkoxy each of which can be optionally substituted with carboxy.

Another object of the present invention provides a combination therapy pharmaceutical composition of formula (I) wherein Ar is phenylene.

Another object of the present invention provides a combination therapy pharmaceutical composition of formula (I) wherein $R_1$ is hydrogen or $R_1$ forms a bond together with $R_2$.

Another object of the present invention provides a combination therapy pharmaceutical composition of formula (I) wherein $R_1$ is hydrogen.

Another object of the present invention provides a combination therapy pharmaceutical composition of formula (I) wherein $R_2$ is hydrogen or $R_2$ forms a bond together with $R_1$.

Another object of the present invention provides a combination therapy pharmaceutical composition of formula (I) wherein $R_2$ is hydrogen.

Another object of the present invention provides a combination therapy pharmaceutical composition of formula (I) wherein $R_3$ is $C_{1-6}$-alkyl.

Another object of the present invention provides a combination therapy pharmaceutical composition of formula (I) wherein $R_3$ is $C_{1-2}$-alkyl.

Another object of the present invention provides a combination therapy pharmaceutical composition of formula (I) wherein $R_4$ is hydrogen.

Another object of the present invention provides a combination therapy pharmaceutical composition of formula (I) wherein n is 1.

Another object of the present invention provides a combination therapy pharmaceutical composition of formula (I) wherein m is 1.

Another object of the present invention provides a combination therapy pharmaceutical composition of formula (I) wherein alkyl is methyl or ethyl.

Another object of the present invention provides a combination therapy pharmaceutical composition of formula (I) wherein alkenyl is vinyl or 1-propenyl.

Another object of the present invention provides a combination therapy pharmaceutical composition of formula (I) wherein alkynyl is 1-propynyl.

Another object of the present invention provides a combination therapy pharmaceutical composition of formula (I) 2 wherein alkenynyl is 1-pentene-4-yne.

Another object of the present invention provides a combination therapy pharmaceutical composition of formula (I) wherein alkoxy is methoxy, ethoxy, isopropoxy or cyclopropoxy.

Another object of the present invention provides a combination therapy pharmaceutical composition of formula (I) wherein aryl is phenyl or naphthyl optionally substituted with halogen.

Another object of the present invention provides a combination therapy pharmaceutical composition of formula (I) wherein arylene is phenylene.

Another object of the present invention provides a combination therapy pharmaceutical composition of formula (I) wherein halogen is chlorine.

Another object of the present invention provides a combination therapy pharmaceutical composition of formula (I) wherein perhalomethyl is trifluoromethyl.

Another object of the present invention provides a combination therapy pharmaceutical composition of formula (I) wherein heteroaryl is furan, pyrrole, pyridine, indole or benzofuran.

Another object of the present invention provides a combination therapy pharmaceutical composition of formula (I) wherein heteroarylene is furan, pyrrole, pyridine, indole or benzofuran.

Another object of the present invention provides a combination therapy pharmaceutical composition of formula (I) wherein aralkyl is benzyl.

Another object of the present invention provides a combination therapy pharmaceutical composition of formula (I) wherein aryloxy is phenoxy.

Another object of the present invention provides a combination therapy pharmaceutical composition of formula (I) wherein aralkoxy is benzyloxy.

Another object of the present invention provides a combination therapy pharmaceutical composition of formula (I) wherein n is an integer ranging from 1 to 3 and m is 1.

Another object of the present invention provides a combination therapy pharmaceutical composition of formula (I) wherein the substituents Z and Y are arranged in a trans-configuration.

Another object of the present invention provides a combination therapy pharmaceutical composition of formula (I) wherein the substituents Z and Y are arranged in a cis-configuration.

Another object of the present invention provides a combination therapy pharmaceutical composition wherein the dual PPAR-α/PPAR-γ activator of formula (I) is selected from the following:

(E)-(S)-2-Ethoxy-3-[4-(5-phenyl-pent-2-en-4-ynyloxy)-phenyl]-propionic acid ethyl ester,
(E)-(S)-2-Ethoxy-3-[4-(5-phenyl-pent-2-en-4-ynyloxy)-phenyl]-propionic acid,
(Z)-(S)-2-Ethoxy-3-[4-(3-methyl-5-phenyl-pent-2-en-4-ynyloxy)-phenyl]-propionic acid ethyl ester,
(Z)-(S)-2-Ethoxy-3-[4-(3-methyl-5-phenyl-pent-2-en-4-ynyloxy)-phenyl]-propionic acid,
(E)-(S)-2-Ethoxy-3-[4-(3-methyl-5-phenyl-pent-2-en-4-ynyloxy)-phenyl]-propionic acid ethyl ester, and
(E)-(S)-2-Ethoxy-3-[4-(3-methyl-5-phenyl-pent-2-en-4-ynyloxy)-phenyl]-propionic acid;

or a pharmaceutically acceptable salt thereof.

Another object of the present invention provides a combination therapy pharmaceutical composition wherein the dual PPAR-α/PPAR-γ activator of formula (I) is selected from the following:

Ethyl (E)-(S)-2-ethoxy-3-[4-(3-methyl-5-(3,5-dichloro-phenyl)-pent-2-en-4-ynyloxy)-phenyl]-propionate,
(E)-(S)-2-ethoxy-3-[4-(3-methyl-5-(3,5-dichloro-phenyl)-pent-2-en-4-ynyloxy)-phenyl]-propionic acid,
Ethyl (Z)-(S)-2-ethoxy-3-[4-(3-methyl-5-(3,5-dichloro-phenyl)-pent-2-en-4-ynyloxy)-phenyl]-propionate,
(Z)-(S)-2-ethoxy-3-[4-(3-methyl-5-(3,5-dichloro-phenyl)-pent-2-en-4-ynyloxy)-phenyl]-propionic acid,
Ethyl (E)-(S)-2-ethoxy-3-[4-(3-methyl-5-(3-trifluoromethyl-phenyl)-pent-2-en-4-ynyloxy)-phenyl]-propionate,
(E)-(S)-2-ethoxy-3-[4-(3-methyl-5-(3-trifluoromethyl-phenyl)-pent-2-en-4-ynyloxy)-phenyl]-propionic acid,
Ethyl (Z)-(S)-2-ethoxy-3-[4-(3-methyl-5-(3-trifluoromethyl-phenyl)-pent-2-en-4-ynyloxy)-phenyl]-propionate, and
(Z)-(S)-2-ethoxy-3-[4-(3-methyl-5-(3-trifluoromethyl-phenyl)-pent-2-en-4-ynyloxy)-phenyl]-propionic acid;

or a pharmaceutically acceptable salt thereof.

Another object of the present invention provides a combination therapy pharmaceutical composition wherein the dual PPAR-α/PPAR-γ activator of formula (I) is selected from the following:

Ethyl (E)-(S)-2-ethoxy-3-[4-(3-methyl-5-(1-naphthyl)-pent-2-en-4-ynyloxy)-phenyl]-propionate,
(E)-(S)-2-ethoxy-3-[4-(3-methyl-5-(1-naphthyl)-pent-2-en-4-ynyloxy)-phenyl]-propionic acid,
Ethyl (Z)-(S)-2-ethoxy-3-[4-(3-methyl-5-(1-naphthyl)-pent-2-en-4-ynyloxy)-phenyl]-propionate,
(Z)-(S)-2-ethoxy-3-[4-(3-methyl-5-(1-naphthyl)-pent-2-en-4-ynyloxy)-phenyl]-propionic acid,
Ethyl (E)-(S)-2-ethoxy-3-[4-(-5-(3,5-dichloro-phenyl)-pent-2-en-4-ynyloxy)-phenyl]-propionate,
(E)-(S)-2-ethoxy-3-[4-(5-(3,5-dichloro-phenyl)-pent-2-en-4-ynyloxy)-phenyl]-propionic acid,
Ethyl (Z)-(S)-2-ethoxy-3-[4-(3-methyl-5-(3,5-dichloro-phenyl)-pent-2-en-4-ynyloxy)-phenyl]-propionate, and
(Z)-(S)-2-ethoxy-3-[4-(3-methyl-5-(3,5-dichloro-phenyl)-pent-2-en-4-ynyloxy)-phenyl]-propionic acid;

or a pharmaceutically acceptable salt thereof.

Another object of the present invention provides a combination therapy pharmaceutical composition wherein the dual PPAR-α/PPAR-γ activator of formula (I) is selected from the following:

(Z)-(S)-2-Ethoxy-3-[4-(5-phenyl-pent-2-en-4-ynyloxy)-phenyl]-propionic acid ethyl ester,
(Z)-(S)-2-Ethoxy-3-[4-(5-phenyl-pent-2-en-4-ynyloxy)-phenyl]-propionic acid, and
(E)-(RS)-2-Ethoxy-3-[3-(5-phenyl-pent-2-en-4-ynyloxy)-phenyl]-propionic acid ethyl ester;

or a pharmaceutically acceptable salt thereof.

Another object of the present invention provides a combination therapy pharmaceutical composition wherein the dual PPAR-α/PPAR-γ activator of formula (I) is selected from the following:

(E)-(S)-3-{4-[5-(1,3-Difluoro-phenyl)-pent-2-en-4-ynyloxy]-phenyl}-2-ethoxy-propionic acid,
(E)-(S)-3-{4-[5-(1,3-Dibromo-phenyl)-pent-2-en-4-ynyloxy]-phenyl}-2-ethoxy-propionic acid,
(E)-(S)-3-{4-[5-(1,3-Diiodo-phenyl)-pent-2-en-4-ynyloxy]-phenyl}-2-ethoxy-propionic acid,
(E)-(S)-3-{4-[5-(1,3-Bis-trifluoromethyl-phenyl)-pent-2-en-4-ynyloxy]-phenyl}-2-ethoxy-propionic acid,
(E)-(S)-3-{4-[5-(1,3-Dimethoxy-phenyl)-pent-2-en-4-ynyloxy]-phenyl}-2-ethoxy-propionic acid,
(E)-(S)-3-{4-[5-(1,3-Diethoxy-phenyl)-pent-2-en-4-ynyloxy]-phenyl}-2-ethoxy-propionic acid,
(E)-(S)-3-{4-[5-(1,3-Bis-(2,2,2-trifluoromethoxy)-phenyl)-pent-2-en-4-ynyloxy]-phenyl}-2-ethoxy-propionic acid,
(E)-(S)-3-{4-[5-(1,3-Bis-(2,2,2-trifluoroethoxy)-phenyl)-pent-2-en-4-ynyloxy]-phenyl}-2-ethoxy-propionic acid,
(E)-(S)-3-{4-[5-(3,5-Difluoro-phenyl)-pent-2-en-4-ynyloxy]-phenyl}-2-ethoxy-propionic acid,
(E)-(S)-3-{4-[5-(3,5-Dibromo-phenyl)-pent-2-en-4-ynyloxy]-phenyl}-2-ethoxy-propionic acid,
(E)-(S)-3-{4-[5-(3,5-Diiodo-phenyl)-pent-2-en-4-ynyloxy]-phenyl}-2-ethoxy-propionic acid,
(E)-(S)-3-{4-[5-(3,5-Bis-trifluoromethyl-phenyl)-pent-2-en-4-ynyloxy]-phenyl}-2-ethoxy-propionic acid,
(E)-(S)-3-{4-[5-(3,5-Dimethoxy-phenyl)-pent-2-en-4-ynyloxy]-phenyl}-2-ethoxy-propionic acid, (E)-(S)-3-{4-[5-(3,5-Diethoxy-phenyl)-pent-2-en-4-ynyloxy]-phenyl}-2-ethoxy-propionic acid,
(E)-(S)-3-{4-[5-(3,5-Bis-(2,2,2-trifluoromethoxy)-phenyl)-pent-2-en-4-ynyloxy]-phenyl}-2-ethoxy-propionic acid,
(E)-(S)-3-{4-[5-(3,5-Bis-(2,2,2-trifluoroethoxy)-phenyl)-pent-2-en-4-ynyloxy]-phenyl}-2-ethoxy-propionic acid,
(E)-(S)-3-{4-[5-(1,3-Difluoro-phenyl)-3-methyl-pent-2-en-4-ynyloxy]-phenyl}-2-ethoxy-propionic acid,
(E)-(S)-3-{4-[5-(1,3-Dibromo-phenyl)-3-methyl-pent-2-en-4-ynyloxy]-phenyl}-2-ethoxy-propionic acid,
(E)-(S)-3-{4-[5-(1,3-Diiodo-phenyl)-3-methyl-pent-2-en-4-ynyloxy]-phenyl}-2-ethoxy-propionic acid,
(E)-(S)-3-{4-[5-(1,3-Bis-trifluoromethyl-phenyl)-3-methyl-pent-2-en-4-ynyloxy]-phenyl}-2-ethoxy-propionic acid,
(E)-(S)-3-{4-[5-(1,3-Dimethoxy-phenyl)-pent-2-en-4-ynyloxy]-phenyl}-3-methyl-2-ethoxy-propionic acid,
(E)-(S)-3-{4-[5-(1,3-Diethoxy-phenyl)-3-methyl-pent-2-en-4-ynyloxy]-phenyl}-2-ethoxy-propionic acid,
(E)-(S)-3-{4-[5-(1,3-Bis-(2,2,2-trifluoromethoxy)-phenyl)-3-methyl pent-2-en-4-ynyloxy]-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-phenyl}-2-ethoxy-propionic acid,
(E)-(S)-3-{4-[5-(3,5-Difluoro-phenyl)-3-methyl-pent-2-en-4-ynyloxy]-phenyl}-2-ethoxy-propionic acid,
(E)-(S)-3-{4-[5-(3,5-Dibromo-phenyl)-3-methyl-pent-2-en-4-ynyloxy]-phenyl}-2-ethoxy-propionic acid,
(E)-(S)-3-{4-[5-(3,5-Diiodo-phenyl)-3-methyl-pent-2-en-4-ynyloxy]-phenyl}-2-ethoxy-propionic acid,
(E)-(S)-3-{4-[5-(3,5-Bis-trifluoromethyl-phenyl)-3-methyl-pent-2-en-4-ynyloxy]-phenyl}-2-ethoxy-propionic acid,
(E)-(S)-3-{4-[5-(3,5-Dimethoxy-phenyl)-3-methyl-pent-2-en-4-ynyloxy]-phenyl}-2-ethoxy-propionic acid,
(E)-(S)-3-{4-[5-(3,5-Diethoxy-phenyl)-3-methyl-pent-2-en-4-ynyloxy]-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-phenyl}-2-ethoxy-propionic acid,
(E)-(S)-3-{4-[5-(1,3-Difluoro-phenyl)-pent-2-en-4-ynyloxy]-3-chloro-phenyl}-2-ethoxy-propionic acid,
(E)-(S)-3-{4-[5-(1,3-Dibromo-phenyl)-pent-2-en-4-ynyloxy]-3-chloro-phenyl}-2-ethoxy-propionic acid,
(E)-(S)-3-{4-[5-(1,3-Diiodo-phenyl)-pent-2-en-4-ynyloxy]-3-chloro-phenyl}-2-ethoxy-propionic acid,
(E)-(S)-3-{4-[5-(1,3-Bis-trifluoromethyl-phenyl)-pent-2-en-4-ynyloxy]-3-chloro-phenyl}-2-ethoxy-propionic acid,
(E)-(S)-3-{4-[5-(1,3-Dimethoxy-phenyl)-pent-2-en-4-ynyloxy]-3-chloro-phenyl}-2-ethoxy-propionic acid,
(E)-(S)-3-{4-[5-(1,3-Diethoxy-phenyl)-pent-2-en-4-ynyloxy]-3-chloro-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-chloro-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-chloro-phenyl}-2-ethoxy-propionic acid,
(E)-(S)-3-{4-[5-(3,5-Difluoro-phenyl)-pent-2-en-4-ynyloxy]-3-chloro-phenyl}-2-ethoxy-propionic acid,
(E)-(S)-3-{4-[5-(3,5-Dibromo-phenyl)-pent-2-en-4-ynyloxy]-3-chloro-phenyl}-2-ethoxy-propionic acid,
(E)-(S)-3-{4-[5-(3,5-Diiodo-phenyl)-pent-2-en-4-ynyloxy]-3-chloro-phenyl}-2-ethoxy-propionic acid,
(E)-(S)-3-{4-[5-(3,5-Bis-trifluoromethyl-phenyl)-pent-2-en-4-ynyloxy]-3-chloro-phenyl}-2-ethoxy-propionic acid,
(E)-(S)-3-{4-[5-(3,5-Dimethoxy-phenyl)-pent-2-en-4-ynyloxy]-3-chloro-phenyl}-2-ethoxy-propionic acid,
(E)-(S)-3-{4-[5-(3,5-Diethoxy-phenyl)-pent-2-en-4-ynyloxy]-3-chloro-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-chloro-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-chloro-phenyl}-2-ethoxy-propionic acid,
(E)-(S)-3-{4-[5-(1,3-Difluoro-phenyl)-3-methyl-pent-2-en-4-ynyloxy]-3-chloro-phenyl}-2-ethoxy-propionic acid,
(E)-(S)-3-{4-[5-(1,3-Dibromo-phenyl)-3-methyl-pent-2-en-4-ynyloxy]-3-chloro-phenyl}-2-ethoxy-propionic acid,
(E)-(S)-3-{4-[5-(1,3-Diiodo-phenyl)-3-methyl-pent-2-en-4-ynyloxy]-3-chloro-phenyl}-2-ethoxy-propionic acid,
(E)-(S)-3-{4-[5-(1,3-Bis-trifluoromethyl-phenyl)-3-methyl-pent-2-en-4-ynyloxy]-3-chloro-phenyl}-2-ethoxy-propionic acid,
(E)-(S)-3-{4-[5-(1,3-Dimethoxy-phenyl)-pent-2-en-4-ynyloxy]-3-chloro-phenyl}-3-methyl-2-ethoxy-propionic acid,
(E)-(S)-3-{4-[5-(1,3-Diethoxy-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{(4-[5-(3,5-Difluoro-phenyl)-3-methyl-pent-2-en-4-ynyloxy]-3-chloro-phenyl}-2-ethoxy-propionic acid,
(E)-(S)-3-{4-[5-(3,5-Dibromo-phenyl)-3-methyl-pent-2-en-4-ynyloxy]-3-chloro-phenyl}-2-ethoxy-propionic acid,
(E)-(S)-3-{4-[5-(3,5-Diiodo-phenyl)-3-methyl-pent-2-en-4-ynyloxy]-3-chloro-phenyl}-2-ethoxy-propionic acid,
(E)-(S)-3-{4-[5-(3,5-Bis-trifluoromethyl-phenyl)-3-methyl-pent-2-en-4-ynyloxy]-3-chloro-phenyl}-2-ethoxy-propionic acid,
(E)-(S)-3-{(4-[5-(3,5-Dimethoxy-phenyl)-3-methyl-pent-2-en-4-ynyloxy]-3-chloro-phenyl}-2-ethoxy-propionic acid,
(E)-(S)-3-{4-[5-(3,5-Diethoxy-phenyl)-3-methyl-pent-2-en-4-ynyloxy]-3-chloro-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{4-[5-(1,3-Difluoro-phenyl)-pent-2-en-4-ynyloxy]-3-bromo-phenyl}-2-ethoxy-propionic acid,
(E)-(S)-3-{4-[5-(1,3-Dibromo-phenyl)-pent-2-en-4-ynyloxy]-3-bromo-phenyl}-2-ethoxy-propionic acid,
(E)-(S)-3-{4-[5-(1,3-Diiodo-phenyl)-pent-2-en-4-ynyloxy]-3-bromo-phenyl}-2-ethoxy-propionic acid,
(E)-(S)-3-{4-[5-(1,3-Bis-trifluoromethyl-phenyl)-pent-2-en-4-ynyloxy]-3-bromo-phenyl}-2-ethoxy-propionic acid,
(E)-(S)-3-{4-[5-(1,3-Dimethoxy-phenyl)-pent-2-en-4-ynyloxy]-3-bromo-phenyl}-2-ethoxy-propionic acid,
(E)-(S)-3-{4-[5-(1,3-Diethoxy-phenyl)-pent-2-en-4-ynyloxy]-3-bromo-phenyl}-2-ethoxy-propionic acid, (E)-(S)-3-{4-[5-(1,3-Bis-(2,2,2-trifluoromethoxy)-phenyl)-pent-2-en-4-ynyloxy]-3-bromo-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(3,5-Difluoro-phenyl)-pent-2-en-4-ynyloxy]-3-bromo-phenyl}-2-ethoxy-propionic acid,
(E)-(S)-3-{4-[5-(3,5-Dibromo-phenyl)-pent-2-en-4-ynyloxy]-3-bromo-phenyl}-2-ethoxy-propionic acid,
(E)-(S)-3-{4-[5-(3,5-Diiodo-phenyl)-pent-2-en-4-ynyloxy]-3-bromo-phenyl}-2-ethoxy-propionic acid,
(E)-(S)-3-{4-[5-(3,5-Bis-trifluoromethyl-phenyl)-pent-2-en-4-ynyloxy]-3-bromo-phenyl}-2-ethoxy-propionic acid,
(E)-(S)-3-{4-[5-(3,5-Dimethoxy-phenyl)-pent-2-en-4-ynyloxy]-3-bromo-phenyl}-2-ethoxy-propionic acid,
(E)-(S)-3-{4-[5-(3,5-Diethoxy-phenyl)-pent-2-en-4-ynyloxy]-3-bromo-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-bromo-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(1,3-Difluoro-phenyl)-3-methyl-pent-2-en-4-ynyloxy]-3-bromo-phenyl}-2-ethoxy-propionic acid,
(E)-(S)-3-{4-[5-(1,3-Dibromo-phenyl)-3-methyl-pent-2-en-4-ynyloxy]-3-bromo-phenyl}-2-ethoxy-propionic acid,
(E)-(S)-3-{4-[5-(1,3-Diiodo-phenyl)-3-methyl-pent-2-en-4-ynyloxy]-3-bromo-phenyl}-2-ethoxy-propionic acid,
(E)-(S)-3-{4-[5-(1,3-Bis-trifluoromethyl-phenyl)-3-methyl-pent-2-en-4-ynyloxy]-3-bromo-phenyl}-2-ethoxy-propionic acid,
(E)-(S)-3-{4-[5-(1,3-Dimethoxy-phenyl)-pent-2-en-4-ynyloxy]-3-bromo-phenyl}-3-methyl-2-ethoxy-propionic acid,
(E)-(S)-3-{4-[5-(1,3-Diethoxy-phenyl)-3-methyl-pent-2-en-4-ynyloxy]-3-bromo-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-bromo-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid,
(E)-(S)-3-{4-[5-(3,5-Difluoro-phenyl)-3-methyl-pent-2-en-4-ynyloxy]-3-bromo-phenyl}-2-ethoxy-propionic acid,
(E)-(S)-3-{4-[5-(3,5-Dibromo-phenyl)-3-methyl-pent-2-en-4-ynyloxy]-3-bromo-phenyl}-2-ethoxy-propionic acid,
(E)-(S)-3-{4-[5-(3,5-Diiodo-phenyl)-3-methyl-pent-2-en-4-ynyloxy]-3-bromo-phenyl}-2-ethoxy-propionic acid,
(E)-(S)-3-{4-[5-(3,5-Bis-trifluoromethyl-phenyl)-3-methyl-pent-2-en-4-ynyloxy]-3-bromo-phenyl}-2-ethoxy-propionic acid,
(E)-(S)-3-{4-[5-(3,5-Dimethoxy-phenyl)-3-methyl-pent-2-en-4-ynyloxy]-3-bromo-phenyl}-2-ethoxy-propionic acid,
(E)-(S)-3-{4-[5-(3,5-Diethoxy-phenyl)-3-methyl-pent-2-en-4-ynyloxy]-3-bromo-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-bromo-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid,
(E)-(S)-3-{4-[5-(1,3-Difluoro-phenyl)-pent-2-en-4-ynyloxy]-3-iodo-phenyl}-2-ethoxy-propionic acid,
(E)-(S)-3-{4-[5-(1,3-Dibromo-phenyl)-pent-2-en-4-ynyloxy]-3-iodo-phenyl}-2-ethoxy-propionic acid,
(E)-(S)-3-{4-[5-(1,3-Diiodo-phenyl)-pent-2-en-4-ynyloxy]-3-iodo-phenyl}-2-ethoxy-propionic acid,
(E)-(S)-3-{4-[5-(1,3-Bis-trifluoromethyl-phenyl)-pent-2-en-4-ynyloxy]-3-iodo-phenyl}-2-ethoxy-propionic acid,
(E)-(S)-3-{4-[5-(1,3-Dimethoxy-phenyl)-pent-2-en-4-ynyloxy]-3-iodo-phenyl}-2-ethoxy-propionic acid,
(E)-(S)-3-{4-[5-(1,3-Diethoxy-phenyl)-pent-2-en-4-ynyloxy]-3-iodo-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-iodo-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-iodo-phenyl}-2-ethoxy-propionic acid,
(E)-(S)-3-{4-[5-(3,5-Difluoro-phenyl)-pent-2-en-4-ynyloxy]-3-iodo-phenyl}-2-ethoxy-propionic acid,
(E)-(S)-3-{4-[5-(3,5-Dibromo-phenyl)-pent-2-en-4-ynyloxy]-3-iodo-phenyl}-2-ethoxy-propionic acid,
(E)-(S)-3-{4-[5-(3,5-Diiodo-phenyl)-pent-2-en-4-ynyloxy]-3-iodo-phenyl}-2-ethoxy-propionic acid,
(E)-(S)-3-{4-[5-(3,5-Bis-trifluoromethyl-phenyl)-pent-2-en-4-ynyloxy]-3-iodo-phenyl}-2-ethoxy-propionic acid,
(E)-(S)-3-{4-[5-(3,5-Dimethoxy-phenyl)-pent-2-en-4-ynyloxy]-3-iodo-phenyl}-2-ethoxy-propionic acid,
(E)-(S)-3-{4-[5-(3,5-Diethoxy-phenyl)-pent-2-en-4-ynyloxy]-3-iodo-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-iodo-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-iodo-phenyl}-2-ethoxy-propionic acid,
(E)-(S)-3-{4-[5-(1,3-Difluoro-phenyl)-3-methyl-pent-2-en-4-ynyloxy]-3-iodo-phenyl}-2-ethoxy-propionic acid,
(E)-(S)-3-{4-[5-(1,3-Dibromo-phenyl)-3-methyl-pent-2-en-4-ynyloxy]-3-iodo-phenyl}-2-ethoxy-propionic acid,
(E)-(S)-3-{4-[5-(1,3-Diiodo-phenyl)-3-methyl-pent-2-en-4-ynyloxy]-3-iodo-phenyl}-2-ethoxy-propionic acid,
(E)-(S)-3-{4-[5-(1,3-Bis-trifluoromethyl-phenyl)-3-methyl-pent-2-en-4-ynyloxy]-3-iodo-phenyl}-2-ethoxy-propionic acid,
(E)-(S)-3-{4-[5-(1,3-Dimethoxy-phenyl)-pent-2-en-4-ynyloxy]-3-iodo-phenyl}-3-methyl-2-ethoxy-propionic acid,
(E)-(S)-3-{4-[5-(1,3-Diethoxy-phenyl)-3-methyl-pent-2-en-4-ynyloxy]-3-iodo-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid,
(E)-(S)-3-{4-[5-(3,5-Difluoro-phenyl)-3-methyl-pent-2-en-4-ynyloxy]-3-iodo-phenyl}-2-ethoxy-propionic acid,
(E)-(S)-3-{4-[5-(3,5-Dibromo-phenyl)-3-methyl-pent-2-en-4-ynyloxy]-3-iodo-phenyl}-2-ethoxy-propionic acid,
(E)-(S)-3-{4-[5-(3,5-Diiodo-phenyl)-3-methyl-pent-2-en-4-ynyloxy]-3-iodo-phenyl}-2-ethoxy-propionic acid,
(E)-(S)-3-{4-[5-(3,5-Bis-trifluoromethyl-phenyl)-3-methyl-pent-2-en-4-ynyloxy]-3-iodo-phenyl}-2-ethoxy-propionic acid,
(E)-(S)-3-{4-[5-(3,5-Dimethoxy-phenyl)-3-methyl-pent-2-en-4-ynyloxy]-3-iodo-phenyl}-2-ethoxy-propionic acid,
(E)-(S)-3-{4-[5-(3,5-Diethoxy-phenyl)-3-methyl-pent-2-en-4-ynyloxy]-3-iodo-phenyl}-2-ethoxy-propionic acid, (E)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid, and
(E)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;

or a pharmaceutically acceptable salt thereof.

Another object of the present invention provides a combination therapy pharmaceutical composition wherein the dual PPAR-α/PPAR-γ activator of formula (I) is selected from the following:

(Z)-(S)-3-{4-[5-(1,3-Difluoro-phenyl)-pent-2-en-4-ynyloxy]-phenyl}-2-ethoxy-propionic acid,
(Z)-(S)-3-{4-[5-(1,3-Dibromo-phenyl)-pent-2-en-4-ynyloxy]-phenyl}-2-ethoxy-propionic acid,
(Z)-(S)-3-{4-[5-(1,3-Diiodo-phenyl)-pent-2-en-4-ynyloxy]-phenyl}-2-ethoxy-propionic acid,
(Z)-(S)-3-{4-[5-(1,3-Bis-trifluoromethyl-phenyl)-pent-2-en-4-ynyloxy]-phenyl}-2-ethoxy-propionic acid,
(Z)-(S)-3-{4-[5-(1,3-Dimethoxy-phenyl)-pent-2-en-4-ynyloxy]-phenyl}-2-ethoxy-propionic acid,
(Z)-(S)-3-{4-[5-(1,3-Diethoxy-phenyl)-pent-2-en-4-ynyloxy]-phenyl}-2-ethoxy-propionic acid,
(Z)-(S)-3-{4-[5-(1,3-Bis-(2,2,2-trifluoromethoxy)-phenyl)-pent-2-en-4-ynyloxy]-phenyl}-2-ethoxy-propionic acid,
(Z)-(S)-3-{4-[5-(1,3-Bis-(2,2,2-trifluoroethoxy)-phenyl)-pent-2-en-4-ynyloxy]-phenyl}-2-ethoxy-propionic acid,
(Z)-(S)-3-{4-[5-(3,5-Difluoro-phenyl)-pent-2-en-4-ynyloxy]-phenyl}-2-ethoxy-propionic acid,
(Z)-(S)-3-{4-[5-(3,5-Dibromo-phenyl)-pent-2-en-4-ynyloxy]-phenyl}-2-ethoxy-propionic acid,
(Z)-(S)-3-{4-[5-(3,5-Diiodo-phenyl)-pent-2-en-4-ynyloxy]-phenyl}-2-ethoxy-propionic acid,
(Z)-(S)-3-{4-[5-(3,5-Bis-trifluoromethyl-phenyl)-pent-2-en-4-ynyloxy]-phenyl}-2-ethoxy-propionic acid,
(Z)-(S)-3-{4-[5-(3,5-Dimethoxy-phenyl)-pent-2-en-4-ynyloxy]-phenyl}-2-ethoxy-propionic acid,
(Z)-(S)-3-{4-[5-(3,5-Diethoxy-phenyl)-pent-2-en-4-ynyloxy]-phenyl}-2-ethoxy-propionic acid,
(Z)-(S)-3-{4-[5-(3,5-Bis-(2,2,2-trifluoromethoxy)-phenyl)-pent-2-en-4-ynyloxy]-phenyl}-2-ethoxy-propionic acid,
(Z)-(S)-3-{4-[5-(3,5-Bis-(2,2,2-trifluoroethoxy)-phenyl)-pent-2-en-4-ynyloxy]-phenyl}-2-ethoxy-propionic acid,
(Z)-(S)-3-{4-[5-(1,3-Difluoro-phenyl)-3-methyl-pent-2-en-4-ynyloxy]-phenyl}-2-ethoxy-propionic acid,
(Z)-(S)-3-{4-[5-(1,3-Dibromo-phenyl)-3-methyl-pent-2-en-4-ynyloxy]-phenyl}-2-ethoxy-propionic acid,
(Z)-(S)-3-{4-[5-(1,3-Diiodo-phenyl)-3-methyl-pent-2-en-4-ynyloxy]-phenyl}-2-ethoxy-propionic acid,
(Z)-(S)-3-{4-[5-(1,3-Bis-trifluoromethyl-phenyl)-3-methyl-pent-2-en-4-ynyloxy]-phenyl}-2-ethoxy-propionic acid,
(Z)-(S)-3-{4-[5-(1,3-Dimethoxy-phenyl)-pent-2-en-4-ynyloxy]-phenyl}-3-methyl-2-ethoxy-propionic acid,
(Z)-(S)-3-{4-[5-(1,3-Diethoxy-phenyl)-3-methyl-pent-2-en-4-ynyloxy]-phenyl}-2-ethoxy-propionic acid,
(Z)-(S)-3-{4-[5-(1,3-Bis-(2,2,2-trifluoromethoxy)-phenyl)-3-methyl pent-2-en-4-ynyloxy]-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-phenyl}-2-ethoxy-propionic acid,
(Z)-(S)-3-{4-[5-(3,5-Difluoro-phenyl)-3-methyl-pent-2-en-4-ynyloxy]-phenyl}-2-ethoxy-propionic acid,
(Z)-(S)-3-{4-[5-(3,5-Dibromo-phenyl)-3-methyl-pent-2-en-4-ynyloxy]-phenyl}-2-ethoxy-propionic acid,
(Z)-(S)-3-{4-[5-(3,5-Diiodo-phenyl)-3-methyl-pent-2-en-4-ynyloxy]-phenyl}-2-ethoxy-propionic acid,
(Z)-(S)-3-{4-[5-(3,5-Bis-trifluoromethyl-phenyl)-3-methyl-pent-2-en-4-ynyloxy]-phenyl}-2-ethoxy-propionic acid,
(Z)-(S)-3-{4-[5-(3,5-Dimethoxy-phenyl)-3-methyl-pent-2-en-4-ynyloxy]-phenyl}-2-ethoxy-propionic acid,
(Z)-(S)-3-{4-[5-(3,5-Diethoxy-phenyl)-3-methyl-pent-2-en-4-ynyloxy]-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-phenyl}-2-ethoxy-propionic acid,
(Z)-(S)-3-{4-[5-(1,3-Difluoro-phenyl)-pent-2-en-4-ynyloxy]-3-chloro-phenyl}-2-ethoxy-propionic acid,
(Z)-(S)-3-{4-[5-(1,3-Dibromo-phenyl)-pent-2-en-4-ynyloxy]-3-chloro-phenyl}-2-ethoxy-propionic acid,
(Z)-(S)-3-{4-[5-(1,3-Diiodo-phenyl)-pent-2-en-4-ynyloxy]-3-chloro-phenyl}-2-ethoxy-propionic acid,
(Z)-(S)-3-{4-[5-(1,3-Bis-trifluoromethyl-phenyl)-pent-2-en-4-ynyloxy]-3-chloro-phenyl}-2-ethoxy-propionic acid,
(Z)-(S)-3-{4-[5-(1,3-Dimethoxy-phenyl)-pent-2-en-4-ynyloxy]-3-chloro-phenyl}-2-ethoxy-propionic acid,
(Z)-(S)-3-{4-[5-(1,3-Diethoxy-phenyl)-pent-2-en-4-ynyloxy]-3-chloro-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-chloro-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-chloro-phenyl}-2-ethoxy-propionic acid,
(Z)-(S)-3-{4-[5-(3,5-Difluoro-phenyl)-pent-2-en-4-ynyloxy]-3-chloro-phenyl}-2-ethoxy-propionic acid,
(Z)-(S)-3-{4-[5-(3,5-Dibromo-phenyl)-pent-2-en-4-ynyloxy]-3-chloro-phenyl}-2-ethoxy-propionic acid,
(Z)-(S)-3-{4-[5-(3,5-Diiodo-phenyl)-pent-2-en-4-ynyloxy]-3-chloro-phenyl}-2-ethoxy-propionic acid,
(Z)-(S)-3-{(4-[5-(3,5-Bis-trifluoromethyl-phenyl)-pent-2-en-4-ynyloxy]-3-chloro-phenyl}-2-ethoxy-propionic acid,
(Z)-(S)-3-{4-[5-(3,5-Dimethoxy-phenyl)-pent-2-en-4-ynyloxy]-3-chloro-phenyl}-2-ethoxy-propionic acid,
(Z)-(S)-3-{4-[5-(3,5-Diethoxy-phenyl)-pent-2-en-4-ynyloxy]-3-chloro-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-chloro-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-chloro-phenyl}-2-ethoxy-propionic acid,
(Z)-(S)-3-{4-[5-(1,3-Difluoro-phenyl)-3-methyl-pent-2-en-4-ynyloxy]-3-chloro-phenyl}-2-ethoxy-propionic acid,
(Z)-(S)-3-{4-[5-(1,3-Dibromo-phenyl)-3-methyl-pent-2-en-4-ynyloxy]-3-chloro-phenyl}-2-ethoxy-propionic acid,
(Z)-(S)-3-{4-[5-(1,3-Diiodo-phenyl)-3-methyl-pent-2-en-4-ynyloxy]-3-chloro-phenyl}-2-ethoxy-propionic acid,
(Z)-(S)-3-{4-[5-(1,3-Bis-trifluoromethyl-phenyl)-3-methyl-pent-2-en-4-ynyloxy]-3-chloro-phenyl}-2-ethoxy-propionic acid,
(Z)-(S)-3-{4-[5-(1,3-Dimethoxy-phenyl)-pent-2-en-4-ynyloxy]-3-chloro-phenyl}-3-methyl-2-ethoxy-propionic acid,
(Z)-(S)-3-{4-[5-(1,3-Diethoxy-phenyl)-3-methyl-pent-2-en-4-ynyloxy]-3-chloro-phenyl}-2-ethoxy-propionic acid, (Z)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid,
(Z)-(S)-3-{4-[5-(3,5-Difluoro-phenyl)-3-methyl-pent-2-en-4-ynyloxy]-3-chloro-phenyl}-2-ethoxy-propionic acid,
(Z)-(S)-3-{4-[5-(3,5-Dibromo-phenyl)-3-methyl-pent-2-en-4-ynyloxy]-3-chloro-phenyl}-2-ethoxy-propionic acid,
(Z)-(S)-3-{4-[5-(3,5-Diiodo-phenyl)-3-methyl-pent-2-en-4-ynyloxy]-3-chloro-phenyl}-2-ethoxy-propionic acid,
(Z)-(S)-3-{4-[5-(3,5-Bis-trifluoromethyl-phenyl)-3-methyl-pent-2-en-4-ynyloxy]-3-chloro-phenyl}-2-ethoxy-propionic acid,
(Z)-(S)-3-{4-[5-(3,5-Dimethoxy-phenyl)-3-methyl-pent-2-en-4-ynyloxy]-3-chloro-phenyl}-2-ethoxy-propionic acid,
(Z)-(S)-3-{4-[5-(3,5-Diethoxy-phenyl)-3-methyl-pent-2-en-4-ynyloxy]-3-chloro-phenyl}-2-ethoxy-propionic acid,
(Z)-(S)-3-{(4-[5-(3,5-Bis-(2,2,2-trifluoromethoxy)-phenyl)-3-methyl-pent-2-en-4-ynyloxy]-3-chloro-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid,
(Z)-(S)-3-{4-[5-(1,3-Difluoro-phenyl)-pent-2-en-4-ynyloxy]-3-bromo-phenyl}-2-ethoxy-propionic acid,
(Z)-(S)-3-{4-[5-(1,3-Dibromo-phenyl)-pent-2-en-4-ynyloxy]-3-bromo-phenyl}-2-ethoxy-propionic acid,
(Z)-(S)-3-{4-[5-(1,3-Diiodo-phenyl)-pent-2-en-4-ynyloxy]-3-bromo-phenyl}-2-ethoxy-propionic acid,
(Z)-(S)-3-{4-[5-(1,3-Bis-trifluoromethyl-phenyl)-pent-2-en-4-ynyloxy]-3-bromo-phenyl}-2-ethoxy-propionic acid,
(Z)-(S)-3-{4-[5-(1,3-Dimethoxy-phenyl)-pent-2-en-4-ynyloxy]-3-bromo-phenyl}-2-ethoxy-propionic acid,
(Z)-(S)-3-{4-[5-(1,3-Diethoxy-phenyl)-pent-2-en-4-ynyloxy]-3-bromo-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-bromo-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-bromo-phenyl}-2-ethoxy-propionic acid,
(Z)-(S)-3-{4-[5-(3,5-Difluoro-phenyl)-pent-2-en-4-ynyloxy]-3-bromo-phenyl}-2-ethoxy-propionic acid,
(Z)-(S)-3-{4-[5-(3,5-Dibromo-phenyl)-pent-2-en-4-ynyloxy]-3-bromo-phenyl}-2-ethoxy-propionic acid,
(Z)-(S)-3-{4-[5-(3,5-Diiodo-phenyl)-pent-2-en-4-ynyloxy]-3-bromo-phenyl}-2-ethoxy-propionic acid,
(Z)-(S)-3-{4-[5-(3,5-Bis-trifluoromethyl-phenyl)-pent-2-en-4-ynyloxy]-3-bromo-phenyl}-2-ethoxy-propionic acid,
(Z)-(S)-3-{4-[5-(3,5-Dimethoxy-phenyl)-pent-2-en-4-ynyloxy]-3-bromo-phenyl}-2-ethoxy-propionic acid,
(Z)-(S)-3-{4-[5-(3,5-Diethoxy-phenyl)-pent-2-en-4-ynyloxy]-3-bromo-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-bromo-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-bromo-phenyl}-2-ethoxy-propionic acid,
(Z)-(S)-3-{4-[5-(1,3-Difluoro-phenyl)-3-methyl-pent-2-en-4-ynyloxy]-3-bromo-phenyl}-2-ethoxy-propionic acid,
(Z)-(S)-3-{4-[5-(1,3-Dibromo-phenyl)-3-methyl-pent-2-en-4-ynyloxy]-3-bromo-phenyl}-2-ethoxy-propionic acid,
(Z)-(S)-3-{4-[5-(1,3-Diiodo-phenyl)-3-methyl-pent-2-en-4-ynyloxy]-3-bromo-phenyl}-2-ethoxy-propionic acid,
(Z)-(S)-3-{4-[5-(1,3-Bis-trifluoromethyl-phenyl)-3-methyl-pent-2-en-4-ynyloxy]-3-bromo-phenyl}-2-ethoxy-propionic acid,
(Z)-(S)-3-{4-[5-(1,3-Dimethoxy-phenyl)-pent-2-en-4-ynyloxy]-3-bromo-phenyl}-3-methyl-2-ethoxy-propionic acid,
(Z)-(S)-3-{4-[5-(1,3-Diethoxy-phenyl)-3-methyl-pent-2-en-4-ynyloxy]-3-bromo-phenyl}-2-ethoxy-propionic acid,
(Z)-(S)-3-{4-[5-(1,3-Bis-(2,2,2-trifluoromethoxy)-phenyl)-3-methyl-pent-2-en-4-ynyloxy]-3-bromo-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid,
(Z)-(S)-3-{4-[5-(3,5-Difluoro-phenyl)-3-methyl-pent-2-en-4-ynyloxy]-3-bromo-phenyl}-2-ethoxy-propionic acid,
(Z)-(S)-3-{4-[5-(3,5-Dibromo-phenyl)-3-methyl-pent-2-en-4-ynyloxy]-3-bromo-phenyl}-2-ethoxy-propionic acid,
(Z)-(S)-3-{4-[5-(3,5-Diiodo-phenyl)-3-methyl-pent-2-en-4-ynyloxy]-3-bromo-phenyl}-2-ethoxy-propionic acid,
(Z)-(S)-3-{4-[5-(3,5-Bis-trifluoromethyl-phenyl)-3-methyl-pent-2-en-4-ynyloxy]-3-bromo-phenyl}-2-ethoxy-propionic acid,
(Z)-(S)-3-{4-[5-(3,5-Dimethoxy-phenyl)-3-methyl-pent-2-en-4-ynyloxy]-3-bromo-phenyl}-2-ethoxy-propionic acid,
(Z)-(S)-3-{4-[5-(3,5-Diethoxy-phenyl)-3-methyl-pent-2-en-4-ynyloxy]-3-bromo-phenyl}-2-ethoxy-propionic acid,
(Z)-(S)-3-{4-[5-(3,6-Bis-(2,2,2-trifluoromethoxy)-phenyl)-3-methyl-pent-2-en-4-ynyloxy]-3-bromo-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid,
(Z)-(S)-3-{4-[5-(1,3-Difluoro-phenyl)-pent-2-en-4-ynyloxy]-3-iodo-phenyl}-2-ethoxy-propionic acid,
(Z)-(S)-3-{4-[5-(1,3-Dibromo-phenyl)-pent-2-en-4-ynyloxy]-3-iodo-phenyl}-2-ethoxy-propionic acid,
(Z)-(S)-3-{4-[5-(1,3-Diiodo-phenyl)-pent-2-en-4-ynyloxy]-3-iodo-phenyl}-2-ethoxy-propionic acid,
(Z)-(S)-3-{4-[5-(1,3-Bis-trifluoromethyl-phenyl)-pent-2-en-4-ynyloxy]-3-iodo-phenyl}-2-ethoxy-propionic acid,
(Z)-(S)-3-{4-[5-(1,3-Dimethoxy-phenyl)-pent-2-en-4-ynyloxy]-3-iodo-phenyl}-2-ethoxy-propionic acid,
(Z)-(S)-3-{4-[5-(1,3-Diethoxy-phenyl)-pent-2-en-4-ynyloxy]-3-iodo-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-iodo-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(3,5-Difluoro-phenyl)-pent-2-en-4-ynyloxy]-3-iodo-phenyl}-2-ethoxy-propionic acid,
(Z)-(S)-3-{4-[5-(3,5-Dibromo-phenyl)-pent-2-en-4-ynyloxy]-3-iodo-phenyl}-2-ethoxy-propionic acid,
(Z)-(S)-3-{4-[5-(3,5-Diiodo-phenyl)-pent-2-en-4-ynyloxy]-3-iodo-phenyl}-2-ethoxy-propionic acid,
(Z)-(S)-3-{4-[5-(3,5-Bis-trifluoromethyl-phenyl)-pent-2-en-4-ynyloxy]-3-iodo-phenyl}-2-ethoxy-propionic acid,
(Z)-(S)-3-{4-[5-(3,5-Dimethoxy-phenyl)-pent-2-en-4-ynyloxy]-3-iodo-phenyl}-2-ethoxy-propionic acid, (Z)-(S)-3-{4-[5-(3,5-Diethoxy-phenyl)-pent-2-en-4-yny-loxy]-3-iodo-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-iodo-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(1,3-Difluoro-phenyl)-3-methyl-pent-2-en-4-ynyloxy]-3-iodo-phenyl}-2-ethoxy-propionic acid,
(Z)-(S)-3-{4-[5-(1,3-Dibromo-phenyl)-3-methyl-pent-2-en-4-ynyloxy]-3-iodo-phenyl}-2-ethoxy-propionic acid,
(Z)-(S)-3-{4-[5-(1,3-Diiodo-phenyl)-3-methyl-pent-2-en-4-ynyloxy]-3-iodo-phenyl}-2-ethoxy-propionic acid,
(Z)-(S)-3-{4-[5-(1,3-Bis-trifluoromethyl-phenyl)-3-methyl-pent-2-en-4-ynyloxy]-3-iodo-phenyl}-2-ethoxy-propionic acid,
(Z)-(S)-3-{4-[5-(1,3-Dimethoxy-phenyl)-pent-2-en-4-ynyloxy]-3-iodo-phenyl}-3-methyl-2-ethoxy-propionic acid,
(Z)-(S)-3-{4-[5-(1,3-Diethoxy-phenyl)-3-methyl-pent-2-en-4-ynyloxy]-3-iodo-phenyl}-2-ethoxy-propionic acid,
(Z)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid,
(Z)-(S)-3-{4-[5-(3,5-Difluoro-phenyl)-3-methyl-pent-2-en-4-ynyloxy]-3-iodo-phenyl}-2-ethoxy-propionic acid,
(Z)-(S)-3-{4-[5-(3,5-Dibromo-phenyl)-3-methyl-pent-2-en-4-ynyloxy]-3-iodo-phenyl}-2-ethoxy-propionic acid,
(Z)-(S)-3-{4-[5-(3,5-Diiodo-phenyl)-3-methyl-pent-2-en-4-ynyloxy]-3-iodo-phenyl}-2-ethoxy-propionic acid,
(Z)-(S)-3-{4-[5-(3,5-Bis-trifluoromethyl-phenyl)-3-methyl-pent-2-en-4-ynyloxy]-3-iodo-phenyl}-2-ethoxy-propionic acid,
(Z)-(S)-3-{4-[5-(3,5-Dimethoxy-phenyl)-3-methyl-pent-2-en-4-ynyloxy]-3-iodo-phenyl}-2-ethoxy-propionic acid,
(Z)-(S)-3-{4-[5-(3,5-Diethoxy-phenyl)-3-methyl-pent-2-en-4-ynyloxy]-3-iodo-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid, and
(Z)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;

or a pharmaceutically acceptable salt thereof.

Another object of the present invention provides a combination therapy pharmaceutical composition wherein the GLP-1 derivative comprises a sequence wherein at least one amino acid residue of the sequence has a lipophilic substituent attached, with the proviso that if only one lipophilic substituent is present and this substituent is attached to the N-terminal or to the C-terminal amino acid residue of the parent peptide then this substituent is an alkyl group or a group which has an ω-carboxylic acid group.

Another object of the present invention provides a combination therapy pharmaceutical composition wherein the GLP-1 derivative comprises a peptide selected from the group GLP-1(1-35); GLP-1(1-36); GLP-1(1-36)amide; GLP-1(1-37); GLP-1(1-38); GLP-1(1-39); GLP-1(1-40); GLP-1(1-41).

Another object of the present invention provides a combination therapy pharmaceutical composition wherein the GLP-1 derivative comprises a peptide selected from the group GLP-1(7-35); GLP-1(7-36); GLP-1(7-36)amide; GLP-1(7-37); GLP-1(7-38); GLP-1(7-39); GLP-1(7-40) and GLP-1(7-41).

Another object of the present invention provides a combination therapy pharmaceutical composition wherein the GLP-1 derivative comprises a peptide selected from the group: $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26,34}Lys^{38}$GLP-1(7-38); $Arg^{26,34}Lys^{39}$-GLP-1(7-39); $Arg^{26,34}Lys^{40}$-GLP-1(7-40); $Arg^{26}Lys^{36}$-GLP-1(7-37); $Arg^{34}Lys^{36}$-GLP-1(7-37); $Arg^{26}Lys^{39}$-GLP-1(7-39); $Arg^{34}Lys^{40}$-GLP-1(7-40); $Arg^{26,34}Lys^{36,39}$-GLP-1(7-39); $Arg^{26,34}Lys^{36,40}$-GLP-1(7-40); $Gly^{8}Arg^{26}$-GLP-1(7-37); $Gly^{8}Arg^{34}$-GLP-1(7-37); $Gly^{8}Lys^{36}$-GLP-1(7-37); $Gly^{8}Arg^{26,34}Lys^{36}$-GLP-1(7-37); $Gly^{8}Arg^{26,34}Lys^{39}$-GLP-1(7-39); $Gly^{8}Arg^{26,34}Lys^{40}$-GLP-1(7-40); $Gly^{8}Arg^{26}Lys^{36}$-GLP-1(7-37); $Gly^{8}Arg^{34}Lys^{36}$-GLP-1(7-37); $Gly^{8}Arg^{26}Lys^{39}$-GLP-1(7-39); $Gly^{8}Arg^{34}Lys^{40}$-GLP-1(7-40); $Gly^{8}Arg^{26,34}Lys^{36,39}$-GLP-1(7-39) and $Gly^{8}Arg^{26,34}Lys^{36,40}$-GLP-1(7-40).

Another object of the present invention provides a combination therapy pharmaceutical composition comprising a GLP-1 derivative wherein the lipophilic substituent is the acyl group of a straight-chain or branched fatty acid.

Another object of the present invention provides a combination therapy pharmaceutical composition comprising a GLP-1 derivative wherein the lipophilic substituent comprises an acyl group comprising $CH_3(CH_2)_nCO—$, wherein n is 4 to 38.

Another object of the present invention provides a combination therapy pharmaceutical composition comprising a GLP-1 derivative wherein the lipophilic substituent comprises an acyl group wherein the acyl group is selected from $CH_3(CH_2)_6CO—$, $CH_3(CH_2)_8CO—$, $CH_3(CH_2)_{10}CO—$, $CH_3(CH_2)_{12}CO—$, $CH_3(CH_2)_{14}CO—$, $CH_3(CH_2)_{16}CO—$, $CH_3(CH_2)_{18}CO—$, $CH_3(CH_2)_{20}CO—$ and $CH_3(CH_2)_{22}CO—$.

Another object of the present invention provides a combination therapy pharmaceutical composition comprising a GLP-1 derivative wherein the parent peptide for the derivative according to the invention is selected from the group comprising $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26}Lys^{38}$GLP-1(7-38); $Arg^{26,34}Lys^{39}$-GLP-1(7-39); $Arg^{26,34}Lys^{40}$-GLP-1(7-40); $Arg^{26}Lys^{36}$-GLP-1(7-37); $Arg^{34}Lys^{36}$-GLP-1(7-37); $Arg^{26}Lys^{39}$-GLP-1(7-39); $Arg^{34}Lys^{40}$-GLP-1(7-40); $Arg^{26,34}Lys^{36,39}$-GLP-1(7-39); $Arg^{26,34}Lys^{36,40}$-GLP-1(7-40); $Gly^{8}Arg^{26}$-GLP-1(7-37); $Gly^{8}Arg^{34}$-GLP-1(7-37); $Gly^{8}Lys^{36}$-GLP-1(7-37); $Gly^{8}Arg^{26,34}Lys^{36}$-GLP-1(7-37); $Gly^{8}Arg^{26,34}Lys^{39}$-GLP-1(7-39); $Gly^{8}Arg^{26,34}Lys^{40}$-GLP-1(7-40); $Gly^{8}Arg^{26}Lys^{36}$-GLP-1(7-37); $Gly^{8}Arg^{34}Lys^{36}$-GLP-1(7-37); $Gly^{8}Arg^{26}Lys^{39}$-GLP-1(7-39); $Gly^{8}Arg^{34}Lys^{40}$-GLP-1(7-40); $Gly^{8}Arg^{26,34}Lys^{36,39}$-GLP-1(7-39) and $Gly^{8}Arg^{26,34}Lys^{36,40}$GLP 1(7-40).

Another object of the present invention provides a combination therapy pharmaceutical composition comprising a GLP-1 derivative wherein the parent peptide for the derivative according to the invention is selected from the group comprising $Arg^{26,34}Lys^{38}$ GLP-1(7-38); $Arg^{26,34}Lys^{39}$GLP-1(7-39); $Arg^{26,34}Lys^{40}$GLP-1(7-40); $Arg^{26,34}Lys^{41}$GLP-1(7-41); $Arg^{26,34}Lys^{42}$GLP-1(7-42); $Arg^{26,34}Lys^{43}$GLP-1(7-43); $Arg^{26,34}Lys^{44}$GLP-1(7-44); $Arg^{26,34}Lys^{45}$GLP-1(7-45); $Arg^{26,34}Lys^{38}$GLP-1(1-38); $Arg^{26,34}Lys^{39}$GLP-1(1-39); $Arg^{26,34}Lys^{40}$GLP-1(1-40); $Arg^{26,34}Lys^{41}$GLP-1(1-41); $Arg^{26,34}Lys^{42}$GLP-1(1-42); $Arg^{26,34}Lys^{43}$GLP-1(1-43); $Arg^{26,34}Lys^{44}$GLP-1(1-44); $Arg^{26,34}Lys^{45}$GLP-1(1-45); $Arg^{26,34}Lys^{38}$GLP-1(2-38); $Arg^{26,34}Lys^{39}$GLP-1(2-39);

Arg$^{26,34}$Lys$^{40}$GLP-1(2-40); Arg$^{26,34}$Lys$^{41}$GLP-1(2-41);
Arg$^{26,34}$Lys$^{42}$GLP-1(2-42); Arg$^{26,34}$Lys$^{43}$GLP-1(2-43);
Arg$^{26,34}$Lys$^{44}$GLP-1(2-44); Arg$^{26,34}$Lys$^{45}$GLP-1(2-45);
Arg$^{26,34}$Lys$^{38}$GLP-1(3-38); Arg$^{26,34}$Lys$^{39}$GLP-1(3-39);
Arg$^{26,34}$Lys$^{40}$GLP-1(3-40); Arg$^{26,34}$Lys$^{41}$GLP-1(3-41);
Arg$^{26}$3Lys$^{42}$GLP-1(3-42); Arg$^{26,34}$Lys$^{43}$GLP-1(3-43);
Arg$^{26,34}$Lys$^{44}$GLP-1(3-44); Arg$^{26,34}$Lys$^{45}$GLP-1(3-45);
Arg$^{26,34}$Lys$^{38}$GLP-1(4-38); Arg$^{26,34}$Lys$^{39}$GLP-1(4-39);
Arg$^{26,34}$Lys$^{40}$GLP-1(4-40); Arg$^{26,34}$Lys$^{41}$ GLP-1(4-41);
Arg$^{26,34}$Lys$^{42}$GLP-1(4-42); Arg$^{26,34}$Lys$^{43}$GLP-1(4-43);
Arg$^{26,34}$Lys$^{44}$GLP-1(4-44); Arg$^{26,34}$Lys$^{45}$GLP-1(4-45);
Arg$^{26,34}$Lys$^{38}$GLP-1(5-38); Arg$^{26,34}$Lys$^{39}$GLP-1(5-39);
Arg$^{26,34}$Lys$^{40}$GLP-1(5-40); Arg$^{26,34}$Lys$^{41}$GLP-1(5-41);
Arg$^{26,34}$Lys$^{42}$GLP-1(5-42); Arg$^{26,34}$Lys$^{43}$GLP-1(5-43);
Arg$^{26,34}$Lys$^{44}$GLP-1(5-44); Arg$^{26,34}$Lys$^{45}$GLP-1(5-45);
Arg$^{26,34}$Lys$^{38}$GLP-1(6-38); Arg$^{26,34}$Lys$^{39}$GLP-1(6-39);
Arg$^{26,34}$Lys$^{40}$GLP-1(6-40); Arg$^{26,34}$Lys$^{41}$GLP-1(6-41);
Arg$^{26,34}$Lys$^{42}$GLP-1(6-42); Arg$^{26,34}$Lys$^{43}$GLP-1(6-43);
Arg$^{26,34}$Lys$^{44}$GLP-1(6-44); Arg$^{26,34}$Lys$^{45}$GLP-1(6-45);
Arg$^{26}$Lys$^{38}$GLP-1(1-38); Arg$^{34}$Lys$^{38}$GLP-1(1-38);
Arg$^{26,34}$Lys$^{36,38}$GLP-1(1-38); Arg$^{26}$Lys$^{38}$GLP-1(7-38);
Arg$^{34}$Lys$^{38}$GLP-1(7-38); Arg$^{26,34}$Lys$^{36,38}$GLP-1(7-38);
Arg$^{26,34}$Lys$^{38}$GLP-1(7-38); Arg$^{26}$Lys$^{39}$GLP-1(1-39);
Arg$^{34}$Lys$^{39}$GLP-1(1-39); Arg$^{26,34}$Lys$^{36,39}$GLP-1(1-39);
Arg$^{26}$Lys$^{39}$GLP-1(7-39); Arg$^{34}$Lys$^{39}$GLP-1(7-39) and
Arg$^{26,34}$Lys$^{36,39}$GLP-1(7-39).

Another object of the present invention provides a combination therapy pharmaceutical composition comprising a GLP-1 derivative wherein the parent peptide for the derivative according to the invention is selected from the group comprising Arg$^{26}$-GLP-1(7-37), Arg$^{34}$-GLP-1(7-37), Lys$^{36}$-GLP-1(7-37), Arg$^{26,34}$Lys$^{36}$-GLP-1(7-37), Arg$^{26}$Lys$^{36}$-GLP-1(7-37), Arg$^{34}$Lys$^{36}$-GLP-1(7-37), Gly$^8$Arg$^{26}$-GLP-1(7-37), Gly$^8$Arg$^{34}$-GLP-1(7-37), Gly$^8$Lys$^{36}$-GLP-1(7-37), Gly$^8$Arg$^{26,34}$Lys$^{36}$-GLP-1(7-37), Gly$^8$Arg$^{26}$Lys$^{36}$-GLP-1(7-37) and Gly$^8$Arg$^{34}$Lys$^{36}$-GLP-1(7-37).

Another object of the present invention provides a combination therapy pharmaceutical composition comprising a GLP-1 derivative wherein the parent peptide for the derivative according to the invention is selected from the group comprising Arg$^{26}$Lys$^{38}$-GLP-1(7-38), Arg$^{26,34}$Lys$^{38}$-GLP-1(7-38), Arg$^{26,34}$Lys$^{36,38}$-GLP-1(7-38), Gly$^8$Arg$^{26}$Lys$^{38}$-GLP-1(7-38) and Gly$^8$Arg$^{26,34}$Lys$^{36,38}$-GLP-1(7-38).

Another object of the present invention provides a combination therapy pharmaceutical composition comprising a GLP-1 derivative wherein the parent peptide for the derivative according to the invention is selected from the group comprising Arg$^{26}$Lys$^{39}$-GLP-1(7-39), Arg$^{26,34}$Lys$^{36,39}$-GLP-1(7-39), Gly$^8$Arg$^{26}$Lys$^{39}$-GLP-1(7-39) and Gly$^8$Arg$^{26,34}$Lys$^{36,39}$-GLP-1(7-39).

Another object of the present invention provides a combination therapy pharmaceutical composition comprising a GLP-1 derivative wherein the parent peptide for the derivative according to the invention is selected from the group comprising Arg$^{34}$Lys$^{40}$-GLP-1(7-40), Arg$^{26,34}$Lys$^{36,40}$-GLP-1(7-40), Gly$^8$Arg$^{34}$Lys$^{40}$-GLP-1(7-40) and Gly$^8$Arg$^{26,34}$Lys$^{36,40}$-GLP-1(7-40).

Another object of the present invention provides a combination therapy pharmaceutical composition comprising a GLP-1 derivative wherein the parent peptide for the derivative according to the invention is selected from the group comprising:
Lys$^{26}$(N$^\epsilon$-tetradecanoyl)-GLP-1(7-37);
Lys$^{34}$(N$^\epsilon$-tetradecanoyl)-GLP-1(7-37);
Lys$^{26,34}$-bis(N$^\epsilon$-tetradecanoyl)-GLP-1(7-37);
Gly$^8$Lys$^{26}$(N$^\epsilon$-tetradecanoyl)-GLP-1(7-37);
Gly$^8$Lys$^{34}$(N$^\epsilon$-tetradecanoyl)-GLP-1(7-37);
Gly$^8$Lys$^{26,34}$-bis(N$^\epsilon$-tetradecanoyl)-GLP-1(7-37);
Arg$^{26}$Lys$^{34}$(N$^\epsilon$-tetradecanoyl)-GLP-1(7-37);
Lys$^{26}$(N$^\epsilon$-tetradecanoyl)-GLP-1(7-38);
Lys$^{34}$(N$^\epsilon$-tetradecanoyl)-GLP-1(7-38);
Lys$^{26,34}$-bis(N$^\epsilon$-tetradecanoyl)-GLP-1(7-38);
Gly$^8$Lys$^{26}$(N$^\epsilon$-tetradecanoyl)-GLP-1(7-38);
Gly$^8$Lys$^{34}$(N$^\epsilon$-tetradecanoyl)-GLP-1(7-38);
Gly$^8$Lys$^{26,34}$-bis(N$^\epsilon$-tetradecanoyl)-GLP-1(7-38);
Arg$^{26}$Lys$^{34}$(N$^\epsilon$-tetradecanoyl)-GLP-1(7-38);
Lys$^{26}$(N$^\epsilon$-tetradecanoyl)-GLP-1(7-39);
Lys$^{34}$(N$^\epsilon$-tetradecanoyl)-GLP-1(7-39);
Lys$^{26,34}$-bis(N$^\epsilon$-tetradecanoyl)-GLP-1(7-39);
Gly$^8$Lys$^{26}$(N$^\epsilon$-tetradecanoyl)-GLP-1(7-39);
Gly$^8$Lys$^{34}$(N$^\epsilon$-tetradecanoyl)-GLP-1(7-39);
Gly$^8$Lys$^{26,34}$-bis(N$^\epsilon$-tetradecanoyl)-GLP-1(7-39);
Arg$^{26}$Lys$^{34}$(N$^\epsilon$-tetradecanoyl)-GLP-1(7-39);
Lys$^{26}$(N$^\epsilon$-tetradecanoyl)-GLP-1(7-40);
Lys$^{34}$(N$^\epsilon$-tetradecanoyl)-GLP-1(7-40);
Lys$^{26,34}$-bis(N$^\epsilon$-tetradecanoyl)-GLP-1(7-40);
Gly$^8$Lys$^{26}$(N$^\epsilon$-tetradecanoyl)-GLP-1(7-40);
Gly$^8$Lys$^{34}$(N$^\epsilon$-tetradecanoyl)-GLP-1(7-40);
Gly$^8$Lys$^{26,34}$-bis(N$^\epsilon$-tetradecanoyl)-GLP-1(7-40);
Arg$^{26}$Lys$^{34}$(N$^\epsilon$-tetradecanoyl)-GLP-1(7-40);
Lys$^{26}$(N$^\epsilon$-tetradecanoyl)-GLP-1(7-36);
Lys$^{34}$(N$^\epsilon$-tetradecanoyl)-GLP-1(7-36);
Lys$^{26,34}$-bis(N$^\epsilon$-tetradecanoyl)-GLP-1(7-36);
Gly$^8$Lys$^{26}$(N$^\epsilon$-tetradecanoyl)-GLP-1(7-36);
Gly$^8$Lys$^{34}$(N$^\epsilon$-tetradecanoyl)-GLP-1(7-36);
Gly$^8$Lys$^{26}$34-bis(N$^\epsilon$-tetradecanoyl)-GLP-1(7-36);
Arg$^{26}$Lys$^{34}$(N$^\epsilon$-tetradecanoyl)-GLP-1(7-36);
Lys$^{26}$(N$^\epsilon$-tetradecanoyl)-GLP-1(7-35);
Lys$^{34}$(N$^\epsilon$-tetradecanoyl)-GLP-1(7-35);
Lys$^{26,34}$-bis(N$^\epsilon$-tetradecanoyl)-GLP-1(7-35);
Gly$^8$Lys$^{26}$(N$^\epsilon$-tetradecanoyl)-GLP-1(7-35);
Gly$^8$Lys$^{34}$(N$^\epsilon$-tetradecanoyl)-GLP-1(7-35);
Gly$^8$Lys$^{26,34}$-bis(N$^\epsilon$-tetradecanoyl)-GLP-1(7-35);
Arg$^{26}$Lys$^{34}$(N$^\epsilon$-tetradecanoyl)-GLP-1(7-35);
Lys$^{26}$(N$^\epsilon$-tetradecanoyl)-GLP-1(7-36)amide;
Lys$^{34}$(N$^\epsilon$-tetradecanoyl)-GLP-1(7-36)amide;
Lys$^{26,34}$-bis(N$^\epsilon$-tetradecanoyl)-GLP-1(7-36)amide;
Gly$^8$Lys$^{26}$(N$^\epsilon$-tetradecanoyl)-GLP-1(7-36)amide;
Gly$^8$Lys$^{34}$(N$^\epsilon$-tetradecanoyl)-GLP-1(7-36)amide;
Gly$^8$Lys$^{26,34}$-bis(N$^\epsilon$-tetradecanoyl)-GLP-1(7-36)amide;
Arg$^{26}$Lys$^{34}$(N$^\epsilon$-tetradecanoyl)-GLP-1(7-36)amide;
Gly$^8$Arg$^{26}$Lys$^{34}$(N$^\epsilon$-tetradecanoyl)-GLP-1(7-37);
Lys$^{26}$(N$^\epsilon$-tetradecanoyl)Arg$^{34}$-GLP-1(7-37);
Gly$^8$Lys$^{26}$(N$^\epsilon$-tetradecanoyl)Arg$^{34}$-GLP-1(7-37);
Arg$^{26,34}$Lys$^{36}$(N$^\epsilon$-tetradecanoyl)-GLP-1(7-37);
Gly$^8$Arg$^{26}$ 34Lys$^{36}$(N$^\epsilon$-tetradecanoyl)-GLP-1(7-37);
Gly$^8$Arg$^{26}$Lys$^{34}$(N$^\epsilon$-tetradecanoyl)-GLP-1(7-38);
Lys$^{26}$(N$^\epsilon$-tetradecanoyl)Arg$^{34}$-GLP-1(7-38);
Gly$^8$Lys$^{26}$(N$^\epsilon$-tetradecanoyl)Arg$^{34}$-GLP-1(7-38);
Arg$^{26}$ 34Lys$^{36}$(N$^\epsilon$-tetradecanoyl)-GLP-1(7-38);
Arg$^{26,34}$Lys$^{38}$(N$^\epsilon$-tetradecanoyl)-GLP-1(7-38);
Gly$^8$Arg$^{26,34}$Lys$^{36}$(N$^\epsilon$-tetradecanoyl)-GLP-1(7-38);
Gly$^8$Arg$^{26}$Lys$^{34}$(N$^\epsilon$-tetradecanoyl)-GLP-1(7-39);
Lys$^{26}$(N$^\epsilon$-tetradecanoyl)Arg$^{34}$-GLP-1(7-39);
Gly$^8$Lys$^{26}$(N$^\epsilon$-tetradecanoyl)Arg$^{34}$-GLP-1(7-39);
Arg$^{26,34}$Lys$^{36}$(N$^\epsilon$-tetradecanoyl)-GLP-1(7-39);
Gly$^8$Arg$^{26}$,34Lys$^{36}$(N$^\epsilon$-tetradecanoyl)-GLP-1(7-39);
Gly$^8$Arg$^{26}$Lys$^{34}$(N$^\epsilon$-tetradecanoyl)-GLP-1(7-40);
Lys$^{26}$(N$^\epsilon$-tetradecanoyl)Arg$^{34}$-GLP-1(7-40);
Gly$^8$Lys$^{26}$(N$^\epsilon$-tetradecanoyl)Arg$^{34}$-GLP-1(7-40);
Arg$^{26,34}$Lys$^{36}$(N$^\epsilon$-tetradecanoyl)-GLP-1(7-40);
Gly$^8$Arg$^{26,34}$Lys$^{36}$(N$^\epsilon$-tetradecanoyl)-GLP-1(7-40);
Lys$^{26}$(N$^\epsilon$-($\omega$-carboxynonadecanoyl))-GLP-1(7-37);
Lys$^{34}$(N$^\epsilon$-($\omega$-carboxynonadecanoyl))-GLP-1(7-37);

Lys$^{26,34}$-bis(N$^\epsilon$-(ω-carboxynonadecanoyl))-GLP-1(7-37);
Gly$^8$Lys$^{26}$(N$^\epsilon$-(ω-carboxynonadecanoyl))-GLP-1(7-37);
Gly$^8$Lys$^{34}$(N$^\epsilon$-(ω-carboxynonadecanoyl))-GLP-1(7-37);
Gly$^8$Lys$^{26,34}$-bis(N$^\epsilon$-(ω-carboxynonadecanoyl))-GLP-1(7-37);
Lys$^{26}$(N$^\epsilon$-(ω-carboxynonadecanoyl))-GLP-1(7-38);
Lys$^{34}$(N$^\epsilon$-(ω-carboxynonadecanoyl))-GLP-1(7-38);
Lys$^{26,34}$-bis(N$^\epsilon$-(ω-carboxynonadecanoyl))-GLP-1(7-38);
Gly$^8$Lys$^{26}$(N$^\epsilon$-(ω-carboxynonadecanoyl))-GLP-1(7-38);
Gly$^8$Lys$^{34}$(N$^\epsilon$-(ω-carboxynonadecanoyl))-GLP-1(7-38);
Gly$^8$Lys$^{26,34}$-bis(N$^\epsilon$-(ω-carboxynonadecanoyl))-GLP-1(7-38);
Lys$^{26}$(N$^\epsilon$-(ω-carboxynonadecanoyl))-GLP-1(7-39);
Lys$^{34}$(N$^\epsilon$-(ω-carboxynonadecanoyl))-GLP-1(7-39);
Lys$^{26,34}$-bis(N$^\epsilon$-(ω-carboxynonadecanoyl))-GLP-1(7-39);
Gly$^8$Lys$^{26}$(N$^\epsilon$-(ω-carboxynonadecanoyl))-GLP-1(7-39);
Gly$^8$Lys$^{34}$(N$^\epsilon$-(ω-carboxynonadecanoyl))-GLP-1(7-39);
Gly$^8$Lys$^{26,34}$-bis(N$^\epsilon$-(ω-carboxynonadecanoyl))-GLP-1(7-39);
Lys$^{26}$(N$^\epsilon$-(ω-carboxynonadecanoyl))-GLP-1(7-40);
Lys$^{34}$(N$^\epsilon$-(ω-carboxynonadecanoyl))-GLP-1(7-40);
Lys$^{26,34}$-bis(N$^\epsilon$-(ω-carboxynonadecanoyl))-GLP-1(7-40);
Gly$^8$Lys$^{26}$(N$^\epsilon$-α-carboxynonadecanoyl))-GLP-1(7-40);
Gly$^8$Lys$^{34}$(N$^\epsilon$-(ω-carboxynonadecanoyl))-GLP-1(7-40);
Gly$^8$Lys$^{26,34}$-bis(N$^\epsilon$-(ω-carboxynonadecanoyl))-GLP-1(7-40);
Lys$^{26}$(N$^\epsilon$-(ω-carboxynonadecanoyl))-GLP-1(7-36);
Lys$^{34}$(N$^\epsilon$-(ω-carboxynonadecanoyl))-GLP-1(7-36);
Lys$^{26,34}$-bis(N$^\epsilon$-(ω-carboxynonadecanoyl))-GLP-1(7-36);
Gly$^8$Lys$^{26}$(N$^\epsilon$-(ω-carboxynonadecanoyl))-GLP-1(7-36);
Gly$^8$Lys$^{34}$(N$^\epsilon$-(ω-carboxynonadecanoyl))-GLP-1(7-36);
Gly$^8$Lys$^{26,34}$-bis(N$^\epsilon$-(ω-carboxynonadecanoyl))-GLP-1(7-36);
Lys$^{26}$(N$^\epsilon$-(ω-carboxynonadecanoyl))-GLP-1(7-36)amide;
Lys$^{34}$(N$^\epsilon$-(ω-carboxynonadecanoyl))-GLP-1(7-36)amide;
Lys$^{26,34}$-bis(N$^\epsilon$-(ω-carboxynonadecanoyl))-GLP-1(7-36)amide;
Gly$^8$Lys$^{26}$(N$^\epsilon$-(ω-carboxynonadecanoyl))-GLP-1(7-36)amide;
Gly$^8$Lys$^{34}$(N$^\epsilon$-(ω-carboxynonadecanoyl))-GLP-1(7-36)amide;
Gly$^8$Lys$^{26,34}$-bis(N$^\epsilon$-(ω-carboxynonadecanoyl))-GLP-1(7-36)amide;
Lys$^{26}$(N$^\epsilon$-(ω-carboxynonadecanoyl))-GLP-1(7-35);
Lys$^{34}$(N$^{68}$-(ω-carboxynonadecanoyl))-GLP-1(7-35);
Lys$^{26,34}$-bis(N$^\epsilon$-(ω-carboxynonadecanoyl))-GLP-1(7-35);
Gly$^8$Lys$^{26}$(N$^\epsilon$-(ω-carboxynonadecanoyl))-GLP-1(7-35);
Gly$^8$Lys$^{34}$(N$^\epsilon$-(ω-carboxynonadecanoyl))-GLP-1(7-35);
Gly$^8$Lys$^{26,34}$-bis(N$^\epsilon$-(ω-carboxynonadecanoyl))-GLP-1(7-35);
Arg$^{26}$Lys$^{34}$ (N$^\epsilon$-ω-carboxynonadecanoyl))-GLP-1(7-37);
Gly$^8$Arg$^{26}$Lys$^{34}$(N$^\epsilon$-(ω-carboxynonadecanoyl))-GLP-1(7-37);
Lys$^{26}$(N$^\epsilon$-(ω-carboxynonadecanoyl))Arg$^{34}$-GLP-1(7-37);
Gly$^8$Lys$^{26}$(N$^\epsilon$-(ω-carboxynonadecanoyl))Arg$^{34}$-GLP-1(7-37);
Arg$^{26}$Lys$^{36}$(N$^\epsilon$-(ω-carboxynonadecanoyl))-GLP-1(7-37);
Gly$^8$Arg$^{26,34}$Lys$^{36}$(N$^\epsilon$-(ω-carboxynonadecanoyl))-GLP-1(7-37);
Arg$^{26}$Lys$^{34}$(N$^\epsilon$-(ω-carboxynonadecanoyl))-GLP-1(7-38);
Gly$^8$Arg$^{26}$Lys$^{34}$(N$^\epsilon$-(ω-carboxynonadecanoyl))-GLP-1(7-38);
Lys$^{26}$(N$^\epsilon$-(ω-carboxynonadecanoyl))Arg$^{34}$-GLP-1(7-38);
Gly$^8$Lys$^{26}$ (N$^\epsilon$-(ω-carboxynonadecanoyl))Arg$^{34}$-GLP-1(7-38);
Arg$^{26,34}$Lys$^{36}$(N$^\epsilon$-(ω-carboxynonadecanoyl))-GLP-1(7-38);
Arg$^{26,34}$Lys$^{38}$(N$^\epsilon$-(ω-carboxynonadecanoyl))-GLP-1(7-38);

Gly$^8$Arg$^{26,34}$Lys$^{36}$(N$^\epsilon$-(ω-carboxynonadecanoyl))-GLP-1(7-38);
Arg$^{26}$Lys$^{34}$(N$^\epsilon$-(ω-carboxynonadecanoyl))-GLP-1(7-39);
Gly$^8$Arg$^{26}$Lys$^{34}$(N$^\epsilon$-(ω-carboxynonadecanoyl))-GLP-1(7-39);
Lys$^{26}$(N$^\epsilon$-(ω-carboxynonadecanoyl))Arg$^{34}$-GLP-1(7-39);
Gly$^8$Lys$^{26}$(N$^\epsilon$-(ω-carboxynonadecanoyl))Arg$^{34}$-GLP-1(7-39);
Arg$^{26,34}$Lys$^{36}$(N$^\epsilon$-(ω-carboxynonadecanoyl))-GLP-1(7-39);
Gly$^8$Arg$^{26,34}$Lys$^{36}$ (N$^\epsilon$-(ω-carboxynonadecanoyl))-GLP-1(7-39);
Arg$^{26}$Lys$^{34}$ (N$^\epsilon$-(ω-carboxynonadecanoyl))-GLP-1(7-40);
Gly$^8$Arg$^{26}$Lys$^{34}$(N$^\epsilon$-(ω-carboxynonadecanoyl))-GLP-1(7-40);
Lys$^{26}$(N$^\epsilon$-(ω-carboxynonadecanoyl))Arg$^{34}$-GLP-1(7-40);
Gly$^8$Lys$^{26}$(N$^\epsilon$-(ω-carboxynonadecanoyl))Arg$^{34}$-GLP-1(7-40);
Arg$^{26,34}$Lys$^{36}$(N$^\epsilon$-(ω-carboxynonadecanoyl))-GLP-1(7-40);
Gly$^8$Arg$^{26,34}$Lys$^{36}$(N$^\epsilon$-(ω-carboxynonadecanoyl))-GLP-1(7-40);
Lys$^{26}$(N$^\epsilon$-(7-deoxycholoyl))-GLP-1(7-37);
Lys$^{34}$(N$^\epsilon$-(7-deoxycholoyl))-GLP-1(7-37);
Lys$^{26,34}$-bis(N$^\epsilon$-(7-deoxycholoyl))-GLP-1(7-37);
Gly$^8$Lys$^{26}$(N$^\epsilon$-(7-deoxycholoyl))-GLP-1(7-37);
Gly$^8$Lys$^{34}$(N$^\epsilon$-(7-deoxycholoyl))-GLP-1(7-37);
Gly$^8$Lys$^{26,34}$-bis(N$^\epsilon$-(7-deoxycholoyl))-GLP-1(7-37);
Arg$^{26}$Lys$^{34}$(N$^\epsilon$-(7-deoxycholoyl))-GLP-1(7-37);
Lys$^{26}$(N$^\epsilon$-(7-deoxycholoyl))-GLP-1(7-38);
Lys$^{34}$(N$^\epsilon$-(7-deoxycholoyl))-GLP-1(7-38);
Lys$^{26,34}$-bis(N$^\epsilon$-(7-deoxycholoyl))-GLP-1(7-38);
Gly$^8$Lys$^{26}$(N$^\epsilon$-(7-deoxycholoyl))-GLP-1(7-38);
Gly$^8$Lys$^{34}$(N$^\epsilon$-(7-deoxycholoyl))-GLP-1(7-38);
Gly$^8$Lys$^{26,34}$-bis(N$^\epsilon$-(7-deoxycholoyl))-GLP-1(7-38);
Arg$^{26}$Lys$^{34}$(N$^\epsilon$-(7-deoxycholoyl))-GLP-1(7-38);
Lys$^{26}$(N$^\epsilon$-(7-deoxycholoyl))-GLP-1(7-39);
Lys$^{34}$(N$^\epsilon$-(7-deoxycholoyl))-GLP-1(7-39);
Lys$^{26,34}$-bis(N$^\epsilon$-(7-deoxycholoyl))-GLP-1(7-39);
Gly$^8$Lys$^{26}$(N$^\epsilon$-(7-deoxycholoyl))-GLP-1(7-39);
Gly$^8$Lys$^{34}$(N$^\epsilon$-(7-deoxycholoyl))-GLP-1(7-39);
Gly$^8$Lys$^{26,34}$-bis(N$^\epsilon$-(7-deoxycholoyl))-GLP-1(7-39);
Arg$^{26}$Lys$^{34}$(N$^\epsilon$-(7-deoxycholoyl))-GLP-1(7-39);
Lys$^{26}$(N$^\epsilon$-(7-deoxycholoyl))-GLP-1(7-40);
Lys$^{34}$(N$^\epsilon$-(7-deoxycholoyl))-GLP-1(7-40);
Lys$^{26,34}$-bis(N$^\epsilon$-(7-deoxycholoyl))-GLP-1(7-40);
Gly$^8$Lys$^{26}$(N$^\epsilon$-(7-deoxycholoyl))-GLP-1(740);
Gly$^8$Lys$^{34}$(N$^\epsilon$-(7-deoxycholoyl))-GLP-1(7-40);
Gly$^8$Lys$^{26,34}$-bis(N$^\epsilon$-(7-deoxycholoyl))-GLP-1(7-40);
Arg$^{26}$Lys$^{34}$(N 1-(7-deoxycholoyl))-GLP-1(7-40);
Lys$^{26}$(N$^\epsilon$-(7-deoxycholoyl))-GLP-1(7-36);
Lys$^{34}$(N$^\epsilon$-(7-deoxycholoyl))-GLP-1(7-36);
Lys$^{26,34}$-bis(N$^\epsilon$-(7-deoxycholoyl))-GLP-1(7-36);
Gly$^8$Lys$^{26}$(N$^\epsilon$-(7-deoxycholoyl))-GLP-1(7-36);
Gly$^8$Lys$^{34}$(N$^\epsilon$-(7-deoxycholoyl))-GLP-1(7-36);
Gly$^8$Lys$^{26,34}$-bis(N$^\epsilon$-(7-deoxycholoyl))-GLP-1(7-36);
Arg$^{26}$Lys$^{34}$(N$^\epsilon$-(7-deoxycholoyl))-GLP-1(7-36);
Lys$^{26}$(N$^\epsilon$-(7-deoxycholoyl))-GLP-1(7-35);
Lys$^{34}$(N$^\epsilon$-(7-deoxycholoyl))-GLP-1(7-35);
Lys$^{26,34}$-bis(N$^\epsilon$-(7-deoxycholoyl))-GLP-1(7-35);
Gly$^8$Lys$^{26}$(N$^\epsilon$-(7-deoxycholoyl))-GLP-1(7-35);
Gly$^8$Lys$^{34}$(N$^\epsilon$-(7-deoxycholoyl))-GLP-1(7-35);
Gly$^8$Lys$^{26,34}$-bis(N$^\epsilon$-(7-deoxycholoyl))-GLP-1(7-35);
Arg$^{26}$Lys$^{34}$(N$^\epsilon$-(7-deoxycholoyl))-GLP-1(7-35);
Lys$^{26}$(N$^\epsilon$-(7-deoxycholoyl))-GLP-1(7-36)amide;
Lys$^{34}$(N$^\epsilon$-(7-deoxycholoyl))-GLP-1(7-36)amide;
Lys$^{26,34}$-bis(N$^\epsilon$-(7-deoxycholoyl))-GLP-1(7-36)amide;
Gly$^8$Lys$^{26}$(N$^\epsilon$-(7-deoxycholoyl))-GLP-1(7-36)amide;
Gly$^8$Lys$^{34}$(N$^\epsilon$-(7-deoxycholoyl))-GLP-1(7-36)amide;

Gly⁸Lys²⁶,³⁴-bis(Nᵋ-(7-deoxycholoyl))-GLP-1(7-36)amide;
Arg²⁶Lys³⁴(Nᵋ-(7-deoxycholoyl))-GLP-1(7-36)amide;
Gly⁸Arg²⁶Lys³⁴(Nᵋ-(7-deoxycholoyl))-GLP-1(7-37);
Lys²⁶(Nᵋ-(7-deoxycholoyl))Arg³⁴-GLP-1(7-37);
Gly⁸Lys²⁶(Nᵋ-(7-deoxycholoyl))Arg³⁴-GLP-1(7-37);
Arg²⁶,³⁴Lys³⁶(Nᵋ-(7-deoxycholoyl))-GLP-1(7-37);
Gly⁸Arg²⁶,³⁴Lys³⁶(Nᵋ-(7-deoxycholoyl))-GLP-1(7-37);
Lys²⁶(Nᵋ-(choloyl))-GLP-1(7-37);
Lys³⁴(Nᵋ-(choloyl))-GLP-1(7-37);
Lys²⁶,³⁴-bis(Nᵋ-(choloyl))-GLP-1(7-37);
Gly⁸Lys²⁶(Nᵋ-(choloyl))-GLP-1(7-37);
Gly⁸Lys³⁴(Nᵋ-(Choloyl))-GLP-1(7-37);
Gly⁸Lys²⁶,³⁴-bis(Nᵋ-(choloyl))-GLP-1(7-37);
Arg²⁶Lys³⁴(Nᵋ-(choloyl))-GLP-1(7-37);
Gly⁸Arg²⁶Lys³⁴(Nᵋ-(7-deoxycholoyl))-GLP-1(7-38);
Lys²⁶(Nᵋ-(7-deoxycholoyl))Arg³⁴-GLP-1(7-38);
Gly⁸Lys²⁶(Nᵋ-(7-deoxycholoyl))Arg³⁴-GLP-1(7-38);
Arg²⁶,³⁴Lys³⁶(Nᵋ-(7-deoxycholoyl))-GLP-1(7-38);
Arg²⁶,³⁴Lys³⁸(Nᵋ-(7-deoxycholoyl))-GLP-1(7-38);
Gly⁸Arg²⁶,³⁴Lys³⁶(Nᵋ-(7-deoxycholoyl))-GLP-1(7-38);
Lys²⁶(Nᵋ-(choloyl))-GLP-1(7-38);
Lys³⁴(Nᵋ-(choloyl))-GLP-1(7-38);
Lys²⁶,³⁴-bis(Nᵋ-(choloyl))-GLP-1(7-38);
Gly⁸Lys²⁶(Nᵋ-(choloyl))-GLP-1(7-38);
Gly⁸Lys³⁴(Nᵋ-(choloyl))-GLP-1(7-38);
Gly⁸Lys²⁶,³⁴-bis(Nᵋ-(choloyl))-GLP-1(7-38);
Arg²⁶Lys³⁴(Nᵋ-(choloyl))-GLP-1(7-38);
Gly⁸Arg²⁶Lys³⁴(Nᵋ-(7-deoxycholoyl))-GLP-1(7-39);
Lys²⁶(Nᵋ-(7-deoxycholoyl))Arg³⁴-GLP-1(7-39);
Gly⁸Lys²⁶(Nᵋ-(7-deoxycholoyl))Arg³⁴-GLP-1(7-39);
Arg²⁶,³⁴Lys³⁶(Nᵋ-(7-deoxycholoyl))-GLP-1(7-39);
Gly⁸Arg²⁶,³⁴Lys³⁶(Nᵋ-(7-deoxycholoyl))-GLP-1(7-39);
Lys²⁶(Nᵋ-(choloyl))-GLP-1(7-39);
Lys³⁴(Nᵋ-(choloyl))-GLP-1(7-39);
Lys²⁶,³⁴-bis(Nᵋ-(choloyl))-GLP-1(7-39);
Gly⁸Lys²⁶(Nᵋ-(choloyl))-GLP-1(7-39);
Gly⁸Lys³⁴(Nᵋ-(choloyl))-GLP-1(7-39);
Gly⁸Lys²⁶,³⁴-bis(Nᵋ-(choloyl))-GLP-1(7-39);
Arg²⁶Lys³⁴(Nᵋ-(choloyl))-GLP-1(7-39);
Gly⁸Arg²⁶Lys³⁴(Nᵋ-(7-deoxycholoyl))-GLP-1(7-40);
Lys²⁶(Nᵋ-(7-deoxycholoyl))Arg³⁴-GLP-1(7-40);
Gly⁸Lys²⁶(Nᵋ-(7-deoxycholoyl))Arg³⁴-GLP-1(7-40);
Arg²⁶,³⁴Lys³⁶(Nᵋ-(7-deoxycholoyl))-GLP-1(7-40);
Gly⁸Arg²⁶,³⁴Lys³⁶(Nᵋ-(7-deoxycholoyl))-GLP-1(7-40);
Lys²⁶(Nᵋ-(choloyl))-GLP-1(7-40);
Lys³⁴(Nᵋ-(choloyl))-GLP-1(7-40);
Lys²⁶,³⁴-bis(Nᵋ-(choloyl))-GLP-1(7-40);
Gly⁸Lys²⁶(Nᵋ-(choloyl))-GLP-1(7-40);
Gly⁸Lys³⁴(Nᵋ-(choloyl))-GLP-1(7-40);
Gly⁸Lys²⁶,³⁴-bis(Nᵋ-(choloyl))-GLP-1(7-40);
Arg²⁶Lys³⁴(Nᵋ-(choloyl))-GLP-1(7-40);
Lys²⁶(Nᵋ-(choloyl))-GLP-1(7-36);
Lys³⁴(Nᵋ-(choloyl))-GLP-1(7-36);
Lys²⁶,³⁴-bis(Nᵋ-(choloyl))-GLP-1(7-36);
Gly⁸Lys²⁶(Nᵋ-(choloyl))-GLP-1(7-36);
Gly⁸Lys³⁴(Nᵋ-(choloyl))-GLP-1(7-36);
Gly⁸Lys²⁶,³⁴-bis(Nᵋ-(choloyl))-GLP-1(7-36);
Arg²⁶Lys³⁴(Nᵋ-(choloyl))-GLP-1(7-36);
Lys²⁶(Nᵋ-(choloyl))-GLP-1(7-35);
Lys³⁴(Nᵋ-(choloyl))-GLP-1(7-35);
Lys²⁶,³⁴-bis(Nᵋ-(choloyl))-GLP-1(7-35);
Gly⁸Lys²⁶(Nᵋ-(choloyl))-GLP-1(7-35);
Gly⁸Lys³⁴(Nᵋ-(choloyl))-GLP-1(7-35);
Gly⁸Lys²⁶ 34-bis(Nᵋ-(choloyl))-GLP-1(7-35);
Arg²⁶Lys³⁴(Nᵋ-(choloyl))-GLP-1(7-35);
Lys²⁶(Nᵋ-(choloyl))-GLP-1(7-36)amide;
Lys³⁴(Nᵋ-(choloyl))-GLP-1(7-36)amide;
Lys²⁶,³⁴-bis(Nᵋ-(choloyl))-GLP-1(7-36)amide;
Gly⁸Lys²⁶(Nᵋ-(choloyl))-GLP-1(7-36)amide;
Gly⁸Lys³⁴(Nᵋ-(choloyl))-GLP-1(7-36)amide;
Gly⁸Lys²⁶,³⁴-bis(Nᵋ-(choloyl))-GLP-1(7-36)amide;
Arg²⁶Lys³⁴(Nᵋ-(choloyl))-GLP-1(7-36)amide;
Gly⁸Arg²⁶Lys³⁴(Nᵋ-(choloyl))-GLP-1(7-37);
Lys²⁶(Nᵋ(choloyl))Arg³⁴-GLP-1(7-37);
Gly⁸Lys²⁶(Nᵋ(choloyl))Arg³⁴-GLP-1(7-37);
Arg²⁶,³⁴Lys³⁶(Nᵋ-(choloyl))-GLP-1(7-37);
Gly⁸Arg²⁶,³⁴Lys³⁶(Nᵋ-(choloyl))-GLP-1(7-37);
Lys²⁶(Nᵋ-(lithocholoyl))-GLP-1(7-37);
Lys³⁴(Nᵋ-(lithocholoyl))-GLP-1(7-37);
Lys²⁶,³⁴-bis(Nᵋ-(lithocholoyl))-GLP-1(7-37);
Gly⁸Lys²⁶(Nᵋ-(lithocholoyl))-GLP-1(7-37);
Gly⁸Lys³⁴(Nᵋ-(lithocholoyl))-GLP-1(7-37);
Gly⁸Lys²⁶,³⁴-bis(Nᵋ-(lithocholoyl))-GLP-1(7-37);
Arg²⁶Lys³⁴(Nᵋ-(lithocholoyl))-GLP-1(7-37);
Gly⁸Arg²⁶Lys³⁴(Nᵋ-(choloyl))-GLP-1 (7-38);
Lys²⁶(Nᵋ-(choloyl))Arg³⁴-GLP-1(7-38);
Gly⁸Lys²⁶(Nᵋ-(choloyl))Arg³⁴-GLP-1(7-38);
Arg²⁶,³⁴Lys³⁶(Nᵋ-(choloyl))-GLP-1 (7-38);
Arg²⁶,³⁴Lys³⁸(Nᵋ-(choloyl))-GLP-1(7-38);
Gly⁸Arg²⁶,³⁴Lys³⁶(Nᵋ-(choloyl))-GLP-1(7-38);
Lys²⁶(Nᵋ-(lithocholoyl))-GLP-1(7-38);
Lys³⁴(Nᵋ-(lithocholoyl))-GLP-1(7-38);
Lys²⁶,³⁴-bis(Nᵋ-(lithocholoyl))-GLP-1(7-38);
Gly⁸Lys²⁶(Nᵋ-(lithocholoyl))-GLP-1(7-38);
Gly⁸Lys³⁴(Nᵋ-(lithocholoyl))-GLP-1(7-38);
Gly⁸Lys²⁶,³⁴-bis(Nᵋ-(lithocholoyl))-GLP-1(7-38);
Arg²⁶Lys³⁴(Nᵋ-(lithocholoyl))-GLP-1(7-38);
Gly⁸Arg²⁶Lys³⁴(Nᵋ-(choloyl))-GLP-1(7-39);
Lys²⁶(Nᵋ-(choloyl))Arg³⁴-GLP-1(7-39);
Gly⁸Lys²⁶(Nᵋ-(choloyl))Arg³⁴-GLP-1 (7-39);
Arg²⁶,³⁴Lys³⁶(Nᵋ-(choloyl))-GLP-1 (7-39);
Gly⁸Arg²⁶,³⁴Lys³⁶(Nᵋ-(choloyl))-GLP-1(7-39);
Lys²⁶(Nᵋ-(lithocholoyl))-GLP-1(7-39);
Lys³⁴(Nᵋ-(lithocholoyl))-GLP-1(7-39);
Lys²⁶,³⁴-bis(Nᵋ-(lithocholoyl))-GLP-1(7-39);
Gly⁸Lys²⁶(Nᵋ-(lithocholoyl))-GLP-1(7-39);
Gly⁸Lys³⁴(Nᵋ-(lithocholoyl))-GLP-1(7-39);
Gly⁸Lys²⁶,³⁴-bis(Nᵋ-(lithocholoyl))-GLP-1(7-39);
Arg²⁶Lys³⁴(Nᵋ-(lithocholoyl))-GLP-1(7-39);
Gly⁸Arg²⁶Lys³⁴(Nᵋ-(choloyl))-GLP-1(7-40);
Lys²⁶(Nᵋ-(choloyl))Arg³⁴-GLP-1(7-40);
Gly⁸Lys²⁶(Nᵋ-(choloyl))Arg³⁴-GLP 1(7-40);
Arg²⁶,³⁴Lys³⁶(Nᵋ-(choloyl))-GLP-1(7-40);
Gly⁸Arg²⁶,³⁴Lys³⁶(Nᵋ-(choloyl))-GLP-1(7-40);
Lys²⁶(Nᵋ-(lithocholoyl))-GLP-1(7-40);
Lys³⁴(Nᵋ-(lithocholoyl))-GLP-1(7-40);
Lys²⁶,³⁴-bis(Nᵋ-(lithocholoyl))-GLP-1(7-40);
Gly⁸Lys²⁶(Nᵋ-(lithocholoyl))-GLP-1(7-40);
Gly⁸Lys³⁴(Nᵋ-(lithocholoyl))-GLP-1(7-40);
Gly⁸Lys²⁶,³⁴-bis(Nᵋ-(lithocholoyl))-GLP-1(7-40);
Arg²⁶Lys³⁴(Nᵋ-(lithocholoyl))-GLP-1(7-37);
Lys²⁶(Nᵋ-(lithocholoyl))-GLP-1(7-36);
Lys³⁴(Nᵋ-(lithocholoyl))-GLP-1(7-36);
Lys²⁶,³⁴-bis(Nᵋ-(lithocholoyl))-GLP-1(7-36);
Gly⁸Lys²⁶(Nᵋ-(lithocholoyl))-GLP-1(7-36);
Gly⁸Lys³⁴(Nᵋ-(lithocholoyl))-GLP-1(7-36);
Gly⁸Lys²⁶,³⁴-bis(Nᵋ-(lithocholoyl))-GLP-1(7-36);
Arg²⁶Lys³⁴(Nᵋ-(lithocholoyl))-GLP-1(7-36);
Lys²⁶(Nᵋ-(lithocholoyl))-GLP-1(7-35);
Lys³⁴(Nᵋ-(lithocholoyl))-GLP-1(7-35);
Lys²⁶,³⁴-bis(Nᵋ-(lithocholoyl))-GLP-1(7-35);
Gly⁸Lys²⁶(Nᵋ-(lithocholoyl))-GLP-1(7-35);
Gly⁸Lys³⁴(Nᵋ-(lithocholoyl))-GLP-1(7-35);
Gly⁸Lys²⁶,³⁴-bis(Nᵋ-(lithocholoyl))-GLP-1(7-35);

Arg$^{26}$Lys$^{34}$(N$^\epsilon$-(lithocholoyl))-GLP-1(7-35);
Lys$^{26}$(N$^\epsilon$-(lithocholoyl))-GLP-1(7-36)amide;
Lys$^{34}$(N$^\epsilon$-(lithocholoyl))-GLP-1(7-36)amide;
Lys$^{26,34}$-bis(N$^\epsilon$-(lithocholoyl))-GLP-1(7-36)amide;
Gly$^8$Lys$^{26}$(N$^\epsilon$-(lithocholoyl))-GLP-1(7-36)amide;
Gly$^8$Lys$^{34}$(N$^\epsilon$-(lithocholoyl))-GLP-1(7-36)amide;
Gly$^8$Lys$^{26,34}$-bis(N$^\epsilon$-(lithocholoyl))-GLP-1(7-36)amide;
Arg$^{26}$Lys$^{34}$(N$^\epsilon$-(lithocholoyl))-GLP-1(7-36)amide;
Gly$^8$Arg$^{26}$Lys$^{34}$(N$^\epsilon$-(lithocholoyl))-GLP-1(7-37);
Lys$^{26}$(N$^\epsilon$-(lithocholoyl))Arg$^{34}$-GLP-1(7-37);
Gly$^8$Lys$^{26}$(N$^\epsilon$-(lithocholoyl))Arg$^{34}$-GLP-1(7-37);
Arg$^{26,34}$Lys$^{36}$(N$^\epsilon$-(lithocholoyl))-GLP-1(7-37);
Arg$^{26,34}$Lys$^{38}$(N$^\epsilon$-(lithocholoyl))-GLP-1(7-37);
Gly$^8$Arg$^{26,34}$Lys$^{36}$(N$^\epsilon$-(lithocholoyl))-GLP-1(7-37);
Gly$^8$Arg$^{26}$Lys$^{34}$(N$^\epsilon$-(lithocholoyl))-GLP-1(7-38);
Lys$^{26}$(N$^\epsilon$-(lithocholoyl))Arg$^{34}$-GLP-1(7-38);
Gly$^8$Lys$^{26}$(N$^\epsilon$-(lithocholoyl))Arg$^{34}$-GLP-1(7-38);
Arg$^{26,34}$Lys$^{36}$(N$^\epsilon$-(lithocholoyl))-GLP-1(7-38);
Arg$^{26,34}$Lys$^{38}$(N$^\epsilon$-(lithocholoyl))-GLP-1(7-38);
Gly$^8$Arg$^{26,34}$Lys$^{36}$(N$^\epsilon$-(lithocholoyl))-GLP-1(7-38);
Gly$^8$Arg$^{26}$Lys$^{34}$(N$^\epsilon$-(lithocholoyl))-GLP-1(7-39);
Lys$^{26}$(N$^\epsilon$-(lithocholoyl))Arg$^{34}$-GLP-1(7-39);
Gly$^8$Lys$^{26}$(N$^\epsilon$-(lithocholoyl))Arg$^{34}$-GLP-1(7-39);
Arg$^{26,34}$Lys$^{36}$ (N$^\epsilon$-(lithocholoyl))-GLP-1(7-39);
Gly$^8$Arg$^{26,34}$Lys$^{36}$(N$^\epsilon$-(lithocholoyl))-GLP-1(7-39);
Gly$^8$Arg$^{26}$Lys$^{34}$(N$^\epsilon$-(lithocholoyl))-GLP-1(7-40);
Lys$^{26,34}$(N$^\epsilon$-(lithocholoyl))Arg$^{34}$-GLP-1(7-40);
Gly$^8$Lys$^{26}$(N$^\epsilon$-(lithocholoyl))Arg$^{34}$-GLP-1(7-40);
Arg$^{26,34}$Lys$^{36}$(N$^\epsilon$-(lithocholoyl))-GLP-1(7-40) and
Gly$^8$Arg$^{26,34}$Lys$^{36}$(N$^\epsilon$-(lithocholoyl))-GLP-1(7-40).

Another object of the present invention provides a combination therapy pharmaceutical composition comprising a GLP-1 derivative wherein the GLP-1 derivative is Arg$^{34}$-GLP-1(7-37), wherein
(a) the ε-amino group of Lys at position 26 is substituted with a lipophilic substituent optionally via a spacer, and
(b) the lipophilic substituent is (i) CH$_3$(CH$_2$)$_n$CO— wherein n is 6, 8, 10, 12, 14, 16, 18, 20 or 22, (ii) HOOC(CH$_2$)$_m$CO— wherein m is 10, 12, 14, 16, 18, 20 or 22, or (iii) lithocholyl, and when present, the spacer is an amino acid residue except Cys, or the spacer is γ-aminobutanoyl.

Another object of the present invention provides a combination therapy pharmaceutical composition comprising a GLP-1 derivative, wherein the lipophilic substituent is linked to the ε-amino group of Lys via a spacer.

Another object of the present invention provides a combination therapy pharmaceutical composition comprising a GLP-1 derivative, wherein the spacer is selected from the group: γ-glutamyl, β-asparagyl, glycyl, and β-alanyl.

Another object of the present invention provides a combination therapy pharmaceutical composition comprising a GLP-1 derivative wherein the GLP-1 derivative is selected from the following:
Lys$^{26}$(N$^\epsilon$-tetradecanoyl)-GLP-1(7-37),
Arg$^{34}$Lys$^{26}$(N$^\epsilon$-lithocholyl)-GLP-1(7-37)-OH,
Arg$^{34}$Lys$^{26}$(N$^\epsilon$-(γ-glutamyl(N$^\alpha$-hexadecanoyl)))-GLP-1(7-37)-OH, and
Arg$^{34}$Lys$^{26}$(N$^\epsilon$-(γ-glutamyl(N$^\alpha$-tetradecanoyl)))-GLP-1(7-37)-OH.

Another object of the present invention provides a combination therapy pharmaceutical composition wherein the dual PPAR-α/PPAR-γ activator is a compound of formula (I) together with a pharmaceutically acceptable carrier or diluent.

Another object of the present invention provides a combination therapy pharmaceutical composition wherein the GLP-1 derivative comprises a sequence wherein at least one amino acid residue of the sequence has a lipophilic substituent attached, with the proviso that if only one lipophilic substituent is present and this substituent is attached to the N-terminal or to the C-terminal amino acid residue of the parent peptide then this substituent is an alkyl group or a group which has an ω-carboxylic acid group, together with a pharmaceutically acceptable carrier or diluent.

Another object of the present invention provides a combination therapy pharmaceutical composition in unit dosage form, comprising from about 0.05 to about 100 mg, preferably from about 0.1 to about 50 mg of the compound according to any one of the preceding compound claims or a pharmaceutically acceptable salt thereof.

Another object of the present invention provides a process for making a pharmaceutical composition comprising combining a GLP-1 derivative and a dual PPAR-α/PPAR-γ activator and a pharmaceutically acceptable carrier.

Another object of the present invention provides a method of treating or preventing disorders or diseases mediated by nuclear receptors, comprising administering to a patient in need of such treatment a therapeutically effective amount of the combination therapy pharmaceutical composition.

Another object of the present invention provides a method of treating or preventing metabolic disorders or diseases mediated by the PPARs, comprising administering to a patient in need of such treatment a therapeutically effective amount of the combination therapy pharmaceutical composition.

Another object of the present invention provides a method of treating or preventing metabolic syndrome, diabetes and/or obesity, comprising administering to a patient in need of such treatment a therapeutically effective amount of the combination therapy pharmaceutical composition or a pharmaceutically acceptable salt thereof together with a pharmaceutically acceptable carrier or diluent.

Another object of the present invention provides a combination therapy pharmaceutical composition for oral, nasal, transdermal, pulmonal, or parenteral administration.

Another object of the present invention provides a kit comprising an amount of a GLP-1 derivative and a pharmaceutically acceptable carrier, vehicle, or diluent in a first unit dosage form; an amount of a dual PPAR-α/PPAR-γ activator and a pharmaceutically acceptable carrier, vehicle, or diluent in a second unit dosage form; and a container.

Another object of the present invention provides a method for treating or preventing diseases or disorders involving the metabolic syndrome, insulin resistance, dyslipidemia, obesity, diabetes, hypertriglyceridaemia, impaired glucose tolerance or hypertension, said method comprising administering to a patient in need of said treatment (i) a first amount of a GLP-1 derivative and (ii) a second amount of a dual PPAR-α/PPAR-γ activator, wherein said first and second amounts together are effective for said treatment.

In the above structural formulas and throughout the present specification, the following terms have the indicated meaning:

The term "C$_{1-12}$-alkyl" as used herein, alone or in combination is intended to include those alkyl groups of the designated length in either a linear or branched or cyclic configuration represents e.g. cyclopropyl, cyclobutyl, cyclopentyl, cyclohexyl, cycloheptyl and cyclooctyl and the like. Typical C$_{1-12}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl and the like, especially preferred is methyl and ethyl.

The term "$C_{2-12}$-alkenyl" as used herein, represents an olefinically unsaturated branched or straight group having from 2 to the specified number of carbon atoms and at least one double bond. Examples of such groups include, but are not limited to, vinyl, 1-propenyl, 2-propenyl, allyl, isoproppenyl, 1,3-butadienyl, 1-butenyl, hexenyl, pentenyl and the like, especially preferred is vinyl and 1-propenyl.

The term "$C_{2-12}$-alkynyl" as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like especially preferred is 1-propynyl.

The term "$C_{4-12}$-alkenynyl" as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like, especially preferred is 1-pentene-4-yne.

The term "$C_{1-6}$-alkoxy" as used herein, alone or in combination is intended to include those $C_{1-6}$-alkyl groups of the designated length in either a linear or branched or cyclic configuration linked thorugh an ether oxygen having its free valence bond from the ether oxygen. Examples of linear alkoxy groups are methoxy, ethoxy, propoxy, butoxy, pentoxy, hexoxy and the like especially preferred is methoxy and ethoxy. Examples of branched alkoxy are isopropoxy, sec-butoxy, tert-butoxy, isopentoxy, isohexoxy and the like especially preferred is isopropoxy. Examples of cyclic alkoxy are cyclopropyloxy, cyclobutyloxy, cyclopentyloxy, cyclohexyloxy and the like, especially preferred is cyclopropoxy.

The term "$C_{1-6}$-alkylthio" as used herein, alone or in combination, refers to a straight or branched or cyclic monovalent substituent comprising a $C_{1-6}$alkyl group linked through a divalent sulfur atom having its free valence bond from the sulfur atom and having 1 to 6 carbon atoms e.g. methylthio, ethylthio, propylthio, butylthio, pentylthio and the like. Examples of cyclic alkylthio are cyclopropylthio, cyclobutylthio, cyclopentylthio, cyclohexylthio and the like.

The term "$C_{1-6}$-alkylamino" as used herein, alone or in combination, refers to a straight or branched or cyclic monovalent substituent comprising a $C_{1-6}$-alkyl group linked through amino having a free valence bond from the nitrogen atom e.g. methylamino, ethylamino, propylamino, butylamino, pentylamino and the like. Examples of cyclic alkylamino are cyclopropylamino, cyclobutylamino, cyclopentylamino, cyclohexylamino and the like.

The term "$C_{1-6}$-alkoxy$C_{1-6}$-alkyl" as used herein, alone or in combination, refers to a $C_{1-6}$-alkyl as defined herein whereto is attached a $C_{1-6}$-alkoxy as defined herein, e.g. methoxymethyl, ethoxymethyl, methoxyethyl, ethoxyethyl and the like.

The term "aryl" is intended to include aromatic rings, such as carbocyclic aromatic rings selected from the group consisting of phenyl, naphthyl, (1-naphthyl or 2-naphthyl) and the like optionally substituted with halogen, amino, hydroxy, $C_{1-6}$-alkyl, $C_{1-6}$-alkoxy, $C_{1-6}$-alkylester or carboxy and the like, especially preferred is phenyl and naphtyl optionally substituted with halogen.

The term "arylene" is intended to include divalent aromatic rings, such as carbocyclic aromatic rings selected from the group consisting of phenylene, naphthylene and the like optionally substituted with halogen, amino, hydroxy, $C_{1-6}$-alkyl, $C_{1-6}$-alkoxy, $C_{1-6}$-alkylester or carboxy and the like, especially preferred is phenylene.

The term "halogen" means fluorine, chlorine, bromine or iodine especially preferred is chlorine The term "perhalomethyl" means trifluoromethyl, trichloromethyl, tribromomethyl or triiodomethyl, especially preferred is trifluoromethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl)amino and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl and the like.

The term "heteroaryl" as used herein, alone or in combination, refers to a monovalent substituent comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like especially preferred is furan, pyrrole, pyridine, indole and benzofuran.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine and the like, especially preferred is furan, pyrrole, pyridine, indole and benzofuran.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen, and the like.

The term "aralkyl" as used herein refers to a straight or branched saturated carbon chain containing from 1 to 6 carbons substituted with an aromatic carbohydride; such as benzyl, phenethyl, 3-phenylpropyl, 1-naphthylmethyl, 2-(1-naphthyl)ethyl and the like, especially preferred is benzyl.

The term "aryloxy" as used herein refers to phenoxy, 1-naphthyloxy, 2-naphthyloxy and the like especially preferred is phenoxy. The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl)ethoxy and the like, especially preferred is benzyloxy.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl)ethyl and the like.

The term "heteroaralkoxy" as used herein refers to a heteroarylalkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)-thio, (2-chlorophenyl)thio and the like.

As used herein, the phrase "heterocyclyl" means a monovalent saturated or unsaturated non aromatic group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline and the like); 5-membered heterocycles having two heteroatoms in 1, 2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g. pyrrolidine, pyrroline and the like); 5-membered heterocycles having two heteroatoms in 1, 2 or 1,3 positions (e.g. pyrazoline, pyrazolidine, 1,2-oxathiolane, imidazolidine, imidazoline, 4-oxazolone and the like); 5-membered heterocycles having three heteroatoms (e.g. tetrahydrofurazan and the like); 5-membered heterocycles having four heteroatoms; 6-membered heterocycles with one heteroatom (e.g. piperidine and the like); 6-membered heterocycles with two heteroatoms (e.g. piperazine, morpholine and the like); 6-membered heterocycles with three heteroatoms; and 6-membered heterocycles with four heteroatoms, and the like.

As used herein the term "treatment" includes treatment, prevention and management of such condition.

Certain of the above defined terms may occur more than once in the above formula (I), and upon such occurrence each term shall be defined independently of the other.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

Furthermore, the present compounds can be utilised in the treatment and/or prevention of conditions mediated by nuclear receptors, in particular the Peroxisome Proliferator-Activated Receptors (PPAR).

In a further aspect, the present invention relates to a method of treating and/or preventing Type I or Type II diabetes.

In a still further aspect, the present invention relates to the use of one or more compounds of the invention or pharmaceutically acceptable salts thereof for the preparation of a medicament for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds comprising the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

Human GLP-1 is a 37 amino acid residue peptide originating from preproglucagon which is synthesised i.a. in the L-cells in the distal ileum, in the pancreas and in the brain. Processing of preproglucagon to give GLP-1(7-36)amide, GLP-1(7-37) and GLP-2 occurs mainly in the L-cells. A simple system is used to describe fragments and analogues of this peptide. Thus, for example, $Gly^8$-GLP-1(7-37) designates a fragment of GLP-1 formally derived from GLP-1 by deleting the amino acid residues Nos. 1 to 6 and substituting the naturally occurring amino acid residue in position 8 (Ala) by Gly. Similarly, $Lys^{34}(N^\epsilon$-tetradecanoyl)-GLP-1 (7-37) designates GLP-1(7-37) wherein the E-amino group of the Lys residue in position 34 has been tetradecanoylated. Where reference in this text is made to C-terminally extended GLP-1 analogues, the amino acid residue in position 38 is Arg unless otherwise indicated, the optional amino acid residue in position 39 is also Arg unless otherwise indicated and the optional amino acid residue in position 40 is Asp unless otherwise indicated. Also, if a C-terminally extended analogue extends to position 41, 42, 43, 44 or 45, the amino acid sequence of this extension is as in the corresponding sequence in human preproglucagon unless otherwise indicated.

In its broadest aspect, the present invention relates to derivatives of GLP-1 and analogues thereof. The derivatives according to the invention have interesting pharmacological properties, in particular they have a more protracted profile of action than the parent peptides.

In the present text, the designation "an analogue" is used to designate a peptide wherein one or more amino acid residues of the parent peptide have been substituted by another amino acid residue and/or wherein one or more amino acid residues of the parent peptide have been deleted and/or wherein one or more amino acid residues have been added to the parent peptide. Such addition can take place either at the N-terminal end or at the C-terminal end of the parent peptide or both.

The term "derivative" is used in the present text to designate a peptide in which one or more of the amino acid residues of the parent peptide have been chemically modified, e.g. by alkylation, acylation, ester formation or amide formation.

The term "a GLP-1 derivative" is used in the present text to designate a derivative of GLP-1 or an analogue thereof. In the present text, the parent peptide from which such a derivative is formally derived is in some places referred to as the "GLP-1 moiety" of the derivative.

The term "combination therapy" is used in the present text to mean the administration of a single pharmaceutical dosage formulation which comprises the dual PPARα/PPARγ activator and the GLP-1 derivative, as well as administration of each active ingredient in its own separate pharmaceutical dosage formulation. Where separate dosage formulations are used, the PPARα/PPARγ activator and the GLP-1 derivative can be administered to the patient at essentially the same time, e.g. concurrently, or at separate staggered times, e.g. sequentially. When given by different dosage formulations, the route of adminiatration may be the same or different for each agent. Any route of administration known or contemplated for the individual agents is acceptable for practice of the present invention.

Pharmacological Methods

In Vitro PPAR Alpha and PPAR Gamma Activation Activity.

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

In Vitro Transactivation Assays.

Cell culture and transfection: HEK293 cells were grown in DMEM+10% FCS. Cells were seeded in 96-well plates the day before transfection to give a confluency of 50–80% at transfection. A total of 0,8 μg DNA containing 0,64 μg pM1α/γLBD, 0,1 μg pCMVβGal, 0,08 μg pGL2Gal4DBD and 0,02 μg pADVANTAGE was transfected per well using FuGene transfection reagent according to the manufacturers instructions (Roche). Cells were allowed to express protein for 48 h followed by addition of compound.

Plasmids: Human PPAR α and γ was obtained by PCR amplification using cDNA synthesized by reverse transcription of mRNA from liver and adipose tissue respectively. Amplified cDNAs were cloned into pCR2.1 and sequenced. The ligand binding domain (LBD) of each PPAR isoform was generated by PCR(PPARα: aa 167-C-terminus; PPARγ: aa 165-C-terminus) and fused to the DNA binding domain (DBD) of the yeast transcription factor GAL4 by subcloning fragments in frame into the vector pM1 generating the plasmids pM1αLBD and pM1γLBD. Ensuing fusions were verified by sequencing. The reporter was constructed by inserting an oligonucleotide encoding five repeats of the GAL4 recognition sequence (5xCGGAGTACTGTCCTC-CG(AG)) into the vector pGL2 promotor (Promega) generating the plasmid pGL2(GAL4)$_5$. pCMVβGal was purchased from Clontech and pADVANTAGE was purchased from Promega.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments topcounter. To measure β-galactosidase activity 25 μl supernatant from each transfection lysate was transferred to a new microplate. β-galactosidase assays were performed in the microwell plates using a kit from Promega and read in a microplate reader. The β-galactosidase data were used to normalize (transfection efficiency, cell growth etc.) the luciferase data.

Compounds: All compounds were dissolved in DMSO and diluted 1:1000 upon addition to the cells. Compounds were tested in quadruple in five concentrations ranging form 0.01 to 30 μM. Cells were treated with compound for 24 h followed by luciferase assay. Each compound was tested in three separate experiments. $EC_{50}$ values were calculated via non-linear regression using GraphPad PRISM 3.02 (GraphPad Software, San Diego, Calif.). The results were expressed as means.

TABLE 1

In vitro PPAR alpha and PPAR gamma activation of examples according to the present invention.

| | In vitro activation | | | |
|---|---|---|---|---|
| | PPAR α | | PPAR γ | |
| Example no | $EC_{50}$, μM | % max[a] | $EC_{50}$, μM | % max[b] |
| 6 | 0.20 | 217 | 0.7 | 108 |
| 8 | 0.06 | 139 | 0.31 | 126 |
| 12 | 0.05 | 195 | 0.34 | 105 |
| 18 | 0.16 | 181 | 2.67 | 91 |
| 20 | 0.04 | 154 | 1.42 | 112 |

Compounds were tested in at least three separate experiments in five concentrations ranging from 0.01 to 30 μM. $EC_{50}$'s were not calculated for compounds producing transactivation lower than 25% at 30 μM. [a]Fold activation relative to maximum activation obtained with Wy14643 (approx. 20 fold corresponded to 100%) and with [b]rosiglitazone (approx. 120 fold corresponded to 100%).

Pharmaceutical Compositions

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguamide eg. metformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical compositions containing a compound of the present invention may be prepared by conventional techniques, e.g. as described in Remington: The Science and Practise of Pharmacy, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
| --- | --- |
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar. Such mammals include also animals, both domestic animals, e.g. household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonary or transdermal administration comprise from about 0.001 mg to about 100 mg, preferably from about 0.01 mg to about 50 mg of the compounds of formula I admixed with a pharmaceutically acceptable carrier or diluent.

Biological Findings

Protraction of GLP-1 derivatives after s.c. administration

The protraction of a number GLP-1 derivatives of the invention was determined by monitoring the concentration thereof in plasma after sc administration to healthy pigs, using the method described below. For comparison also the concentration in plasma of GLP-1(7-37) after sc. administration was followed. The protraction of other GLP-1 derivatives of the invention can be determined in the same way.

Pigs (50% Duroc, 25% Yorkshire, 25% Danish Landrace, app 40 kg) were fasted from the beginning of the experiment. To each pig 0.5 μnmol of test compound per kg body weight was administered in a 50 μM isotonic solution (5 mM phosphate, pH 7.4, 0.02% Tween®-20 (Merck), 45 mg/ml mannitol (pyrogen free, Novo Nordisk). Blood samples were drawn from a catheter in vena jugularis at the hours indicated in Table 1. 5 ml of the blood samples were poured into chilled glasses containing 175 μl of the following solution: 0.18 M EDTA, 1500 KIE/ml aprotinin (Novo Nordisk) and 3% bacitracin (Sigma), pH 7.4. Within 30 min, the samples were centrifuged for 10 min at 5–6000* g. Temperature was kept at 4° C. The supernatant was pipetted into different glasses and kept at minus 20° C. until use.

The plasma concentrations of the peptides were determined by RIA using a monoclonal antibody specific for the N-terminal region of GLP-1(7-37). The cross reactivities were less than 1% with GLP-1(1-37) and GLP-1(8-36)amide and <0.1% with GLP-1(9-37), GLP-1(10-36)amide and GLP-1(11-36)amide. The entire procedure was carried out at 4° C.

The assay was carried out as follows: 100 μl plasma was mixed with 271 μl 96% ethanol, mixed using a vortex mixer and centrifuged at 2600* g for 30 min. The supernatant was decanted into Minisorp tubes and evaporated completely (Savant Speedvac AS290). The evaporation residue was reconstituted in the assay buffer consisting of 80 mM $NaH_2PO_4/Na_2HPO_4$, 0.1% HSA (Orpha 20/21, Behring), 10 mM EDTA, 0.6 mM thiomersal (Sigma), pH 7.5. Samples were reconstituted in volumes suitable for their expected concentrations, and were allowed to reconstitute for 30 min. To 300 μl sample, 100 μl antibody solution in dilution buffer containing 40 mM $NaH_2PO_4/Na_2HPO_4$, 0.1% HSA, 0.6 mM thiomersal, pH 7.5, was added. A non-specific sample was prepared by mixing 300 μl buffer with 100 μl dilution buffer. Individual standards were prepared from freeze dried stocks, dissolved in 300 μl assay buffer. All samples were pre-incubated in Minisorp tubes with antibody as described above for 72 h. 200 μl tracer in dilution buffer containing 6–7000 CPM was added, samples were mixed and incubated for 48 h. 1.5 ml of a suspension of 200 ml per liter of heparin-stabilised bovine plasma and 18 g per liter of activated carbon (Merck) in 40 mM $NaH_2PO_4/Na_2HPO_4$, 0.6 mM thiomersal, pH 7.5, was added to each tube. Before use, the suspension was mixed and allowed to stand for 2 h at 4° C. All samples were incubated for 1 h at 4° C. and then centrifuged at 3400* g for 25 min. Immediately after the centrifugation, the supernatant was decanted and counted in a γ-counter. The concentration in the samples was calculated from individual standard curves.

Stimulation of cAMP formation in a cell line expressing the cloned human GLP-1 receptor In order to demonstrate efficacy of the GLP-1 derivatives, their ability to stimulate formation of cAMP in a cell line expressing the cloned human GLP-1 receptor was tested. An $EC_{50}$ was calculated from the dose-response curve.

Baby hamster kidney (BHK) cells expressing the human pancreatic GLP-1 receptor were used (Knudsen and Pridal, 1996, Eur. J. Pharm. 318, 429–435). Plasma membranes were prepared (Adelhorst et al, 1994, J. Biol. Chem. 269, 6275) by homogenisation in buffer (10 mmol/l Tris-HCl and 30 mmol/l NaCl pH 7.4, containing, in addition, 1 mmol/l dithiothreitol, 5 mg/l leupeptin (Sigma, St. Louis, Mo., USA), 5 mg/l pepstatin (Sigma, St. Louis, Mo., USA), 100 mg/l bacitracin (Sigma, St. Louis, Mo., USA), and 16 mg/l aprotinin (Novo Nordisk A/S, Bagsvaerd, Denmark)). The homogenate was centrifuged on top of a layer of 41 w/v% sucrose. The white band between the two layers was diluted in buffer and centrifuged. Plasma membranes were stored at −80° C. until used. The assay was carried out in 96-well microtiter plates in a total volume of 140 μl. The buffer used was 50 mmol/l Tris-HCl, pH 7.4 with the addition of 1 mmol/l EGTA, 1.5 mmol/l $MgSO_4$, 1.7 mmol/l ATP, 20 mM GTP, 2 mmol/l 3-isobutyl-1-methylxanthine, 0.01% Tween-20 and 0.1% human serum albumin (Reinst, Behringwerke AG, Marburg, Germany). Compounds to be tested for agonist activity were dissolved and diluted in buffer, added to the membrane preparation and the mixture was incubated for 2 h at 37° C. The reaction was stopped by the addition of 25 μl of 0.05 mol/l HCl. Samples were diluted 10 fold before analysis for cAMP by a scintillation proximity assay (RPA 538, Amersham, UK).

EXAMPLES

The process for preparing compounds of formula 1, and preparations containing them, is further illustrated in the following examples, which however, are not to be construed as limiting.

The structures of the compounds are confirmed by either elemental analysis (MA) nuclear magnetic resonance (NMR), mass spectrometry (MS) or optical rotation. NMR shifts (δ) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385).

The optical rotation was measured on an Advanced Laser Polarimeter.

Compounds used as starting materials are either known compounds or compounds which can readily be prepared by methods known per se.

Abbrevations:
THF: tetrahydrofuran
DMSO: dimethylsulfoxide
MTBE: tertbutylmethylether
$CDCl_3$: deutorated chloroform
min: minutes
h: hours
DMF: N,N-Dimethylformamide.
NMP: N-Methyl-2-pyrrolidone.
EDPA: N-Ethyl-N,N-diisopropylamine.
EGTA Ethylene glycol-bis(β-aminoethyl ether)-N,N,N',N'-tetraacetic acid.
GTP Guanosine 5'-triphosphate.
TFA: Trifluoroacetic acid.
Myr-ONSu: Tetradecanoic acid 2,5-dioxopyrrolidin-1-yl ester.
Pal-ONSu: Hexadecanoic acid 2,5-dioxopyrrolidin-1-yl ester.
Ste-ONSu Octadecanoic acid 2,5-dioxopyrrolidin-1-yl ester.
$HOOC-(CH_2)_6-COONSu$: ω-Carboxyheptanoic acid 2,5-dioxopyrrolidin-1-yl ester.
$HOOC-(CH_2)_{10}-COONSu$: ω-Carboxyundecanoic acid 2,5-dioxopyrrolidin-1-yl ester.
$HOOC-(CH_2)_{12}-COONSu$: ω-Carboxytridecanoic acid 2,5-dioxopyrrolidin-1-yl ester.
$HOOC-(CH_2)_{14}-COONSu$: ω-Carboxypentadecanoic acid 2,5-dioxopyrrolidin-1-yl ester.
$HOOC-(CH_2)_{16}-COONSu$: ω-Carboxyheptadecanoic acid 2,5-dioxopyrrolidin-1-yl ester.
$HOOC-(CH_2)_{18}-COONSu$: ω-Carboxynonadecanoic acid 2,5-dioxopyrrolidin-1-yl ester.

EXAMPLES

Example 1

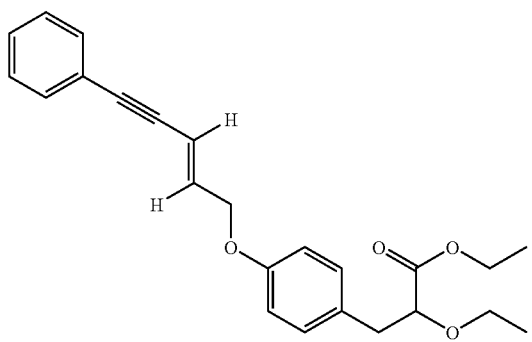

(E)-(S)-2-Ethoxy-3-[4-(5-phenyl-pent-2-en-4-yny-loxy)-phenyl]-propionic acid ethyl ester Method 1 a)

A solution of triethyl phosphonoacetate (25.8 g, 115 mmol) in toluene (100 mL) was added at 0° C. to a stirred suspension of sodium hydride (60% in oil, 3.12 g, 130 mmol) in toluene (300 mL) and the mixture stirred at 0° C. for 30 min. A solution of 3-phenylpropargyl aldehyde (*Org. Syntheses, Coll.* Vol 3, 731–733, 1955) (10.0 g, 77 mmol) in dry THF (15 mL) was added, the mixture slowly warmed to room temperature, and stirring continued for 16 h. The reaction mixture was quenched with ethanol (25 mL) and water (300 mL), the organic phase separated, and the aqueous phase extracted with dichloromethane (300 mL). The combined organic phases were concentrated in vacuo, and submitted to flash column chromatography, petroleum ether/toluene (1:1) graduated to petroleum ether/toluene (1:9) as eluent, to give (1.21 g, 8%) of (E)-5-phenyl-pent-2-en-4-ynoic acid ethyl ester.

$^1$H NMR ($CDCl_3$, 300 MHz) δ: 1.30 (t, 3H), 4.25 (q, 2H), 6.30 (d, 1H, $J_{trans}$=15 Hz), 6.98 (d, 1H, $J_{trans}$=15 Hz), 7.30–7.40 (m, 3H), 7.45–7.50 (m, 2H).

b)

Diisobutylaluminium hydride (1.0 M solution in toluene, 42 mL, 42 mmol) was added, under a nitrogen atmosphere at −70° C., to a stirred solution of (E)-5-phenyl-pent-2-en-4-ynoic acid ethyl ester (1.2 g, 5.99 mmol) in dry THF (105 mL). After stirring for 1.5 h, the reaction mixture was quenched with methanol (5 mL) followed by saturated aqueous Rochelle's salt (90 mL) and 1 N sodium hydroxide (40 mL). The organic phase was separated, and the aqueous phase extracted with ethyl acetate (250 mL, 2×). The combined organic phases were dried ($MgSO_4$), filtered and concentrated in vacuo to give 948 mg (100%) of (E)-5-phenyl-pent-2-en-4-yn-1-ol.

$^1$H NMR ($CDCl_3$, 300 MHz) δ: 2.20 (bs, 1H), 4.25 (d, 2H), 5.95 (dt, 1H, $J_{trans}$=15 Hz), 6.35 (dt, 1H, $J_{trans}$=15 Hz), 7.23–7.35 (m, 3H), 7.35–7.48 (m, 2H).

c)

(E)-5-Phenyl-pent-2-en-4-yn-1-ol (328 mg, 2.07 mmol), tributylphosphine (606 mg, 3.0 mmol) and (S)-2-ethoxy-3-(4-hydroxy-phenyl)-propionic acid ethyl ester (*Tetrahedron Letters*, Vol. 35, No. 19, 3139–3142, 1994) (495 mg, 2.07 mmol) were successively dissolved in dry benzene (30 mL) under a nitrogen atmosphere and the solution cooled to 0° C. Solid 1,1'-(azodicarbonyl) dipiperidine (756 mg, 3.0 mmol) was added, the mixture stirred for 10 min., then warmed to room temperature and stirred for 16 h. The reaction mixture was filtered and the filtrate concentrated in vacuo. The product was purified by flash column chromatography eluting with toluene graduated to toluene/ethyl acetate (19:1) to give 450 mg (57%) of the title compound.

$^1$H NMR ($CDCl_3$, 300 MHz) δ: 1.18 (t, 3H), −1.25 (t, 3H), 2.95 (d, 2H), 3.30–3.42 (m, 1H), 3.55–3.67 (m, 1H), 3.98 (t, 1H), 4.15 (q, 2H), 4.60 (d, 2H), 6.15 (dt, 1H, $J_{trans}$=15 Hz), 6.48 (dt, 1H, $J_{trans}$=15 Hz), 6.85 (d, 2H), 7.15 (d, 2H), 7.28–7.35 (m, 3H), 7.40–7.46 (m, 2H).

$[α]_{670}^{25}$=30°±4°

Method 2 a)

To a mixture of (E)-5-phenyl-pent-2-en-4-yn-1-ol (Method 1b) (4.9 g, 31.0 mmol) and triethylamine (3.8 g, 38.0 mmol) in dry dichloromethane (200 mL) was added methanesulfonyl chloride (3.8 g, 33 mmol) dropwise. Stirring was continued at room temperature overnight. The reaction mixture was concentrated in vacuo and the residue washed with heptane/dichloromethane (×2) to give 4.5 g (82%) crude (E)-(5-chloro-pent-3-en-1-ynyl)-benzene.

$^1$H NMR (CDCl$_3$, 300 MHz) 6:4.13 (d, 2H)), 6.0 (d, 1H, J$_{trans}$=15 Hz), 6.29 (dt, 1H, J$_{trans}$=15 Hz), 7.28–7.35 (m, 3H), 7.40–7.48 (m, 2H).

b)

To a solution of (E)-(5-chloro-pent-3-en-1-ynyl)-benzene (177 mg, 1.0 mmol) and (S)-2-ethoxy-3-(4-hydroxy-phenyl)-propionic acid ethyl ester (238 mg, 1.0 mmol) in acetone (15 mL) was added potassium carbonate (700 mg, 5.0 mmol) and potassium iodide (17 mg, 0.1 mmol). The mixture was heated to reflux over night with stirring. Water was added and the product extracted with tert-butyl methyl ether (×3) The combined organic phases were dried (MgSO$_4$), filtered and concentrated in vacuo, to give the title compound as a crude product.

Method 3 a)

A solution of (E)-5-phenyl-pent-2-en-4-yn-1-ol (Method 1b) (980 mg, 6.2 mmol) in dry toluene (20 mL) was cooled on ice and phosphorus tribromide (0.59 mL, 6.2 mmol) added slowly. After 16 h at 5° C. the mixture was diluted with ethyl acetate and washed with water (×3). The organic phase was concentrated in vacuo and the residue extracted with heptane (×3). The combined heptane phases were concentrated in vacuo to give 900 mg of crude (E)-(5-bromo-pent-3-en-1-ynyl)-benzene. (According to NMR the product contained ~5% of the (Z)-isomer).

$^1$H NMR (CDCl$_3$, 300 MHz) δ: 4.02 (d, 1H), 4.25 (d, 0.05H), 5.82 (d, 0.05H, J$_{cis}$=8 Hz), 5.95 (d, 1H, J$_{trans}$=16 Hz), 6.18 (dt, 0.05H, J$_{cis}$=8 Hz), 6.35 (dt, 1H, J$_{trans}$=16 Hz), 7.26–7.35 (m, 3H), 7.35–7.48 (m, 2H).

Example 2

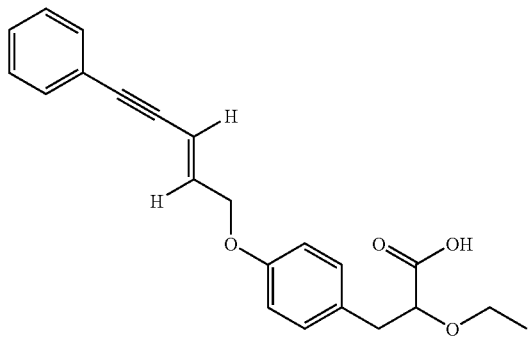

Aqueous sodium hydroxide (1N, 5 mL, 5.0 mmol) was added to a stirred solution of (E)-(S)-2-ethoxy-3-[4-(5-phenyl-pent-2-en-4-ynyloxy)-phenyl]-propionic acid ethyl ester (example 1) (450 mg, 1.18 mmol) in ethanol (5 mL) and the resulting mixture stirred at room temperature for 16 h. The ethanol was evaporated in vacuo and the mixture acidified to pH 1 with 1N hydrochloric acid. The product was extracted into ethyl acetate (30 mL×2), and the combined organic phases dried (MgSO$_4$), filtered and evaporated to give 225 mg (54%) of the title compound as white crystals.

$^1$H NMR (CDCl$_3$, 300 MHz) δ: 1.20 (t, 3H), 2.97 (dd, 1H), 3.10 (dd, 1H), 3.42–3.65 (m, 2H), 4.05 (dd, 1H), 4.63 (dd, 2H), 6.08 (dt, 1H, J$_{trans}$=15 Hz), 6.39 (dt, 1H, J$_{trans}$=15 Hz), 6.85 (d, 2H), 7.15 (d, 2H), 7.30–7.35 (m, 3H), 7.40–7.48 (m, 2H).

$[\alpha]_{670}^{25}$=23°±3°

Example 3

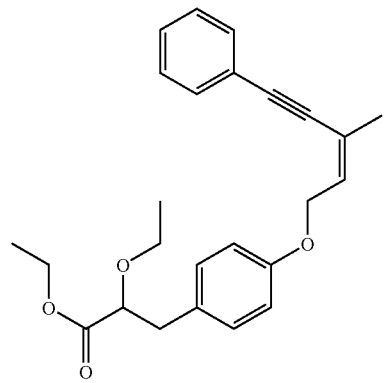

(Z)-(S)-2-Ethoxy-3-[4-(3-methyl-5-phenyl-pent-2-en-4-ynyloxy)-phenyl]-propionic acid ethyl ester 1,1'-(azodicarbonyl) dipiperidine (0.504 g, 2.0 mmol) was added at 0° C. to a stirred solution of tributylphosphine (0.493 mL, 2.0 mmol), (Z)-3-methyl-5-phenyl-pent-2-en-4-yn-1-ol (0.172 g, 1.0 mmol) (*J. Org. Chem.* 1999, 64 (21), 7687–7692), and (S)-ethyl 2-ethoxy-3-(4-hydroxy-phenyl)-propionate (0.262 g, 1.1 mmol) in dry benzene (20 mL), the mixture allowed to warm to room temperature, and stirring continued for 24 h. The resulting mixture was evaporated in vacuo, and the residue purified by flash column chromatography on silica gel (20% ethyl acetate in n-heptane eluent) to give (Z)-(S)-2-ethoxy-3-[4-(3-methyl-5-phenyl-pent-2-en-4-ynyloxy)-phenyl]-propionic acid ethyl ester as an oil; 0.267 g (68%).

$^1$H NMR (300 MHz, CDCl$_3$) δ: 1.1–1.25 (6H, m), 2.0 (3H, d), 2.93 (2H, d), 3.25–3.38 (1H, m), 3.51–3.62 (1H, m), 3.97 (1H, t), 4.13 (2H, q), 4.80 (2H, dd), 5.95 (1H, dt), 6.86 (2H, d), 7.15 (2H, d), 7.25–7.35 (3H, m), 7.40–7.43 (2H, m).

Example 4

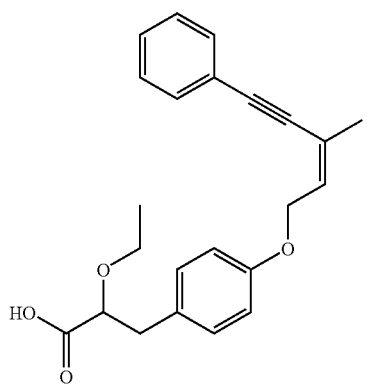

(Z)-(S)-2-Ethoxy-3-[4-(3-methyl-5-phenyl-pent-2-en-4-ynyloxy)-phenyl]-propionic acid Sodium hydroxide (1N, 1.25 mL, 1.25 mmol) was added to a solution of (Z)-(S)-2-ethoxy-3-[4-(3-methyl-5-phenyl-pent-2-en-4-ynyloxy)-phenyl]-propionic acid ethyl ester (example 3) (0.246 g, 0.627 mmol) in ethanol (20 mL) and the mixture stirred at 70° C. for 2.5 h. After cooling to room temperature the resulting mixture was partitioned between water (50 mL) and ethyl acetate (50 mL). The aqueous phase was collected, acidified with 1N hydrochloric acid (5 mL) and extracted into ethyl acetate (100 mL). The organic phase was washed with brine, dried ($Na_2SO_4$) and evaporated to give (E)-(S)-3-[4-(3-biphenyl-4-yl-but-2-enyloxy)-phenyl]-2-ethoxy-propionic acid as an oil; 0.150 g (66%).

$^1$H NMR (300 MHz, $CDCl_3$) δ: 1.05 (3H, t), 1.92 (3H, d), 2.8 (1H, dd), 2.92 (1H, dd), 3.2–3.3 (1H, m), 3.4–3.5 (1H, m), 3.9 (1H, dd), 4.7 (2H, dd), 5.85 (1H, dt), 6.8 (2H, d), 7.1 (2H, d), 7.2–7.25 (3H, m), 7.3–7.4 (2H, m), 8.9 (1H, brs).

Example 5

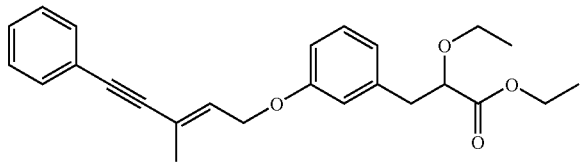

(E)-(S)-2-Ethoxy-3-[4-(3-methyl-5-phenyl-pent-2-en-4-ynyloxy)-phenyl]-propionic acid ethyl ester The title compound was prepared from of (E)-3-methyl-5-phenyl-pent-2-en-4-yn-1-ol (0.172 g, 1.0 mmol), (J. Med. Chem. 1998, 41(14), 2524–2536), tributylphosphine (0.370 mL, 1.5 mmol), 1,1'-(azodicarbonyl) dipiperidine (0.378 g, 1.5 mmol) and (S)-ethyl 2-ethoxy-3-(4-hydroxy-phenyl)-propionate (0.262 g, 1.1 mmol) in dry benzene (20 mL) by a procedure analogous to that described in example 3, yielding 0.276 g (68%) of (E)-(S)-2-ethoxy-3-[4-(3-methyl-5-phenyl-pent-2-en-4-ynyloxy)-phenyl]-propionic acid ethyl ester.

$^1$H NMR (300 MHz, $CDCl_3$) δ: 1.1–1.25 (6H, m), 1.98 (3H, d), 2.95 (2H, d), 3.29–3.4 (1H, m), 3.53–3.65 (1H, m), 3.95 (1H, t), 4.15 (2H, q), 4.60 (2H, dd), 6.15 (1H, dt), 6.8 (2H, d), 7.15 (2H, d), 7.20–7.3 (3H, m), 7.35–7.45 (2H, m).

Example 6

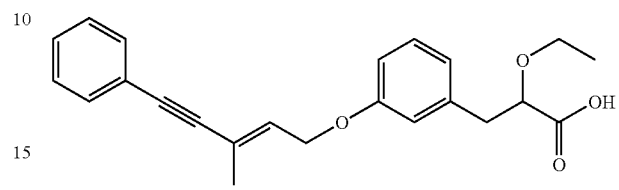

(E)-(S)-2-Ethoxy-3-[4-(3-methyl-5-phenyl-pent-2-en-4-ynyloxy)-phenyl]-propionic acid The title compound was prepared from (E)-(S)-2-ethoxy-3-[4-(3-methyl-5-phenyl-pent-2-en-4-ynyloxy)-phenyl]-propionic acid ethyl ester (example 5) (0.270 g, 0.698 mmol) and sodium hydroxide (1 N, 1.4 mL, 1.4 mmol) by a procedure analogous to that described in example 4 yielding 0.100 g (39%) of (E)-(S)-2-ethoxy-3-[4-(3-methyl-5-phenyl-pent-2-en-4-ynyloxy)-phenyl]-propionic acid.

$^1$H NMR (300 MHz, $CDCl_3$) δ: 1.18 (3H, t), 1.98 (3H, d), 2.9 (1H, dd), 2.05 (1H, dd), 3.4–3.5 (1H, m), 3.55–3.65 (1H, m), 4.05 (1H, dd), 4.62 (2H, dd), 6.15 (1H, m), 6.8 (2H, d), 7.15 (2H, d), 7.3 (3H, m), 7.43 (2H, m).

Example 7

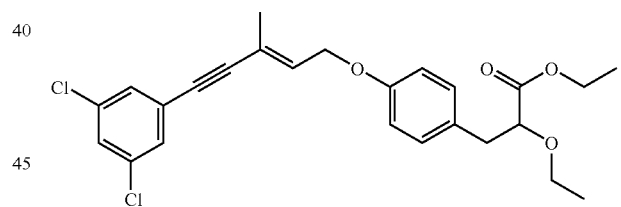

Ethyl (E)-(S)-2-ethoxy-3-[4-(3-methyl-5-(3,5-dichloro-phenyl)-pent-2-en-4-ynyloxy)-phenyl]-propionate Method 1 a)

To a solution of 1,3-dichloro-5-iodo-benzene (3.44 g, 12.6 mmol) in THF (220 mL) was added $PdCl_2(PPh_3)_2$ (904 mg, 1.29 mmol), 3-butyn-2-one (2.18 g, 32.0 mmol), copper(I) iodide (380 mg, 2 mmol) and diisopropylamine (44 mL). The reaction mixture was stirred at room temperature for 48 hours, filtered and evaporated. The residue was purified by column chromatography using methylene chloride:hexanes (1:1) as eluent. The desired 4-(3,5-dichloro-phenyl)-3-butyn-2-one product was isolated in 977 mg yield.

$^1$H NMR (300 MHz, $CDCl_3$) δ: 2.46 (s, 3H), 7.45 (s, 3H).

b)

To a solution of sodium (163 mg, 6.8 mmol) in ethanol (6 mL) at –10° C. was added triethyl phosphonoacetate (1.37 mL, 6.8 mmol) and the reaction mixture was stirred for 5 minutes. A solution of 4-(3,5-dichloro-phenyl)-3-butyn-2-one (214 mg, 5.7 mmol) in ethanol (4 mL) was added and the reaction mixture stirred overnight at room temperature and evaporated. The residue was treated with water (10 mL) and extracted with 3×30 mL ethyl acetate. The dried organic phases were evaporated to give a mixture of (E)- and (Z)-3-methyl-5-(3,5-dichloro-phenyl)-pent-2-en-4-ynoic acid ethyl esters. The mixture was separated by column chromatography using hexanes:methylene chloride (10:1) as eluent, giving pure (E) in 130 mg, and pure (Z) in 160 mg yields.

(E)-3-methyl-5-(3,5-dichloro-phenyl)-pent-2-en-4-ynoic acid ethyl ester: $^1$H NMR (300 MHz, CDCl$_3$) δ: 1.29 (t, 3H), 2.36 (s, 3H), 4.20 (q, 2H), 6.16 (m, 1H), 7.34 (s, 3H).

(Z)-3-methyl-5-(3,5-dichloro-phenyl)-pent-2-en-4-ynoic acid ethyl ester: $^1$H NMR (300 MHz, CDCl$_3$) δ: 1.29 (t, 3H), 2.12 (s, 3H), 2.25 (q, 2H), 6.09 (m, 1H), 7.34 (m, 1H), 7.40 (m, 2H).

c)

To a solution of (E)-3-methyl-5-(3,5-dichloro-phenyl)-pent-2-en-4-ynoic acid ethyl ester (130 mg, 0.46 mmol) in THF (0.5 mL) was added dropwise diisobutylaluminium hydride (1.0 M solution in toluene, 2.1 mL, 2.1 mmol) at –20° C. The reaction mixture was stirred for 2 hours at –20° C., whereafter saturated ammonium chloride was added. The mixture was treated with ethyl acetate and decalite and filtered. The filtrate was evaporated to give crude (E)-3-methyl-5-(3,5-dichloro-phenyl)-pent-2-en-4-yn-1-ol in 113 mg yield.

$^1$H NMR (300 MHz, CDCl$_3$) δ: 1.85 (s, 3H), 2.00 (br.s, 1H), 4.20 (d, 2H), 6.04 (m, 1H), 7.20 (s, 3H).

d)

To a solution of (E)-3-methyl-5-(3,5-dichloro-phenyl)-pent-2-en-4-yn-1-ol (113 mg, 0.46 mmol) in THF (10 mL) was added triphenylphosphine (218 mg, 0.71 mmol) at 0° C. To the mixture was added diethyl azodicarboxylate (0.109 mL, 0.71 mmol) and (S)-2-ethoxy-3-(4-hydroxy-phenyl)-propionic acid ethyl ester (169 mg, 0.71 mmol) and the reaction mixture was stirred at 0° C. for 2 h and then at room temperature overnight. Water (15 mL) was added and the mixture was extracted with methylene chloride (3×30 mL). The combined and dried organic phases were evaporated and the residue purified by column chromatography using methylene chloride as eluent to give the title compound in 35 mg yield.

$^1$H NMR (300 MHz, CDCl$_3$) δ: 1.16 (t, 3H), 1.23 (t, 3H), 1.98 (s, 3H), 2.97 (d, 2H), 3.42–3.30 (m, 1H), 3.65–3.55 (m, 1H), 3.97 (t, 1H), 4.16 (q, 2H), 4.62 (d, 2H), 6.20 (m, 1H), 8.83 (d, 2H), 7.16 (d, 2H), 7.37 (m, 3H).

Method 2 a)

A solution of 1-bromo-3,5-dichloro-benzene (904 mg, 4.0 mmol), PdCl$_2$(PPh$_3$)$_2$ (96 mg, 0.08 mmol), 2-methyl-3-butyn-2-ol (672 mg, 8.0 mmol) and CuI (4 mg, 0.02 mmol) in diethylamine (16 mL) was stirred at room temperature for 50 h. The reaction mixture was evaporated and the residue purified by column chromatography using methylene chloride as eluent. The desired product 3-(2,5-dichlorophenyl)-2-methyl-3-butyn-2-ol was isolated in 910 mg (99%) yield.

$^1$H NMR (300 MHz, CDCl$_3$) δ:1.62 (6H, s), 7.30 (3H, s).

b)

To a solution of 3-(2,5-dichlorophenyl)-2-methyl-3-butyn-2-ol (840 mg, 3.46 mmol) in dry toluene (15 mL) was added sodium hydroxide pellets (45 mg) at room temperature. The reaction mixture was heated and a mixture of toluene and formed acetone was distilled of. The reaction mixture was washed with aqueous potassium carbonate (1M, 2.5 mL), water (2.5 mL) and brine (2.5 mL). The organic phase was dried and evaporated to give the desired product 1,3-dichloro-phenyl acetylene in 537 mg (91%) yield.

$^1$H NMR (300 MHz, CDCl$_3$) δ: 3.15 (1H, s), 7.37 (3H, s).

c)

To a solution of 1,3-dichloro-phenyl acetylene (6.07 g, 35.5 mmol) in dry THF (60 mL) was added palladium acetate (186 mg, 0.68 mmol), ethyl 2-butynoate (5.97 g, 53.2 mmol) and tris (2,6-dimethoxyphenyl)phosphine (316 mg, 0.68 mmol) at room temperature. The reaction mixture was stirred for 18 h and filtered. The filtrate was washed with water (10 mL), and the water phase was extracted with ether (10 mL). The combined organic phases were dried and evaporated. The residue was purified by column chromatography using heptane:THF (20:1) as eluent. (E)-3-Methyl-5-(3,5-dichloro-phenyl)-pent-2-en-4-ynoic acid ethyl ester was isolated in 4.65 g (46%) yield.

d)

The title compound was prepared from (E)-3-methyl-5-(3,5-dichloro-phenyl)-pent-2-en-4-ynoic acid ethyl ester according to the procedure described in method 1,c–d.

Example 8

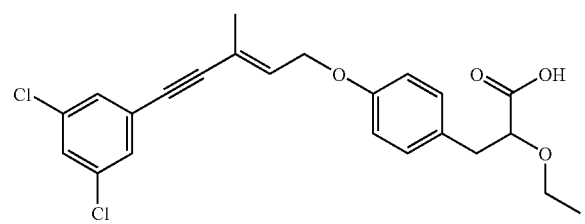

(E)-(S)-2-ethoxy-3-[4-(3-methyl-5-(3,5-dichloro-phenyl)-pent-2-en-4-ynyloxy)-phenyl]-propionic acid Ethyl (E)-(S)-2-ethoxy-3-[4-(3-methyl-5-(3,5-dichloro-phenyl)-pent-2-en-4-ynyloxy)-phenyl]-propionate was hydrolysed as described in Example 2 to give the title compound.

$^1$H NMR (300 MHz, CDCl$_3$) δ: 1.12 (t, 3H), 1.95 (s, 3H), 3.12–2.85 (m, 2H), 3.48–3.32 (m, 1H), 3.65–3.53 (m, 1H), 4.03 (m, 1H), 4.59 (d, 2H), 6.17 (t, 1H), 6.80 (d, 2H), 7.15 (d, 2H), 7.30 (s, 3H).

Example 9

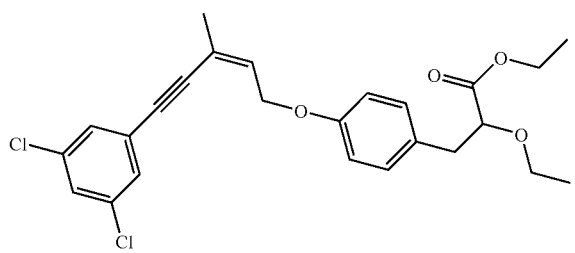

Ethyl (Z)-(S)-2-ethoxy-3-[4-(3-methyl-5-(3,5-dichloro-phenyl)-pent-2-en-4-ynyloxy)-phenyl]-propionate a)

(Z)-3-methyl-5-(3,5-dichloro-phenyl)-pent-2-en-4-yn-1-ol was made from (Z)-3-methyl-5-(3,5-dichloro-phenyl)-pent-2-en-4-ynoic acid ethyl ester (160 mg) (example 7b) using the conditions described in example 7c. Yield 140 mg.

$^1$H NMR (300 MHz, CDCl$_3$) δ: 1.88 (s, 3H), 1.92 (br. s, 1H), 4.33 (d, 2H), 5.90 (t, 1H), 7.21 (s, 3H).

b)

The title compound was prepared from (Z)-3-methyl-5-(3,5-dichloro-phenyl)-pent-2-en-4-yn-1-ol (140 mg) using the conditions described in example 7d. Yield 172 mg.

$^1$H NMR (300 MHz, CDCl$_3$) δ: 1.17 (t, 3H), 1.25 (t, 3H), 2.00 (s, 3H), 2.95 (d, 2H), 3.42–3.28 (m, 1H), 3.67–3.55 (m, 1H), 3.98 (t, 1H), 4.16 (q, 2H), 4.77 (d, 2H), 6.02 (t, 1H), 6.86 (d, 2H), 7.28 (d, 2H), 7.32 (s, 3H).

Example 10

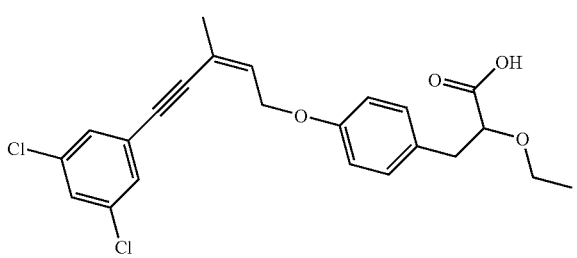

(Z)-(S)-2-ethoxy-3-[4-(3-methyl-5-(3,5-dichloro-phenyl)-pent-2-en-4-ynyloxy)-phenyl]-propionic acid Ethyl (Z)-(S)-2-ethoxy-3-[4-(3-methyl-5-(3,5-dichloro-phenyl)-pent-2-en-4-ynyloxy)-phenyl]-propionate was hydrolysed as described in Example 2 to give the title compound. Yield 164 mg.

$^1$H NMR (300 MHz, CDCl$_3$) δ: 1.18 (t, 3H), 2.01 (s, 3H), 3.10–2.90 (m, 2H), 3.46–3.33 (m, 1H), 3.67–3.55 (m, 1H), 4.04 (m, 1H), 4.75 (d, 2H), 6.02 (t, 1H), 6.87 (d, 2H), 7.18 (d, 2H), 7.33 (s, 3H).

Example 11

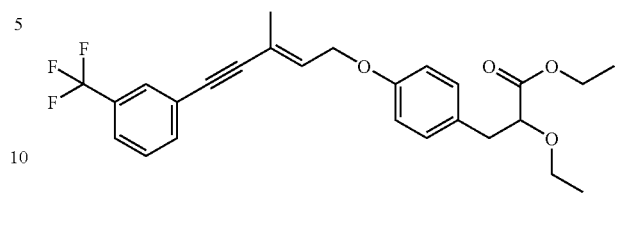

Ethyl (E)-(S)-2-ethoxy-3-[4-(3-methyl-5-(3-trifluoromethyl-phenyl)-pent-2-en-4-ynyloxy)-phenyl]-propionate The title compound was made as described in example 7a–d using 3-trifluoromethyl-1-iodo-benzene instead of 1,3-dichloro-5-iodo-benzene in example 7a.

$^1$H NMR (300 MHz, CDCl$_3$) δ: 1.18 (t, 3H), 1.24 (t, 3H), 2.00 (s, 3H), 2.96 (d, 2H), 3.42–3.31 (m, 1H), 3.66–3.55 (m, 1H), 3.98 (t, 1H), 4.27 (q, 2H), 4.65 (d, 2H), 6.23 (1H), 6.84 (d, 2H), 7.18 (d, 2H), 7.71–7.38 (m, 5H).

Example 12

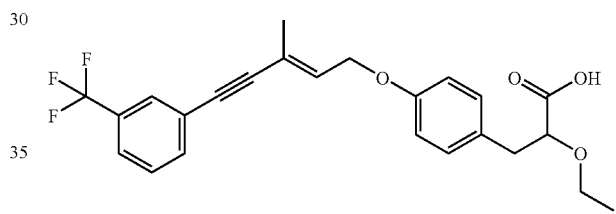

(E)-(S)-2-ethoxy-3-[4-(3-methyl-5-(3-trifluoromethyl-phenyl)-pent-2-en-4-ynyloxy)-phenyl]-propionic acid Ethyl (E)-(S)-2-ethoxy-3-[4-(3-methyl-5-(3-trifluoromethyl-phenyl)-pent-2-en-4-ynyloxy)-phenyl]-propionate was hydrolysed as described in Example 2 to give the title compound.

$^1$H NMR (300 MHz, CDCl$_3$) δ: 1.19 (t, 3H), 1.98 (s, 3H), 3.12–2.90 (m, 2H), 3.48–3.36 (m, 1H), 3.69–3.56 (m, 1H), 4.50 (m, 1H), 4.64 (d, 2H), 6.21 (t, 1H), 6.85 (d, 2H), 7.18 (d, 2H), 7.70–7.49 (m, 5H).

Example 13

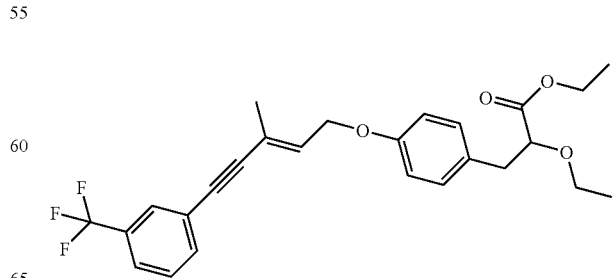

Ethyl (Z)-(S)-2-ethoxy-3-[4-(3-methyl-5-(3-trifluoromethyl-phenyl)-pent-2-en-4-ynyloxy)-phenyl]-propionate The title compound was synthesised from (Z)-3-methyl-5-(3-trifluromethyl-phenyl)-pent-2-en-4-yn-1-ol which was derived from the reaction sequence described in example 11 using the conditions described in example 7c–d.
$^1$H NMR (300 MHz, CDCl$_3$) δ: 1.18 (t, 3H), 2.23 (t, 3H), 2.03 (s, 3H), 2.96 (d, 2H), 3.42–3.30 (m, 1H), 3.66–3.55 (m, 1H), 3.96 (t, 1H), 4.15 (q, 2H), 4.82 (d, 2H), 6.03 (t, 1H), 6.87 (d, 2H), 7.17 (d, 2H), 7.70–7.43 (m, 5H).

Example 14

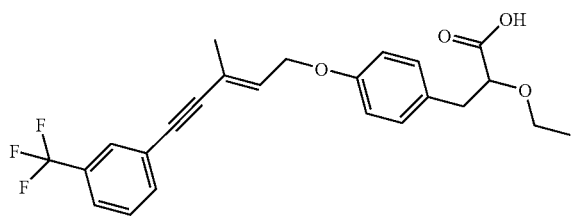

(Z)-(S)-2-ethoxy-3-[4-(3-methyl-5-(3-trifluoromethyl-phenyl)-pent-2-en-4-ynyloxy)-phenyl]-propionic acid Ethyl (Z)-(S)-2-ethoxy-3-[4-(3-methyl-5-(3-trifluoromethyl-phenyl)-pent-2-en-4-ynyloxy)-phenyl]-propionate was hydrolysed as described in Example 2 to give the title compound.
$^1$H NMR (300 MHz, CDCl$_3$) δ: 1.16 (t, 3H), 2.02 (s, 3H), 3.10–2.92 (m, 2H), 3.47–3.36 (m, 1H), 3.68–3.57 (m, 1H), 4.03 (m, 1H), 4.80 (d, 2H), 6.02 (t, 1H), 6.89 (d, 2H), 7.18 (d, 2H), 7.72–7.42 (m, 5H).

Example 15

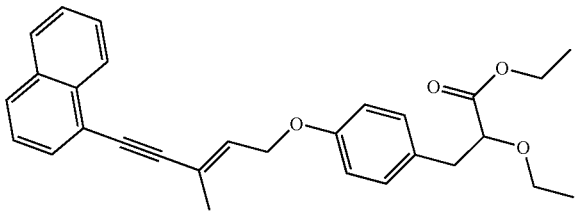

Ethyl (E)-(S)-2-ethoxy-3-[4-(3-methyl-5-(1-naphthyl)-pent-2-en-4-ynyloxy)-phenyl]-propionate The title compound was made as described in example 7a–d using 1-iodonaphthalene instead of 1,3-dichloro-5-iodo-benzene in example 7a.
$^1$H NMR (300 MHz, CDCl$_3$) δ: 1.18 (t, 3H), 1.24 (t, 3H), 2.08 (s, 3H), 2.96 (d, 2H), 3.42–3.30 (m, 1H), 3.66–3.53 (m, 1H), 3.98 (t, 1H), 4.15 (q, 2H), 4.65 (d, 2H), 6.30 (m, 1H), 6.86 (d, 2H), 7.18 (d, 2H), 7.86–7.38 (m, 6H), 8.33 (d, 1H).

Example 16

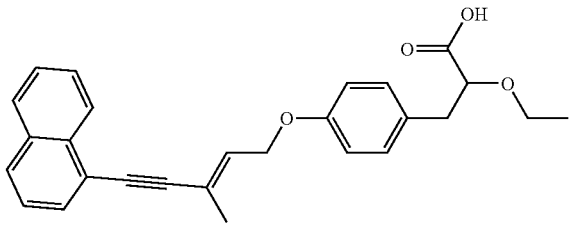

(E)-(S)-2-ethoxy-3-[4-(3-methyl-5-(1-naphthyl)-pent-2-en-4-ynyloxy)-phenyl]-propionic acid Ethyl (E)-(S)-2-ethoxy-3-[4-(3-methyl-5-(1-naphthyl)-pent-2-en-4-ynyloxy)-phenyl]-propionate was hydrolysed as described in Example 2 to give the title compound.
$^1$H NMR (300 MHz, CDCl$_3$) δ: 1.19 (t, 3H), 1.98 (s, 3H), 3.12–2.90 (m, 2H), 3.48–3.36 (m, 1H), 3.69–3.56 (m, 1H), 4.05 (m, 1H), 4.66 (d, 2H), 6.30 (t, 1H), 6.85 (d, 2H), 7.18 (d, 2H), 7.90–7.45 (m, 6H), 8.44 (d, 1H).

Example 17

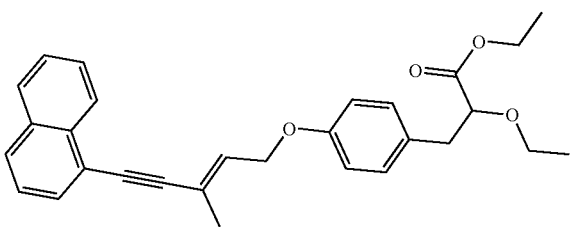

Ethyl (Z)-(S)-2-ethoxy-3-[4-(3-methyl-5-(1-naphthyl)-pent-2-en-4-ynyloxy)-phenyl]-propionate The title compound was synthesised from (Z)-3-methyl-5-(1-naphthyl)-pent-2-en-4-yn-1-ol isolated in example 15 using the conditions described in example 7c–d.
$^1$H NMR (300 MHz, CDCl$_3$) δ: 1.18 (t, 3H), 1.23 (t, 3H), 2.14 (s, 3H), 2.97 (d, 2H), 3.42–3.30 (m, 1H), 3.66–3.53 (m, 1H), 3.98 (t, 1H), 4.15 (q, 2H), 4.95 (d, 2H), 6.06 (m, 1H), 6.94 (d, 2H), 7.18 (d, 2H), 7.86–7.40 (m, 6H), 8.30 (m, 1H).

Example 18

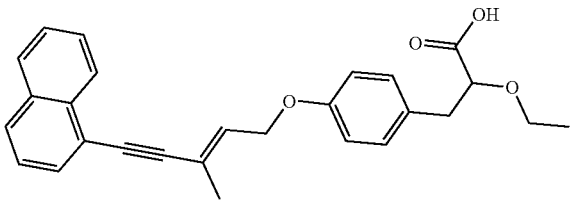

(Z)-(S)-2-ethoxy-3-[4-(3-methyl-5-(1-naphthyl)-pent-2-en-4-ynyloxy)-phenyl]-propionic acid Ethyl (Z)-(S)-2-ethoxy-3-[4-(3-methyl-5-(1-naphthyl)-pent-2-en-4-ynyloxy)-phenyl]-propionate was hydrolysed as described in Example 2 to give the title compound.

$^1$H NMR (300 MHz, CDCl$_3$) δ: 1.04 (t, 3H), 2.02 (s, 3H), 3.00–2.80 (m, 2H), 3.34–3.22 (m, 1H), 3.57–3.46 (m, 1H), 3.94 (m, 1H), 4.83 (d, 2H), 5.94 (t, 1H), 6.84 (d, 2H), 7.08 (d, 2H), 7.75–7.26 (m, 6H), 8.20 (m, 1H), 9.2 (br.s, 1H).

Example 19

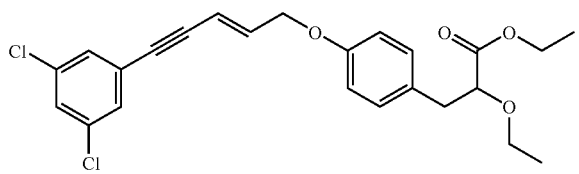

Ethyl (E)-(S)-2-ethoxy-3-[4-(-5-(3,5-dichloro-phenyl)-pent-2-en-4-ynyloxy)-phenyl]-propionate a)
To a solution of 1,3-dichloro-5-iodo-benzene (5.44 g, 20 mmol) in diethylamine (75 mL) was added PdCl$_2$(PPh$_3$)$_2$ (280 mg, 0.4 mmol), trimethylsilylacetylene (2.36 g, 24.0 mmol) and copper(I)iodide (20 mg, 0.1 mmol). The reaction mixture was stirred at room temperature for 24 h, filtered and evaporated. The residue was purified by column chromatography using heptane:ethyl acetate (8:2) as eluent. The desired (3,5-dichlorophenylethynyl)-trimethyl-silane product was isolated in 4.85 g yield.

$^1$H NMR (300 MHz, CDCl$_3$) δ: 0.09 (s, 9H), 7.15 (m, 3H).

b)
To a solution of (3,5-dichloro-phenylethynyl)-trimethyl-silane (4.85 g, 19.9 mmol) in methanol (50 mL) was added 1 M potassium hydroxide (30 mL). The reaction mixture was stirred 1 h at room temperature and evaporated. The residue was treated with water (10 mL) and extracted with 3×40 mL diethyl ether. The tried organic phases were evaporated to give the desired 1,3-dichloro-5-ethynyl-benzene product in 2.3 g yield.

$^1$H NMR (300 MHz, CDCl$_3$) δ: 2.13 (s, 1H), 7.38 (s, 3H).

c)
To a solution of 1,3-dichloro-5-ethynyl-benzene (1.52 g, 8.9 mmol) in triethylamine (32.4 mL) was added PdCl$_2$ (PPh$_3$)$_2$ (57.15 mg, 0.08 mmol), (E)-3-iodo-prop-2-enoic-acid ethyl ester (1.84 g, 8.1 mmol) and copper(I)iodide (7.7 mg, 0.04 mmol). The reaction mixture was stirred for 2 h at 50° C., whereafter the reaction mixture was cooled to room temperature, water (30 mL) added and the mixture extracted with diethyl ether (3×20 mL). The combined and dried organic phases were evaporated to give crude (E)-5-(3,5-dichlorophenyl)-pent-2-en-4-ynoic acid ethyl ester in 1.1 g yield.

$^1$H NMR (300 MHz, CDCl$_3$) δ: 1.32 (t, 3H), 4.22 (q, 2H), 6.32 (d, 1H, J=16 Hz), 6.92 (d, 1H, J=16 Hz), 7.37 (s, 3H).

d)
To a solution of diisobutylaluminium hydride (1.0 M solution in toluene, 20 mL, 20 mmol) at −78° C. was slowly added (E)-5-(3,5-dichloro-phenyl)-pent-2-en-4-ynoic acid ethyl ester (1.1 g, 4.08 mmol). The reaction mixture was stirred for 2 h at −78° C., where after the reaction mixture was poured into hydrocloride acid (6N, 50 mL) and extracted with diethyl ether (3×40 mL) The combined and dried organic phases were evaporated to give crude (E)-5-(3,5-dichloro-phenyl)-pent-2-en-4-yn-1-ol in 750 mg yield.

$^1$H NMR (300 MHz, CDCl$_3$) δ: 4.3 (dd, 2H), 5.95 (dt, 1H,J=5 and 16 Hz), 6.4 (dt, 1H, J=5 and 16 Hz), 7.30 (s, 3H).

e)
The title compound was prepared from (E)-5-(3,5-dichloro-phenyl)-pent-2-en-4-yn-1-ol (454 mg, 2 mmol) using the conditions described in example 7d. Yield 125 mg yield.

$^1$H NMR (300 MHz, CDCl$_3$) δ: 1.14 (t, 3H), 1.22 (t, 3H), 2.95 (d, 2H), 3.30–3.42 (m, 1H), 3.55–3.67 (m, 1H), 3.95 (t, 1H), 4.16 (q, 2H), 4.6 (dd, 2H, J=1.5 and 5 Hz), 6.05 (dt, 1H, J=1.5 and 16 Hz), 6.35 (dt, 1H, J=5 and 16 Hz), 6.83 (d, 2H), 7.15 (d, 2H), 7.36 (m, 3H).

Example 20

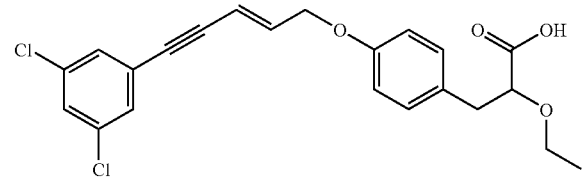

(E)-(S)-2-Ethoxy-3-[4-(5-(3,5-dichloro-phenyl)-pent-2-en-4-ynyloxy)-phenyl]-propionic acid Ethyl (E)-(S)-2-ethoxy-3-[4-(5-(3,5-dichloro-phenyl)-pent-2-en-4-ynyloxy)-phenyl]-propionate was hydrolysed as described in Example 2 to give the title compound.

$^1$H NMR (300 MHz, CDCl$_3$) δ: 1.19 (t, 3H), 2.88–3.12 (m, 2H), 3.37–3.50 (m, 1H), 3.65–3.70 (m, 1H), 4.05 (m, 1H), 4.70 (dd, 2H, J=1.5 and 5 Hz), 6.1 (dt, 1H, J=1.5 and 16 Hz), 6.45 (dt, 1H, J=5 and 16 Hz), 6.85 (d, 2H), 7.18 (d, 2H), 7.30 (s, 3H).

Example 21

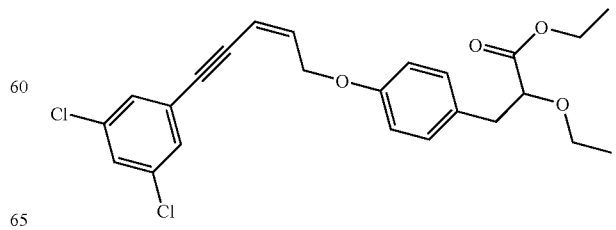

Ethyl (Z)-(S)-2-ethoxy-3-[4-(3-methyl-5-(3,5-dichloro-phenyl)-pent-2-en-4-ynyloxy)-phenyl]-propionate a)

(Z)-5-(3,5-Dichloro-phenyl)-pent-2-en-4-ynoic acid ethyl ester was made from cis-3-iodo acrylic acid ethyl ester (*Can J Chem,* 72 (8), 1816–1819, 1994). (4 g) using the conditions described in example 19 c. Yield 4.62 g.

$^1$H NMR (300 MHz, CDCl$_3$) δ: 1.4 (t, 3H), 4.3 (q, 2H), 6.2 (d, 1H, J=11 Hz), 6.34 (d, 1H, J=11 Hz), 7.32 (s, 1H) 7.4 (s, 2H).

b)

(Z)-5-(3,5-dichloro-phenyl)-pent-2-en-4-yn-1-ol was made from (Z)-5-(3,5-dichloro-phenyl)-pent-2-en-4-ynoic acid ethyl ester (4.6 g) using the conditions described in example 19 d. Yield 3.63 g.

$^1$H NMR (300 MHz, CDCl$_3$) δ: 4.4 (dd, 2H, J=1.5 and 6.5 Hz), 5.75 (dt, 1H, J=1.5 and 11 Hz), 6.21 (dt, 1H, J=6.5 and 11 Hz), 7.3 (s, 3H).

c)

The title compound was from (Z)-5-(3,5-dichloro-phenyl)-pent-2-en-4-yn-1-ol (300 mg, 1.32 mmol) using the conditions described in example 19 e. Yield 180 mg yield.

$^1$H NMR (300 MHz, CDCl$_3$) δ: 1.12 (t, 3H), 1.2 (t, 3H), 2.9 (d, 2H), 3.26–3.44 (m, 1H), 3.51–3.69 (m, 1H), 3.94 (t, 1H), 4.14 (q, 2H), 4.85 (dd, 2H, J=1.8 and 6.3 Hz), 5.87 (dt, 1H, J=1.8 and 11 Hz), 6.25 (dt, 1H, J=6.3 and 11 Hz), 6.82 (d, 2H), 7.15 (d, 2H), 7.33 (m, 3H).

Example 22

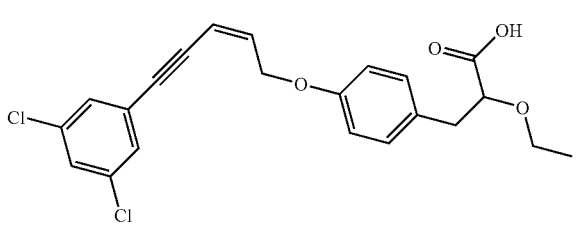

(Z)-(S)-2-ethoxy-3-[4-(3-methyl-5-(3,5-dichloro-phenyl)-pent-2-en-4-ynyloxy)-phenyl]-propionic acid Ethyl (Z)-(S)-2-ethoxy-3-[4-(3-methyl-5-(3,5-dichloro-phenyl)-pent-2-en-4-ynyloxy)-phenyl]-propionate was hydrolysed as described in Example 2 to give the title compound. Yield 100 mg.

$^1$H NMR (300 MHz, DMSO-D$_6$) δ: 1.16 (t, 3H), 2.85–3.05 (m, 2H), 3.3–3.45 (m, 1H), 3.6–3.7 (m, 1H), 4.06 (m, 1H), 4.9 (dd, 2H, J=1.8 and 6.2 Hz), 6.1 (dt, 1H, J=1.8 and 11 Hz), 6.45 (dt, 1H, J=6.2 and 11 Hz), 6.93 (d, 2H), 7.20 (d, 2H), 7.65 (d, 2H), 7.71 (d, 1H).

Example 23

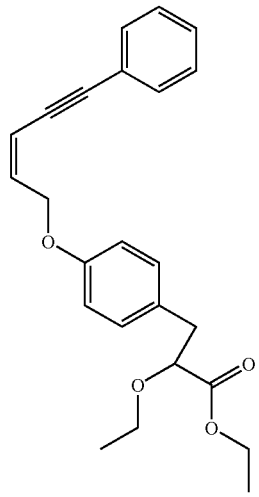

(Z)-(S)-2-Ethoxy-3-[4-(5-phenyl-pent-2-en-4-ynyloxy)-phenyl]-propionic acid ethyl ester a)

(Z)-5-phenyl-pent-2-en-4-ynoic acid ethyl ester was made from cis-3-iodo acrylic acid ethyl ester (2 g) and phenylacetylene using the conditions described in example 19 c. Yield 1.24 g.

$^1$H NMR (300 MHz, CDCl$_3$) δ: 1.3 (t, 3H), 4.25 (q, 2H), 6.12 (d, 1H, J$_{cis}$=11.3 Hz), 6.35 (d, 1H, J$_{cis}$=11.3 Hz), 7.36 (m, 3H) 7.53 (m, 2H).

b)

(Z)-5-phenyl-pent-2-en-4-yn-1-ol was made from (Z)-5-phenyl-pent-2-en-4-ynoic acid ethyl ester (1.0 g) using the conditions described in example 19 d. Yield 0.7 g.

$^1$H NMR (300 MHz, CDCl$_3$) δ: 4.5 (dd, 2H, J=1.5 and 6.5 Hz), 5.80 (dt, 1H, J=1.5 and 10.5 Hz), 6.14 (dt, 1H, J=6.4 and 10.5 Hz), 7.31 (m, 3H), 7.43 (m, 2H).

c)

The title compound was prepared from (Z)-5-phenyl-pent-2-en-4-yn-1-ol (200 mg, 1.3 mmol) using the conditions described in example 19 e. Yield 380 mg.

$^1$H NMR (300 MHz, CDCl$_3$) δ: 1.2 (dt, 6H), 2.98 (d, 2H), 3.3–3.41 (m, 1H), 3.53–3.68 (m, 1H), 3.95 (t, 1H), 4.18 (q, 2H), 4.9 (dd, 2H, J=1.6 and 6.4 Hz), 5.95 (dt, 1H, J=1.6 and 11 Hz), 6.2 (dt, 1H, J=6.4 and 11 Hz), 6.89 (d, 2H), 7.17 (d, 2H), 7.35 (m, 3H)), 7.47 (m, 2H).

Example 24

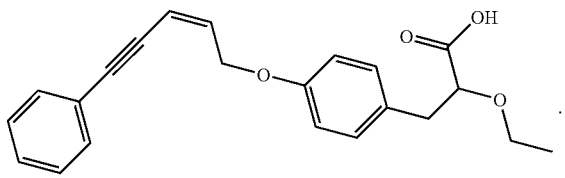

(Z)-(S)-2-Ethoxy-3-[4-(5-phenyl-pent-2-en-4-yny-loxy)-phenyl]-propionic acid

Ethyl (Z)-(S)-2-ethoxy-3-[4-(phenyl-pent-2-en-4-yny-loxy)-phenyl]-propionate was hydrolysed as described in Example 2 to give the title compound. Yield 264 mg. $^1$H NMR (300 MHz, DMSO-D$_6$) δ: 1.15 (t, 3H), 2.8–3.0 (m, 2H), 3.3–3.4 (m, 1H), 3.5–3.65 (m, 1H), 3.96 (m, 1H), 4.89 (dd, 2H, J=1.6 and 6.3 Hz), 6.08 (dt, 1H, J=1.6 and 11 Hz), 6.3 (dt, 1H, J=6.3 and 11 Hz), 6.9 (d, 2H), 7.20 (d, 2H), 7.4 (m, 3H), 7.5 (m, 2H).

Example 25

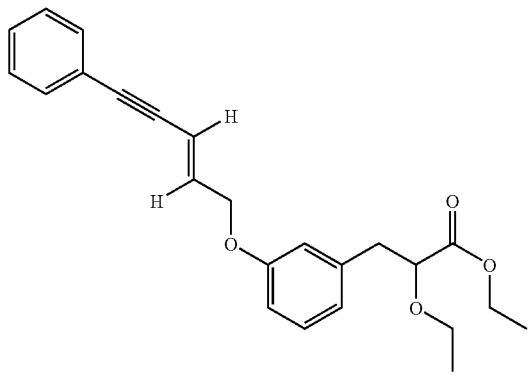

(E)-(RS)-2-Ethoxy-3-[3-(5-phenyl-pent-2-en-4-yny-loxy)-phenyl]-propionic acid ethyl ester a)
NaH 60% in paraffin oil (1.18 g, 29.5 mmol) was added to a solution of diethoxyphosphoryl-ethoxy-ethylacetate (7.46 g, 27.8 mmol)) in dry THF (40 mL) at 0° C. 3-Ben-zyloxybenzaldehyde (ALDRICH) (5.0 g, 23.6 mmol) dissolved in dry THF (20 mL) was added dropwise keeping the temperature below 10° C. The reaction mixture was allowed to reach room temperature followed by the addition of water. The product was extracted into MTBE, and the combined organic phases dried (Na$_2$SO$_4$), filtered and evaporated to give 7.6 g (99%) of (E,Z)-3-(3-benzyloxyphenyl)-2-ethoxy-acrylic acid ethyl ester as a yellow oil.

$^1$H NMR (CDCl$_3$, 400 MHz) δ: 1.09 (t), 1.34 (t), 1.37 (t), 3.92 (q), 3.98 (q), 4.12 (q), 4.30 (q), 5.04 (s), 5.09 (s), 6.95 (s), 7.26 (s), 7.2–7.5 (m).

b)
(E,Z)-3-(3-Benzyloxyphenyl)-2-ethoxyacrylic acid ethyl ester (6.8 g) dissolved in ethyl acetate (40 mL) was hydrogenated at 10 bar using Pd/C (10%) (1.08 g) until the reaction was shown to be completed by HPLC. The reaction mixture was filtered through a pad of celite and the solvent evaporated. The product was purified by column chromatography eluting with ethyl acetate/heptane 1:2 to give 3.1 g (62%) of (R,S)-2-ethoxy-3-hydroxyphenyl)propanoic acid ethyl ester.

$^1$H NMR (CDCl$_3$, 400 MHz) δ: 1.16 (t, 3H), 1.23 (t, 3H), 2.97–2.95 (m, 2H), 3.41–3.33 (dq, 1H), 3.65–3.57 (dq, 1H), 4.02(t, 1H), 4.17 (q, 2H), 5.33 (s, 1H), 6.81–6.70 (m, 3H), 7.15 (t, 1H). $^{13}$C-NMR (75 MHz, CDCl$_3$) δ 14.51, 15.36, 39,58, 61,48, 66,74, 80.52, 114.15, 116.87, 121.79, 129.81, 139.07, 156.20, 173.27. MS m/z (MH$^+$) 239.2. Elemental analysis: Anal. Calcd. for C$_{13}$H$_{18}$O$_4$: C, 65.53; H, 7.61%. Found: C, 65.98; H, 7.96.

c)
The title compound (120 mg, 63%) was prepared from (R,S)-2-ethoxy-3-(3-hydroxyphenyl)propanoic acid ethyl ester (120 mg, 0.5 mmol) and (E)-5-phenyl-pent-2-en-4-yn-1-ol (example 1, method 1 b)(79 mg, 0.5 mmol), by a procedure analogous to that described in example 1 (method 1c).

Example 26

Synthesis of Lys$^{26}$(N$^ε$-tetradecanoyl)-GLP-1(7-37).

The title compound was synthesised from GLP-1(7-37). A mixture of GLP-1(7-37) (25 mg, 7.45 μm), EDPA (26.7 mg, 208 μm), NMP (520 μl) and water (260 μl) was gently shaken for 5 min. at room temperature. To the resulting mixture was added a solution of Myr-ONSu (2.5 mg, 7.67 μm) in NMP (62.5 μl), the reaction mixture was gently shaken for 5 min. at room temperature and then allowed to stand for 20 min. An additional amount of Myr-ONSu (2.5 mg, 7.67 μm) in NMP (62.5 μl) was added and the resulting mixture gently shaken for 5 min. After a total reaction time of 40 min. the reaction was quenched by the addition of a solution of glycine (12.5 mg, 166 μmol) in 50% aqueous ethanol (12.5 ml). The title compound was isolated from the reaction mixture by HPLC using a cyanopropyl column (Zorbax 300SB-CN) and a standard acetonitrile/TFA system, yield: 1.3 mg (corresponding to 4.9% of the theoretical yield). The column was heated to 65° C. and the acetonitrile gradient was 0–100% in 60 minutes. The isolated product was analysed by PDMS and the m/z value for the protonated molecular ion was found to be 3567.9±3. The resulting molecular weight is thus 3566.9±3 amu (theoretical value: 3565.9 amu). The position of acylation (Lys26) was verified by enzymatic cleavage of the title compound with *Staphylococcus aureus* V8 protease and subsequent mass determination of the peptide fragments by PDMS.

In addition to the title compound two other GLP-1 derivatives were isolated from the reaction mixture by using the same chromatographic column and a more shallow gradient (35–38% acetonitrile in 60 minutes), see Examples 2 and 3.

Example 27

Synthesis of Lys$^{34}$(N$^ε$-tetradecanoyl)-GLP-1(7-37)

The title compound was isolated by HPLC from the reaction mixture described in Example 1. PDMS analysis yielded a protonated molecular ion at m/z 3567.7±3. The molecular weight is thus found to be 3566.7±3 amu (theoretical value: 3565.9 amu). The acylation site was determined on the basis of the fragmentation pattern.

Example 28

Synthesis of Lys$^{26,34}$-bis(N-tetradecanoyl)-GLP-1 (7-37)

The title compound was isolated by HPLC from the reaction mixture described in Example 1. PDMS analysis yielded a protonated molecular ion at m/z 3778.4±3. The molecular weight is thus found to be 3777.4±3 amu (theoretical value: 3776.1 amu).

Example 29

Synthesis of Lys$^{26}$(N$^\epsilon$-tetradecanoyl)Arg$^{34}$-GLP-1 (7-37)

The title compound was synthesised from Arg$^{34}$-GLP-1 (7-37). A mixture of Arg$^{34}$-GLP-1(7-37) (5 mg, 1.47 μm), EDPA (5.3 mg, 41.1 μm), NMP (105 μl) and water (50 μl) was gently shaken for 5 min. at room temperature. To the resulting mixture was added a solution of Myr-ONSu (0.71 mg, 2.2 μm) in NMP (17.8 μl), the reaction mixture was gently shaken for 5 min. at room temperature and then allowed to stand for 20 min. After a total reaction time of 30 min. the reaction was quenched by the addition of a solution of glycine (25 mg, 33.3 μm) in 50% aqueous ethanol (2.5 ml). The reaction mixture was purified by HPLC as described in Example 1. PDMS analysis yielded a protonated molecular ion at m/z 3594.9±3. The molecular weight is thus found to be 3593.9±3 amu (theoretical value: 3593.9 amu).

Example 30

Synthesis of Gly$^8$Arg$^{26,34}$Lys$^{36}$(N$^\epsilon$-tetradecanoyl)-GLP-1 (7-37)

The title compound was synthesised from Gly$^8$Arg$^{26,34}$Lys$^{36}$-GLP-1(7-37) which was purchased from QCB. A mixture of Gly$^8$Arg$^{26,34}$Lys$^{36}$-GLP-1(7-37) (1.3 mg, 0.39 μm), EDPA (1.3 mg, 10 μm), NMP (125 μl) and water (30 μl) was gently shaken for 5 min. at room temperature. To the resulting mixture was added a solution of Myr-ONSu (0.14 mg, 0.44 μm) in NMP (3.6 ml), the reaction mixture was gently shaken for 15 min. at room temperature. The reaction was quenched by the addition of a solution of glycine (0.1 mg, 1.33 μm) in 50% aqueous ethanol (10 μl). The reaction mixture was purified by HPLC, and the title compound (60 μg, 4%) was isolated.

Example 31

Synthesis of Arg$^{26,34}$Lys$^{36}$ (N-tetradecanoyl)-GLP-1(7-37)-OH

A mixture of Arg$^{26,34}$Lys$^{36}$-GLP-1(7-37)-OH (5.0 mg, 1.477 μmol), EDPA (5.4 mg, 41.78 μmol), NMP (105 μl) and water (50 μl) was gently shaken for 5 min. at room temperature. To the resulting mixture was added a solution of Myr-ONSu (0.721 mg, 2.215 μmol) in NMP (18 μl). The reaction mixture was gently shaken for 5 min. at room temperature, and then allowed to stand for an additional 45 min. at room temperature. The reaction was quenched by the addition of a solution of glycine (2.5 mg, 33.3 μmol) in 50% aqueous ethanol (250 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (1.49 mg, 28%) was isolated, and the product was analysed by PDMS. The m/z value for the protonated molecular ion was found to be 3595±3. The resulting molecular weight is thus 3594±3 amu (theoretical value 3594 amu).

Example 32

Synthesis of Lys$^{26,34}$bis(N$^\epsilon$-(ω-carboxynonadecanoyl))-GLP-1(7-37)-OH A mixture of GLP-1(7-37)-OH (70 mg, 20.85 μmol), EDPA (75.71 mg, 585.8 μmol), NMP (1.47 ml) and water (700 μL) was gently shaken for 10 min. at room temperature. To the resulting mixture was added a solution of HOOC-(CH$_2$)$_{18}$-COONSu (27.44 mg, 62.42 μmol) in NMP (686 μl), the reaction mixture was gently shaken for 5 min. at room temperature, and then allowed to stand for an additional 50 min. at room temperature. The reaction was quenched by the addition of a solution of glycine (34.43 mg, 458.7 μmol) in 50% aqueous ethanol (3.44 ml). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (8.6 mg, 10%) was isolated, and the product was analysed by PDMS. The m/z value for the protonated molecular ion was found to be 4006±3. The resulting molecular weight is thus 4005±3 amu (theoretical value 4005 amu).

Example 33

Synthesis of Arg$^{26,34}$Lys$^{36}$(N$^\epsilon$-(ω-carboxynonadecanoyl))-GLP-1(7-36)-OH A mixture of Arg$^{26,34}$Lys$^{36}$-GLP-1(7-36)-OH (5.06 mg, 1.52 μmol), EDPA (5.5 mg, 42.58 μmol), NMP (106 μl) and water (100 μl) was gently shaken for 5 min. at room temperature. To the resulting mixture was added a solution of HOOC-(CH$_2$)$_{18}$-COONSu (1.33 mg, 3.04 μmol) in NMP (33.2 μl), the reaction mixture was gently shaken for 5 min. at room temperature, and then allowed to stand for an additional 2.5 h at room temperature. The reaction was quenched by the addition of a solution of glycine (2.50 mg, 33.34 μmol) in 50% aqueous ethanol (250 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.46 mg, 8%) was isolated, and the product was analysed by PDMS. The m/z value for the protonated molecular ion was found to be 3652±3. The resulting molecular weight is thus 3651±3 amu (theoretical value 3651 amu).

Example 34

Synthesis of Arg$^{26,34}$Lys$^{38}$(N$^\epsilon$-(ω-carboxynonadecanoyl))-GLP-1(7-38)-OH A mixture of Arg$^{26,34}$Lys$^{38}$-GLP-1(7-38)-OH (5.556 mg, 1.57 μmol), EDPA (5.68 mg, 43.96 μmol), NMP (116.6 μl) and water (50 μl) was gently shaken for 10 min. at room temperature. To the resulting mixture was added a solution HOOC-(CH$_2$)$_{18}$-COONSu (1.38 mg, 3.14 μmol) in NMP (34.5 μl), the reaction mixture was gently shaken for 5 min. at room temperature, and then allowed to stand for an additional 2.5 h at room temperature. The reaction was quenched by the addition of a solution of glycine (2.5 mg, 33.3 μmol) in 50% aqueous ethanol (250 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.7 mg, 12%) was isolated, and the product was analysed by PDMS. The m/z value for the protonated molecular ion was found to be 3866±3. The resulting molecular weight is thus 3865±3 amu (theoretical value 3865 amu).

Example 35

Synthesis of $Arg^{34}Lys^{26}$ ($N^{\epsilon}$-($\omega$-carboxynonadecanoyl))-GLP-1(7-37)-OH A mixture of $Arg^{34}$-GLP-1(7-37)-OH (5.04 mg, 1.489 μmol), EDPA (5.39 mg, 41.70 μmol), NMP (105 μl) and water (50 μl) was gently shaken for 10 min. at room temperature. To the resulting mixture was added a solution HOOC-$(CH_2)_{18}$-COONSu (1.31 mg, 2.97 μmol) in NMP (32.8 μl), the reaction mixture was gently shaken for 5 min. at room temperature, and then allowed to stand for an additional 30 min. at room temperature. The reaction was quenched by the addition of a solution of glycine (2.46 mg, 32.75 μmol) in 50% aqueous ethanol (246 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (1.2 mg, 22%) was isolated, and the product was analysed by PDMS. The m/z value for the protonated molecular ion was found to be 3709±3. The resulting molecular weight is thus 3708±3 amu (theoretical value 3708 amu).

Example 36

Synthesis of $Arg^{34}Lys^{26}$ ($N^{\epsilon}$-($\omega$-carboxyheptadecanoyl))-GLP-1(7-37)-OH A mixture of $Arg^{34}$-GLP-1(7-37)-OH (5.8 mg, 1.714 μmol), EDPA (6.20 mg, 47.99 μmol), NMP (121.8 μl) and water (58 μl) was gently shaken for 10 min. at room temperature. To the resulting mixture was added a solution HOOC-$(CH_2)_{16}$-COONSu (2.11 mg, 5.142 μmol) in NMP (52.8 μl), the reaction mixture was gently shaken for 5 min. at room temperature, and then allowed to stand for an additional 2 h at room temperature. The reaction was quenched by the addition of a solution of glycine (2.83 mg, 37.70 μmol) in 50% aqueous ethanol (283 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.81 mg, 13%) was isolated, and the product was analysed by PDMS. The m/z value for the protonated molecular ion was found to be 3681±3. The resulting molecular weight is thus 3680±3 amu (theoretical value 3680 amu).

Example 37

Synthesis of $Arg^{26,34}Lys^{36}$ ($N^{\epsilon}$-($\omega$-carboxyheptadecanoyl))-GLP-1(7-37)-OH A mixture of $Arg^{26,34}Lys^{36}$-GLP-1(7-37)-OH (3.51 mg, 1.036 μmol), EDPA (3.75 mg, 29.03 μmol), NMP (73.8 μl) and water (35 μl) was gently shaken for 10 min. at room temperature. To the resulting mixture was added a solution HOOC-$(CH_2)_{16}$-COONSu (1.27 mg, 3.10 μmol) in NMP (31.8 μl), the reaction mixture was gently shaken for 5 min. at room temperature, and then allowed to stand for an additional 2 h and 10 min. at room temperature. The reaction was quenched by the addition of a solution of glycine (1.71 mg, 22.79 μmol) in 50% aqueous ethanol (171 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.8 mg, 21%) was isolated, and the product was analysed by PDMS. The m/z value for the protonated molecular ion was found to be 3682±3. The resulting molecular weight is thus 3681±3 amu (theoretical value 3681amu).

Example 38

Synthesis of $Arg^{26,34}Lys^{38}$($N^{\epsilon}$-($\omega$-carboxyheptadecanoyl))-GLP-1(7-38)-OH A mixture of $Arg^{26,34}Lys^{38}$-GLP-1(7-38)-OH (5.168 mg, 1.459 μmol), EDPA (5.28 mg, 40.85 μmol), NMP (108.6 μl) and water (51.8 μl) was gently shaken for 10 min. at room temperature. To the resulting mixture was added a solution HOOC-$(CH_2)_{16}$-COONSu (1.80 mg, 4.37 μmol) in NMP (45 μl), the reaction mixture was gently shaken for 10 min. at room temperature, and then allowed to stand for an additional 2 h and 15 min. at room temperature. The reaction was quenched by the addition of a solution of glycine (2.41 mg, 32.09 μmol) in 50% aqueous ethanol (241 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.8 mg, 14%) was isolated, and the product was analysed by PDMS. The m/z value for the protonated molecular ion was found to be 3838±3. The resulting molecular weight is thus 3837±3 amu (theoretical value 3837 amu).

Example 39

Synthesis of $Arg^{26,34}Lys^{36}$ ($N^{\epsilon}$-($\omega$-carboxyheptadecanoyl))-GLP-1(7-36)-OH A mixture of $Arg^{26,34}Lys^{36}$-GLP-1(7-36)-OH (24.44 mg, 7.34 μmol), EDPA (26.56 mg, 205.52 μmol), NMP (513 μl) and water (244.4 μl) was gently shaken for 5 min. at room temperature. To the resulting mixture was added a solution HOOC-$(CH_2)_{16}$-COONSu (9.06 mg, 22.02 μmol) in NMP (1.21 ml), the reaction mixture was gently shaken for 5 min. at room temperature, and then allowed to stand for an additional 30 min. at room temperature. The reaction was quenched by the addition of a solution of glycine (12.12 mg, 161.48 μmol) in 50% aqueous ethanol (1.21 ml). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (7.5 mg, 28%) was isolated, and the product was analysed by PDMS. The m/z value for the protonated molecular ion was found to be 3625±3. The resulting molecular weight is thus 3624±3 amu (theoretical value 3624 amu).

Example 40

Synthesis of Arg$^{26,34}$Lys$^{36}$ (N$^\epsilon$-(ω-carboxyundecanoyl))-GLP-1(7-37)-OH A mixture of Arg$^{26,34}$Lys$^{36}$-GLP-1(7-37)-OH (4.2 mg, 1.24 μmol), EDPA (4.49 mg, 34.72 μmol), NMP (88.2 μl) and water (42 μl) was gently shaken for 10 min. at room temperature. To the resulting mixture was added a solution HOOC-(CH$_2$)$_{10}$-COONSu (1.21 mg, 3.72 μmol) in NMP (30.25 μl), the reaction mixture was gently shaken for 5 min. at room temperature, and then allowed to stand for an additional 40 min. at room temperature. The reaction was quenched by the addition of a solution of glycine (2.04 mg, 27.28 μmol) in 50% aqueous ethanol (204 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.8 mg, 18%) was isolated, and the product was analysed by PDMS. The m/z value for the protonated molecular ion was found to be 3598±3. The resulting molecular weight is thus 3597±3 amu (theoretical value 3597 amu).

Example 41

Synthesis of Arg$^{26,34}$Lys$^{38}$(N$^\epsilon$-(ω-carboxyundecanoyl))-GLP-1(7-38)-OH A mixture of Arg$^{26,34}$Lys$^{38}$-GLP-1(7-38)-OH (5.168 mg, 1.46 μmol), EDPA (5.28 mg, 40.88 μmol), NMP (108.6 μl) and water (51.7 μl) was gently shaken for 10 min. at room temperature. To the resulting mixture was added a solution HOOC-(CH$_2$)$_{10}$-COONSu (1.43 mg, 4.38 μmol) in NMP (35.8 μl), the reaction mixture was gently shaken for 5 min. at room temperature, and then allowed to stand for an additional 50 min. at room temperature. The reaction was quenched by the addition of a solution of glycine (2.41 mg, 32.12 μmol) in 50% aqueous ethanol (241 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.85 mg, 16%) was isolated, and the product was analysed by PDMS. The m/z value for the protonated molecular ion was found to be 3753±3. The resulting molecular weight is thus 3752±3 amu (theoretical value 3752 amu).

Example 42

Synthesis of Lys$^{26,34}$bis(N$^\epsilon$-(ω-carboxyundecanoyl))-GLP-1(7-37)-OH A mixture of GLP-1(7-37)-OH (10.0 mg, 2.98 μmol), EDPA (10.8 mg, 83.43 μmol), NMP (210 μl) and water (100 μl) was gently shaken for 10 min. at room temperature. To the resulting mixture was added a solution HOOC-(CH$_2$)$_{10}$-COONSu (2.92 mg, 8.94 μmol) in NMP (73 μl), the reaction mixture was gently shaken for 5 min. at room temperature, and then allowed to stand for an additional 50 min. at room temperature. The reaction was quenched by the addition of a solution of glycine (4.92 mg, 65.56 μmol) in 50% aqueous ethanol (492 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (1.0 mg, 9%) was isolated, and the product was analysed by PDMS. The m/z value for the protonated molecular ion was found to be 3781±3. The resulting molecular weight is thus 3780±3 amu (theoretical value 3780 amu).

Example 43

Synthesis of Arg$^{26,34}$Lys$^{36}$ (N$^\epsilon$-(ω-carboxyundecanoyl))-GLP-1(7-36)-OH A mixture of Arg$^{26,34}$Lys$^{36}$-GLP-1(7-36)-OH (15.04 mg, 4.52 μmol), EDPA (16.35 mg, 126.56 μmol), NMP (315.8 μl) and water (150.4 μl) was gently shaken for 10 min. at room temperature. To the resulting mixture was added a solution HOOC-(CH$_2$)$_{10}$-COONSu (4.44 mg, 13.56 μmol) in NMP (111 μl), the reaction mixture was gently shaken for 5 min. at room temperature, and then allowed to stand for an additional 40 min. at room temperature. The reaction was quenched by the addition of a solution of glycine (7.5 mg, 99.44 μmol) in 50% aqueous ethanol (750 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (3.45 mg, 22%) was isolated, and the product was analysed by PDMS. The m/z value for the protonated molecular ion was found to be 3540±3. The resulting molecular weight is thus 3539±3 amu (theoretical value 3539 amu).

Example 44

Synthesis of Arg$^{34}$Lys$^{26}$ (N$^\epsilon$-(ω-carboxyundecanoyl))-GLP-1(7-37)-OH A mixture of Arg$^{34}$-GLP-1(7-37)-OH (5.87 mg, 1.73 μmol), EDPA (6.27 mg, 48.57 μmol), NMP (123.3 μl) and water (58.7 μl) was gently shaken for 10 min. at room temperature. To the resulting mixture was added a solution HOOC-(CH$_2$)$_{10}$-COONSu (1.70 mg, 5.20 μmol) in NMP (42.5 μl), the reaction mixture was gently shaken for 5 min. at room temperature, and then allowed to stand for an additional 40 min. at room temperature. The reaction was quenched by the addition of a solution of glycine (2.86 mg, 286 μmol) in 50% aqueous ethanol (286 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (1.27 mg, 20%) was isolated, and the product was analysed by PDMS. The m/z value for the protonated molecular ion was found to be 3597±3. The resulting molecular weight is thus 3596±3 amu (theoretical value 3596 amu).

Example 45

Synthesis of Arg$^{34}$Lys$^{26}$ (N$^\epsilon$-(ω-carboxyheptanoyl))-GLP-1(7-37)-OH A mixture of Arg$^{34}$-GLP-1(7-37)-OH (4.472 mg, 1.32 μmol), EDPA (4.78 mg, 36.96 μmol), NMP (94 μl) and water (44.8 μl) was gently shaken for 5 min. at room temperature. To the resulting mixture was added a solution HOOC-(CH$_2$)$_6$-COONSu (1.07 mg, 3.96 μmol) in NMP (26.8 µl), the reaction mixture was gently shaken for 5 min. at room temperature, and then allowed to stand for an additional 1 h and 50 min. at room temperature. The reaction was quenched by the addition of a solution of glycine (2.18 mg, 29.04 µmol) in 50% aqueous ethanol (218 µl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.5 mg, 11%) was isolated, and the product was analysed by PDMS. The m/z value for the protonated molecular ion was found to be 3540±3. The resulting molecular weight is thus 3539±3 amu (theoretical value 3539 amu).

Example 46

Synthesis of $Arg^{26,34}Lys^{38}(N^{\epsilon}$-($\omega$-carboxyheptanoyl))-GLP-1(7-38)-OH A mixture of $Arg^{26,34}Lys^{38}$-GLP-1(7-38)-OH (5.168 mg, 1.459 µmol), EDPA (5.28 mg, 40.85 µmol), NMP (108.6 µl) and water (51.6 µl) was gently shaken for 10 min. at room temperature. To the resulting mixture was added a solution $HOOC$-$(CH_2)_6$-COONSu (1.18 mg, 4.37 µmol) in NMP (29.5 µl), the reaction mixture was gently shaken for 5 min. at room temperature, and then allowed to stand for an additional 1 h and 50 min. at room temperature. The reaction was quenched by the addition of a solution of glycine (2.40 mg, 32.09 µmol) in 50% aqueous ethanol (240 µl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.5 mg, 9%) was isolated, and the product was analysed by PDMS. The m/z value for the protonated molecular ion was found to be 3697±3. The resulting molecular weight is thus 3695±3 amu (theoretical value 3695 amu).

Example 47

Synthesis of $Arg^{26,34}Lys^{36}$ ($N^{\epsilon}$-($\omega$-carboxyheptanoyl))-GLP-1(7-37)-OH A mixture of $Arg^{26,34}Lys^{36}$-GLP-1(7-37)-OH (5.00 mg, 1.47 µmol), EDPA (5.32 mg, 41.16 µmol), NMP (105 µl) and water (50 µl) was gently shaken for 5 min. at room temperature. To the resulting mixture was added a solution $HOOC$-$(CH_2)_6$-COONSu (1.19 mg, 4.41 µmol) in NMP (29.8 µl), the reaction mixture was gently shaken for 5 min. at room temperature, and then allowed to stand for an additional 2 h at room temperature. The reaction was quenched by the addition of a solution of glycine (2.42 mg, 32.34 µmol) in 50% aqueous ethanol (242 µl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.78 mg, 15%) was isolated, and the product was analysed by PDMS. The m/z value for the protonated molecular ion was found to be 3542±3. The resulting molecular weight is thus 3541±3 amu (theoretical value 3541 amu).

Example 48

Synthesis of $Arg^{26,34}Lys^{36}$ ($N^{\epsilon}$-($\omega$-carboxyheptanoyl))-GLP-1(7-36)-OH A mixture of $Arg^{26,34}Lys^{36}$-GLP-1(7-36)-OH (5.00 mg, 1.50 µmol), EDPA (5.44 mg, 42.08 µmol), NMP (210 µl) and water (50 µl) was gently shaken for 5 min. at room temperature. To the resulting mixture was added a solution $HOOC$-$(CH_2)_6$-COONSu (1.22 mg, 4.5 µmol) in NMP (30.5 µl), the reaction mixture was gently shaken for 5 min. at room temperature, and then allowed to stand for an additional 2 h at room temperature. The reaction was quenched by the addition of a solution of glycine (2.47 mg, 33.0 µmol) in 50% aqueous ethanol (247 µl). The reaction mixture was purified by column chromatography using a cyanopropyl column (Zorbax 300SB-CN) and a standard acetonitrile/ TFA system. The column was heated to 65° C. and the acetonitrile gradient was 0–100% in 60 minutes. The title compound (0.71 mg, 14%) was isolated, and the product was analysed by PDMS. The m/z value for the protonated molecular ion was found to be 3484±3. The resulting molecular weight is thus 3483±3 amu (theoretical value 3483 amu).

Example 49

Synthesis of $Lys^{26,34}bis(N^{\epsilon}$-($\omega$-carboxyheptanoyl))-GLP-1(7-37)-OH A mixture of GLP-1(7-37)-OH (10 mg, 2.5 µmol), EDPA (10.8 mg, 83.56 µmol), NMP (210 µl) and water (100 µl) was gently shaken for 10 min. at room temperature. To the resulting mixture was added a solution $HOOC$-$(CH_2)_6$-COONSu (2.42 mg, 8.92 µmol) in NMP (60.5 µl), the reaction mixture was gently shaken for 5 min. at room temperature, and then allowed to stand for an additional 2 h and 35 min. at room temperature. The reaction was quenched by the addition of a solution of glycine (4.92 mg, 65.54 µmol) in 50% aqueous ethanol (492 µl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (2.16 mg, 24%) was isolated, and the product was analysed by PDMS. The m/z value for the protonated molecular ion was found to be 3669±3. The resulting molecular weight is thus 3668±3 amu (theoretical value 3668 amu).

Example 50

Synthesis of $Arg^{34}Lys^{26}$ ($N^{\epsilon}$-($\omega$-carboxypentadecanoyl))-GLP-1(7-37)-OH A mixture of $Arg^{34}$-GLP-1(7-37)-OH (4.472 mg, 1.321 µmol), EDPA (4.78 mg, 36.99 µmol), NMP (93.9 µl) and water (44.7 µl) was gently shaken for 10 min. at room temperature. To the resulting mixture was added a solution $HOOC$-$(CH_2)_{14}$-COONSu (1.519 mg, 3.963 µmol) in NMP (38 µl), the reaction mixture was gently shaken for 5 min. at room temperature, and then allowed to stand for an additional 1 h at room temperature. The reaction was quenched by the addition of a solution of glycine (2.18 mg, 29.06 µmol) in 50% aqueous ethanol (218 µl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.58 mg, 12%) was isolated, and the product was analysed by PDMS. The m/z value for the protonated molecular ion was found to be 3654±3. The resulting molecular weight is thus 3653±3 amu (theoretical value 3653 amu).

Example 51

Synthesis of $Arg^{26,34}Lys^{36}$ ($N^{\epsilon}$-(ω-carboxyheptanoyl))-GLP-1(7-36)-OH A mixture of $Arg^{26,34}Lys^{36}$-GLP-1(7-36)-OH (5.00 mg, 1.50 μmol), EDPA (5.44 mg, 42.08 μmol), NMP (210 μl) and water (50 μl) was gently shaken for 5 min. at room temperature. To the resulting mixture was added a solution HOOC-$(CH_2)_{14}$-COONSu (1.72 mg, 4.5 μmol) in NMP (43 μl), the reaction mixture was gently shaken for 5 min. at room temperature, and then allowed to stand for an additional 1 h at room temperature. The reaction was quenched by the addition of a solution of glycine (2.48 mg, 33 μmol) in 50% aqueous ethanol (248 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.58 mg, 11%) was isolated, and the product was analysed by PDMS. The m/z value for the protonated molecular ion was found to be 3596±3. The resulting molecular weight is thus 3595±3 amu (theoretical value 3595 amu).

Example 52

Synthesis of lithocholic acid 2,5-dioxo-pyrrolidin-1-yl ester

To a mixture of lithocholic acid (5.44 g, 14.34 mmol), N-hydroxysuccinimide (1.78 g, 15.0 mmol), anhydrous THF (120 ml) and anhydrous acetonitrile (30 ml), kept at to 10° C., was added a solution of N,N'-dicyclohexylcarbodiimide (3.44 g, 16.67 mmol) in anhydrous THF. The reaction mixture was stirred at ambient temperature for 16 h, filtered and concentrated in vacuo. The residue was dissolved in dichloromethane (450 ml), washed with a 10% aqueous $Na_2CO_3$ solution (2×150 ml) and water (2×150 ml), and dried ($MgSO_4$). Filtered and the filtrate concentrated in vacuo to give a crystalline residue. The residue was recrystallised from a mixture of dichloromethane (30 ml) and n-heptane (30 ml to give the title compound_(3.46 g, 51%) as a crystalline solid.

Example 53

Synthesis of $Arg^{34}Lys^{26}$($N^{\epsilon}$-lithocholyl)-GLP-1(7-37)-OH

A mixture of $Arg^{34}$-GLP-1(7-37)-OH (4.472 mg, 1.32 μmol), EDPA (4.78 mg, 36.96 μmol), NMP (94 μl) and water (44.8 μl) was gently shaken for 10 min. at room temperature. To the resulting mixture was added a solution of lithocholic acid 2,5-dioxo-pyrrolidin-1-yl ester (1.87 mg, 3.96 μmol) in NMP (46.8 μl), the reaction mixture was gently shaken for 5 min. at room temperature, and then allowed to stand for an additional 1 h at room temperature. The reaction was quenched by the addition of a solution of glycine (2.18 mg, 29.04 μmol) in 50% aqueous ethanol (218 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (1.25 mg, 25%) was isolated, and the product was analysed by PDMS. The m/z value for the protonated molecular ion was found to be 3744+-3. The resulting molecular weight is thus 3743+-3 amu (theoretical value 3743 amu).

Example 54

Synthesis of $N^{\alpha}$-tetradecanoyl-Glu(ONSu)-$OBu^t$

To a suspension of H-Glu(OH)-$OBu^t$(2.5 g, 12.3 mmol), DMF (283 ml) and EDPA (1.58 g, 12.3 mmol) was added drop by drop a solution of Myr-ONSu (4.0 g, 12.3 mmol) in DMF (59 ml). The reaction mixture was stirred for 16 h at room temperature and then concentrated in vacuo to a total volume of 20 ml. The residue was partitioned between 5% aqueous citric acid (250 ml) and ethyl acetate (150 ml), and the phases were separated. The organic phase was concentrated in vacuo and the residue dissolved in DMF (40 ml). The resulting solution was added drop by drop to a 10% aqueous solution of citric acid (300 ml) kept at 0° C. The precipitated compound was collected and washed with iced water and dried in a vacuum drying oven. The dried compound was dissolved in DMF (23 ml) and HONSu (1.5 g, 13 mmol) was added. To the resulting mixture was added a solution of N,N'-dicyclohexylcarbodiimide (2.44 g, 11.9 mmol) in dichloromethane (47 ml). The reaction mixture was stirred for 16 h at room temperature, and the precipitated compound was filtered off. The precipitate was recrystallised from n-heptane/2-propanol to give the title compound (3.03 g, 50%).

Example 55

Synthesis of $Glu^{22,23,30}Arg^{26,34}Lys^{38}$($N^{\epsilon}$-(γ-glutamyl($N\alpha$-tetradecanoyl)))-GLP-1(7-38)-OH A mixture of $Glu^{22,23,30}Arg^{26,34}Lys^{38}$-GLP-1(7-38)-OH (1.0 mg, 0.272 μmol), EDPA (0.98 mg, 7.62 μmol), NMP (70 μl) and water (70 μl) was gently shaken for 5 min. at room temperature. To the resulting mixture was added a solution of $N^{\alpha}$-tetradecanoyl-Glu(ONSu)-$OBu^t$, prepared as described in Example 29, (0.41 mg, 0.816 μmol) in NMP (10.4 μl), the reaction mixture was gently shaken for 5 min. at room temperature, and then allowed to stand for an additional 45 min. at room temperature. The reaction was quenched by the addition of a solution of glycine (0.448 mg, 5.98 μmol) in 50% aqueous ethanol (45 μl). A 0.5% aqueous solution of ammonium acetate (0.9 ml) was added, and the resulting mixture was immobilised on a Varian 500 mg C8 Mega Bond Elut® cartridge, the immobilised compound washed with 5% aqueous acetonitrile (10 ml), and finally liberated from the cartridge by elution with TFA (10 ml). The eluate was concentrated in vacuo, and the reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.35 mg, 32%) was isolated, and the product was analysed by PDMS. The m/z value for the protonated molecular ion was found to be 4012±3. The resulting molecular weight is thus 4011±3 amu (theoretical value 4011 amu).

Example 56

Synthesis of Glu$^{23,26}$Arg$^{34}$Lys$^{38}$(N$^\epsilon$-(γglutamyl(N$^\alpha$-tetradecanoyl)))-GLP-1(7-38)-OH A mixture of Glu$^{23,26}$Arg$^{34}$Lys$^{38}$-GLP-1(7-38)-OH (6.07 mg, 1.727 µmol), EDPA (6.25 mg, 48.36 µmol), NMP (425 µl) and water (425 µl) was gently shaken for 5 min. at room temperature. To the resulting mixture was added a solution of N$^\alpha$-tetradecanoyl-Glu(ONSu)-OBu$^t$, prepared as described in example 29, (2.65 mg, 5.18 µmol) in NMP (66.3 µl), the reaction mixture was gently shaken for 5 min. at room temperature, and then allowed to stand for an additional 45 min. at room temperature. The reaction was quenched by the addition of a solution of glycine (2.85 mg, 38.0 µmol) in 50% aqueous ethanol (285 µl). A 0.5% aqueous solution of ammonium acetate (5.4 ml) was added, and the resulting mixture was immobilised on a Varian 500 mg C8 Mega Bond Elut® cartridge, the immobilised compound washed with 5% aqueous acetonitrile (10 ml), and finally liberated from the cartridge by elution with TFA (10 ml). The eluate was concentrated in vacuo, and the reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.78 mg, 12%) was isolated, and the product was analysed by PDMS. The m/z value for the protonated molecular ion was found to be 3854±3. The resulting molecular weight is thus 3853±3 amu (theoretical value 3853 amu).

Example 57

Synthesis of Lys$^{26,34}$-bis(N$^\epsilon$-(ω-carboxytridecanoyl))-GLP-1(7-37)-OH A mixture of GLP-1(7-37)-OH (30 mg, 8.9 µmol), EDPA (32.3 mg, 250 µmol), NMP (2.1 ml) and water (2.1 ml) was gently shaken for 5 min. at room temperature. To the resulting mixture was added a solution HOOC-(CH$_2$)$_{12}$-COONSu (12.7 mg, 35.8 µmol) in NMP (318 µl), the reaction mixture was gently shaken for 1 h and 40 min. at room temperature. The reaction was quenched by the addition of a solution of glycine (3.4 mg, 44.7 µmol) in 50% aqueous ethanol (335 µl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (10 mg, 29%) was isolated, and the product was analysed by PDMS. The m/z value for the protonated molecular ion was found to be 3840±3. The resulting molecular weight is thus 3839±3 amu (theoretical value 3839 amu).

Example 58

Synthesis of Lys$^{26,34}$-bis(N$^\epsilon$-(γ-glutamyl(N$^\alpha$-tetradecanoyl)))-GLP-1(7-37)-OH. (NNC 90-1167)

A mixture of GLP-1(7-37)-OH (300 mg, 79.8 µmol), EDPA (288.9 mg, 2.24 mmol), NMP (21 ml) and water (21 ml) was gently shaken for 5 min. at room temperature. To the resulting mixture was added a solution of N$^\alpha$-tetradecanoyl-Glu(ONSu)-OBu$^t$, prepared as described in Example 29, (163 mg, 319.3 µmol) in NMP (4.08 ml), the reaction mixture was gently shaken for 5 min. at room temperature, and then allowed to stand for an additional 1 h at room temperature. The reaction was quenched by the addition of a solution of glycine (131.8 mg, 1.76 mmol) in 50% aqueous ethanol (13.2 ml). A 0.5% aqueous solution of ammonium acetate (250 ml) was added, and the resulting mixture was divided into four equal portions. Each portion was eluted onto a Varian 500 mg C8 Mega Bond Elut® cartridge, the immobilised compound washed with 0.1% aqueous TFA (3.5 ml), and finally liberated from the cartridge by elution with 70% aqueous acetonitrile (4 ml). The combined eluates were diluted with 0.1% aqueous TFA (300 ml). The precipitated compound was collected by centrifugation, washed with 0.1% aqueous TFA (50 ml), and finally isolated by centrifugation. To the precipitate was added TFA (60 ml), and the resulting reaction mixture was stirred for 1 h and 30 min. at room temperature. Excess TFA was removed in vacuo, and the residue was poured into water (50 ml). The precipitated compound was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (27.3 mg, 8%) was isolated, and the product was analysed by PDMS. The m/z value for the protonated molecular ion was found to be 4036±3. The resulting molecular weight is thus 4035±3 amu (theoretical value 4035 amu).

Example 59

Synthesis of Arg$^{26,34}$Lys$^{38}$(N$^\epsilon$-(ω-carboxypentadecanoyl))-GLP-1(7-38)-OH A mixture of Arg$^{26,34}$Lys$^{38}$-GLP-1(7-38)-OH (30 mg, 8.9 µmol), EDPA (32.3 mg, 250 µmol), NMP (2.1 ml) and water (2.1 ml) was gently shaken for 5 min. at room temperature. To the resulting mixture was added a solution HOOC-(CH$_2$)$_{14}$-COONSu (13.7 mg, 35.8 µmol) in NMP (343 µl), the reaction mixture was gently shaken for 1 h at room temperature. The reaction was quenched by the addition of a solution of glycine (3.4 mg, 44.7 µmol) in 50% aqueous ethanol (335 µl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (4.8 mg, 14%) was isolated, and the product was analysed by PDMS. The m/z value for the protonated molecular ion was found to be 3894±3. The resulting molecular weight is thus 3893±3 amu (theoretical value 3893 amu).

Example 60

Synthesis of N$^\alpha$-hexadecanoyl-Glu(ONSu)-OBu$^t$

To a suspension of H-Glu(OH)-OBu$^t$(4.2 g, 20.6 mmol), DMF (500 ml) and EDPA (2.65 g, 20.6 mmol) was added drop by drop a solution of Pal-ONSu (7.3 g, 20.6 mmol) in DMF (100 ml). The reaction mixture was stirred for 64 h at room temperature and then concentrated in vacuo to a total volume of 20 ml. The residue was partitioned between 10% aqueous citric acid (300 ml) and ethyl acetate (250 ml), and the phases were separated. The organic phase was concentrated in vacuo and the residue dissolved in DMF (50 ml). The resulting solution was added drop by drop to a 10% aqueous solution of citric acid (500 ml) kept at 0° C. The precipitated compound was collected and washed with iced water and dried in a vacuum drying oven. The dried compound was dissolved in DMF (45 ml) and HONSu (2.15 g, 18.7 mmol) was added. To the resulting mixture was added a solution of N,N'-dicyclohexylcarbodiimide (3.5 g, 17 mmol) in dichloromethane (67 ml). The reaction mixture was stirred for 16 h at room temperature, and the precipitated compound was filtered off. The precipitate was recrystallised from n-heptane/2-propanol to give the title compound (6.6 g, 72%).

Example 61

Synthesis of Lys$^{26,34}$-bis(N$^\epsilon$-(ω-glutamyl(N$^\alpha$-hexadecanoyl)))-GLP-1(7-37)-OH A mixture of GLP-1(7-37)-OH (10 mg, 2.9 μmol), EDPA (10.8 mg, 83.4 μmol), NMP (0.7 ml) and water (0.7 ml) was gently shaken for 5 min. at room temperature. To the resulting mixture was added a solution of N$^\alpha$-hexadecanoyl-Glu(ONSu)-OBu$^t$, prepared as described in Example 33, (163 mg, 319.3 μmol) in NMP (4.08 ml), the reaction mixture was gently shaken 1 h and 20 min. at room temperature. The reaction was quenched by the addition of a solution of glycine (4.9 mg, 65.6 μmol) in 50% aqueous ethanol (492 μl). A 0.5% aqueous solution of ammonium-acetate (9 ml) was added, and the resulting mixture eluted onto a Varian 1 g C8 Mega Bond Elut® cartridge, the immobilised compound washed with 5% aqueous acetonitrile (10 ml), and finally liberated from the cartridge by elution with TFA (10 ml). The eluate was concentrated in vacuo, and the residue purified by column chromatography using a cyanopropyl column (Zorbax 300SB-CN) and a standard acetonitrile/TFA system. The column was heated to 65° C. and the acetonitrile gradient was 0–100% in 60 minutes. The title compound (2.4 mg, 20%) was isolated, and the product was analysed by PDMS. The m/z value for the protonated molecular ion was found to be 4092±3. The resulting molecular weight is thus 4091±3 amu (theoretical value 4091 amu).

Example 62

Synthesis of Arg$^{34}$Lys$^{26}$(N$^\epsilon$-(γ-glutamyl(N$^\alpha$-hexadecanoyl)))-GLP-1(7-37)-OH A mixture of Arg$^{34}$-GLP-1(7-37)-OH (3.7 mg, 1.1 μmol), EDPA (4.0 mg, 30.8 μmol), acetonitrile (260 μl) and water (260 μl) was gently shaken for 5 min. at room temperature. To the resulting mixture was added a solution of N$^\alpha$-hexadecanoyl-Glu(ONSu)-OBu$^t$, prepared as described in Example 35, (1.8 mg, 3.3 μmol) in acetonitrile (44.2 μl), and the reaction mixture was gently shaken for 1 h and 20 min. at room temperature. The reaction was quenched by the addition of a solution of glycine (1.8 mg, 24.2 μmol) in 50% aqueous ethanol (181 μl). A 0.5% aqueous solution of ammonium-acetate (12 ml) and NMP (300 μl) were added, and the resulting mixture eluted onto a Varian 1 g C8 Mega Bond Elut® cartridge, the immobilised compound washed with 5% aqueous acetonitrile (10 ml), and finally liberated from the cartridge by elution with TFA (6 ml). The eluate was allowed to stand for 2 h at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.23 mg, 6%) was isolated, and the product was analysed by PDMS. The m/z value for the protonated molecular ion was found to be 3752±3. The resulting molecular weight is thus 3751±3 amu (theoretical value 3751 amu).

Example 63

Synthesis of Arg$^{26,34}$Lys$^{38}$(N$^\epsilon$-(γ-glutamyl(N$^\alpha$-tetradecanoyl)))-GLP-1(7-38)-OH A mixture of Arg$^{26,34}$Lys$^{38}$-GLP-1(7-38)-OH (14 mg, 4.0 μmol), EDPA (14.3 mg, 110.6 μmol), NMP (980 μl) and water (980 μl) was gently shaken for 5 min. at room temperature. To the resulting mixture was added a solution of N$^\alpha$-tetradecanoyl-Glu(ONSu)-OBu$^t$, prepared as described in Example 29, (12.1 mg, 23.7 μmol) in NMP (303 μl), and the reaction mixture was gently shaken for 2 h at room temperature. The reaction was quenched by the addition of a solution of glycine (6.5 mg, 86.9 mmol) in 50% aqueous ethanol (652 μl). A 0.5% aqueous solution of ammonium-acetate (50 ml) was added, and the resulting mixture eluted onto a Varian 1 g C8 Mega Bond Elut® cartridge, the immobilised compound washed with 5% aqueous acetonitrile (15 ml), and finally liberated from the cartridge by elution with TFA (6 ml). The eluate was allowed to stand for 1 h and 45 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (3.9 mg, 26%) was isolated, and the product was analysed by PDMS. The m/z value for the protonated molecular ion was found to be 3881±3. The resulting molecular weight is thus 3880±3 amu (theoretical value 3880 amu).

Example 64

Synthesis of Arg$^{26,34}$Lys$^{38}$ (N$^\epsilon$-(ω-carboxypentadecanoyl))-GLP-1(7-38)-OH A mixture of Arg$^{26,34}$Lys$^{38}$-GLP-1(7-38)-OH (14 mg, 4.0 μmol), EDPA (14.3 mg, 111 μmol), NMP (980 μl) and water (980 μl) was gently shaken for 5 min. at room temperature. To the resulting mixture was added a solution of HOOC-(CH$_2$)$_{14}$-COONSu (4.5 mg, 11.9 μmol) in NMP (114 μl), the reaction mixture was gently shaken for 1 h and 45 min. at room temperature. An additional solution of HOOC-(CH$_2$)$_{14}$-COONSu (4.0 mg, 10.4 μmol) in NMP (100 μl) was added, and the resulting mixture was gently shaken for an additional 1 h and 30 min. at room temperature. The reaction was quenched by the addition of a solution of glycine (1.5 mg, 19.8 μmol) in 50% aqueous ethanol (148 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (3.9 mg, 26%) was isolated, and the product was analysed by PDMS. The m/z value for the protonated molecular ion was found to be 3809±3. The resulting molecular weight is thus 3808±3 amu (theoretical value 3808 amu).

Example 65

Synthesis of Arg$^{26,34}$Lys$^{38}$(N$^\epsilon$-(γ-glutamyl(N$^\alpha$-hexadecanoyl)))-GLP-1(7-38)-OH A mixture of Arg$^{26,34}$Lys$^{38}$-GLP-1(7-38)-OH (14 mg, 4.0 μmol), EDPA (14.3 mg, 110.6 μmol), NMP (980 μl) and water (980 μl) was gently shaken for 5 min. at room temperature. To the resulting mixture was added a solution of $N^\alpha$-hexadecanoyl-Glu(ONSu)-OBu$^t$, prepared as described in Example 35, (6.4 mg, 11.9 μmol) in NMP (160 μl), and the reaction mixture was gently shaken for 1 h and 20 min. at room temperature. The reaction was quenched by the addition of a solution of glycine (6.5 mg, 87 mmol) in 50% aqueous ethanol (653 μl). A 0.5% aqueous solution of ammonium-acetate (50 ml) was added, and the resulting mixture eluted onto a Varian 1 g C8 Mega Bond Elut® cartridge, the immobilised compound washed with 5% aqueous acetonitrile (10 ml), and finally liberated from the cartridge by elution with TFA (6 ml). The eluate was allowed to stand for 1 h and 30 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (7.2 mg, 47%) was isolated, and the product was analysed by PDMS. The m/z value for the protonated molecular ion was found to be 3881±3. The resulting molecular weight is thus 3880±3 amu (theoretical value 3880 amu).

Example 66

Synthesis of $Arg^{18,23,26,30,34}Lys^{38}(N^\epsilon$-hexadecanoyl)-GLP-1(7-38)-OH A mixture of $Arg^{18,23,26,30,34}Lys^{38}$-GLP-1(7-38)-OH (1.0 mg, 0.27 μmol), EDPA (0.34 mg, 2.7 μmol) and DMSO (600 μl) was gently shaken for 5 min. at room temperature. To the resulting mixture was added a solution of Pal-ONSu (0.28 mg, 0.8 μmol) in NMP (7 μl). The reaction mixture was gently shaken for 5 min. at room temperature, and then allowed to stand for an additional 6 h at room temperature. The reaction was quenched by the addition of a solution of glycine (1.6 mg, 21.7 μmol) in 50% aqueous ethanol (163 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (0.17 mg, 16%) was isolated, and the product was analysed by MALDI-MS. The m/z value for the protonated molecular ion was found to be 3961±3. The resulting molecular weight is thus 3960±3 amu (theoretical value 3960 amu).

Example 67

Synthesis of $Arg^{26,34}Lys^{38}(N^\epsilon$-(ω-carboxytridecanoyl))-GLP-1(7-38)-OH A mixture of $Arg^{26,34}Lys^{38}$-GLP-1(7-38)-OH (14 mg, 4.0 μmol), EDPA (14.3 mg, 111 μmol), NMP (980 μl) and water (980 μl) was gently shaken for 5 min. at room temperature. To the resulting mixture was added a solution of HOOC-$(CH_2)_{12}$-COONSu (4.2 mg, 11.9 μmol) in NMP (105 μl), the reaction mixture was gently shaken for 1 h and 50 min. at room temperature. The reaction was quenched by the addition of a solution of glycine (6.5 mg, 87 μmol) in 50% aqueous ethanol (652 μl). The reaction mixture was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (5.8 mg, 39%) was isolated, and the product was analysed by MALDI-MS. The m/z value for the protonated molecular ion was found to be 3780±3. The resulting molecular weight is thus 3779±3 amu (theoretical value 3781 amu).

Example 68

Synthesis of $Arg^{34}Lys^{26}(N^\epsilon$-(γ-glutamyl($N^\alpha$-tetradecanoyl)))-GLP-1(7-37)-OH A mixture of $Arg^{34}$-GLP-1(7-37)-OH (15 mg, 4.4 μmol), EDPA (16 mg, 124 μmol), NMP (2 ml) and water (4.8 ml) was gently shaken for 5 min. at room temperature. To the resulting mixture was added a solution of $N^\alpha$-tetradecanoyl-Glu(ONSu)-OBu$^t$, prepared as described in Example 29, (12.1 mg, 23.7 μmol) in NMP (303 μl), and the reaction mixture was gently shaken for 2 h at room temperature. The reaction was quenched by the addition of a solution of glycine (6.5 mg, 86.9 μmol) in 50% aqueous ethanol (652 μl). A 0.5% aqueous solution of ammonium-acetate (50 ml) was added, and the resulting mixture eluted onto a Varian 1 g C8 Mega Bond Elute cartridge, the immobilised compound washed with 5% aqueous acetonitrile (15 ml), and finally liberated from the cartridge by elution with TFA (6 ml). The eluate was allowed to stand for 1 h and 45 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (3.9 mg, 26%) was isolated, and the product was analysed by MALDI-MS. The m/z value for the protonated molecular ion was found to be 3723±3. The resulting molecular weight is thus 3722±3 amu (theoretical value 3723 amu).

Example 69

Synthesis of $N^\alpha$-octadecanoyl-Glu(ONSu)-OBu$^t$

To a suspension of H-Glu(OH)-OBu$^t$(2.82 g, 13.9 mmol), DMF (370 ml) and EDPA (1.79 g, 13.9 mmol) was added drop by drop a solution of Ste-ONSu (5.3 g, 13.9 mmol) in DMF (60 ml). Dichloromethane (35 ml) was added, and the reaction mixture was stirred for 24 h at room temperature and then concentrated in vacuo. The residue was partitioned between 10% aqueous citric acid (330 ml) and ethyl acetate (200 ml), and the phases were separated. The organic phase was concentrated in vacuo and the residue dissolved in DMF (60 ml). The resulting solution was added drop by drop to a 10% aqueous solution of citric acid (400 ml) kept at 0° C. The precipitated compound was collected and washed with iced water and dried in a vacuum drying oven. The dried compound was dissolved in DMF (40 ml) and HONSu (1.63 g, 14.2 mmol) was added. To the resulting mixture was added a solution of DCC (2.66 g, 12.9 mmol) in dichloromethane (51 ml). The reaction mixture was stirred for 64 h at room temperature, and the precipitated compound was filtered off. The precipitate was recrystallised from n-heptane/2-propanol to give the title compound (4.96 g, 68%).

Example 70

Synthesis of $Arg^{26,34}Lys^{38}(N^\epsilon$-(γ-glutamyl($N^\alpha$-octadecanoyl)))-GLP-1(7-38)-OH A mixture of $Arg^{26,34}$-GLP-1(7-38)-OH (28 mg, 7.9 μmol), EDPA (28.6 mg, 221.5 μmol), NMP (1.96 ml) and water (1.96 ml) was gently shaken for 5 min. at room temperature. To the resulting mixture was added a solution of N$^\alpha$-octadecanoyl-Glu(ONSu)-OBu$^t$ (17.93 g, 31.6 µmol), prepared as described in Example 44, in NMP (448 µl), and the reaction mixture was gently shaken for 2 h at room temperature. The reaction was quenched by the addition of a solution of glycine (13.1 mg, 174 µmol) in 50% aqueous ethanol (1.3 ml). A 0.5% aqueous solution of ammonium-acetate (120 ml) was added, and the resulting mixture was divided into two equal portions. Each portion was eluted onto a Varian 5 g C8 Mega Bond Elut® cartridge, the immobilised compound washed with 5% aqueous acetonitrile (25 ml), and finally liberated from the cartridge by elution TFA (25 ml). The combined eluates were allowed to stand for 1 h and 25 min. at room temperature and then concentrated in vacuo. The residue was purified by column chromatography using a cyanopropyl column (Zorbax 300SB-CN) and a standard acetonitrile/TFA system. The column was heated to 65° C. and the acetonitrile gradient was 0–100% in 60 minutes. The title compound (3.6 mg, 11%) was isolated, and the product was analysed by MALDI-MS. The m/z value for the protonated molecular ion was found to be 3940±3. The resulting molecular weight is thus 3939±3 amu (theoretical value 3937 amu).

REFERENCES

1. Pederson R A. Gastric Inhibitory Polypeptide. In Walsh J H, Dockray G J (eds) Gut peptides: Biochemistry and Physiology. Raven Press, New York 1994, pp. 217–259.
2. Krarup T. Immunoreactive gastric inhibitory polypeptide. Endocr Rev 1988;9:122–134.
3. Ørskov C. Glucagon-like peptide-1, a new hormone of the enteroinsular axis. Diabetologia 1992; 35:701–711.
4. Bell G I, Sanchez-Pescador R, Layboum P J, Najarian R C. Exon duplication and divergence in the human pre-proglucagon gene. Nature 1983; 304: 368–371.
5. Hoist J J. Glucagon-like peptide-1 (GLP-1)—a newly discovered GI hormone. Gastroenterology 1994; 107: 1848–1855.
6. Hoist J J. Gut glucagon, enteroglucagon, gut GLI, glicentin—current status. Gastroenterology 1983;84:1602–1613.
7. Hoist J J, Ørskov C. Glucagon and other proglucagon-derived peptides. In Walsh J H, Dockray G J, eds. Gut peptides: Biochemistry and Physiology. Raven Press, New York, pp. 305–340, 1993.
8. Ørskov C, Hoist J J, Knuhtsen S, Baldissera F G A, Poulsen S S, Nielsen O V. Glucagon-like peptides GLP-1 and GLP-2, predicted products of the glucagon gene, are secreted separately from the pig small intestine, but not pancreas. Endocrinology 1986;119:1467–1475.
9. Hoist J J, Bersani M, Johnsen A H, Kofod H, Hartmann B, Ørskov C. Proglucagon processing in porcine and human pancreas. J Biol Chem, 1994; 269: 18827–1883.
10. Moody A J, Hoist J J, Thim L, Jensen S L. Relationship of glicentin to proglucagon and glucagon in the porcine pancreas. Nature 1981; 289: 514–516.
11. Thim L, Moody A J, Purification and chemical characterisation of a glicentin-related pancreatic peptide (proglucagon fragment) from porcine pancreas. Biochim Biophys Acta 1982;703:134–141.
12. Thim L, Moody A J. The primary structure of glicentin (proglucagon). Regul Pept 1981;2:139–151.
13. Ørskov C, Bersani M, Johnsen AH, Højrup P, Hoist J J. Complete sequences of glucagon-like peptide-1 (GLP-1) from human and pig small intestine. J. Biol. Chem. 1989;264: 12826–12829.
14. Ørskov C, Rabenhøj L, Kofod H, Wettergren A, Hoist J J. Production and secretion of amidated and glycine-extended glucagon-like peptide-1 (GLP-1) in man. Diabetes 1991; 43: 535–539.
15. Buhl T, Thim L, Kofod H, Ørskov C, Harling H, & Hoist J J: Naturally occurring products of proglucagon 111–160 in the porcine and human small intestine. J. Biol. Chem. 1988;263:8621–8624.
16. Ørskov C, Buhl T, Rabenhøj L, Kofod H, Holst J J: Carboxypeptidase-B-like processing of the C-terminus of glucagon-like peptide-2 in pig and human small intestine. FEBS letters, 1989;247:193–106.
17. Holst J J. Evidence that enteroglucagon (II) is identical with the C-terminal sequence (residues 33–69) of glicentin. Biochem J. 1980;187:337–343.
18. Bataille D, Tatemoto K, Gespach C, Jörnvall H, Rosselin G, Mutt V. Isolation of glucagon-37 (bioactive enteroglucagon/oxyntomodulin) from porcine jejuno-ileum. Characterisation of the peptide. FEBS Lett 1982;146:79–86.
19. Ørskov C, Wettergren A, Holst J J. The metabolic rate and the biological effects of GLP-1 7-36amide and GLP-1 7-37 in healthy volunteers are identical. Diabetes 1993; 42:658–661.
20. Elliott R M, Morgan L M, Tredger J A, Deacon S, Wright J, Marks V. Glucagon-like peptide-1 (7-36)amide and glucose-dependent insulinotropic polypeptide secretion in response to nutrient ingestion in man: acute post-prandial and 24-h secretion patterns. J Endocrinol 1993; 138: 159–166.
21. Kolligs F, Fehmann H C, Göke R, Göke B. Reduction of the incretin effect in rats by the glucagon-like peptide-1 receptor antagonist exendin (9-39)amide. Diabetes 1995; 44: 16–19.
22. Wang Z, Wang R M, Owji A A, Smith D M, Ghatei M, Bloom S R. Glucagon-like peptide-1 is a physiological incretin in rat. J. Clin. Invest. 1995; 95: 417–421.
23. Thorens B. Expression cloning of the pancreatic b cell receptor for the gluco-incretin hormone glucagon-like peptide 1. Proc Natl Acad Sci 1992;89:8641–4645.
24. Scrocchi L, Auerbach A B, Joyner A L, Drucker D J. Diabetes in mice with targeted disruption of the GLP-1 receptor gene. Diabetes 1996; 45: 21A.
25. Fehmann H C, Göke R, Göke B. Cell and molecular biology of the incretin hormones glucagon-like peptide-I (GLP-1) and glucose-dependent insulin releasing polypeptide (GIP). Endocrine Reviews, 1995; 16: 390–410.
26. Gromada J, Dissing S, Bokvist K, Renstrom E, Frøkjaer-Jensen J, Wulff B S, Rorsman P. Glucagon-like peptide I increases cytoplasmic calcium in insulin-secreting bTC3-cells by enhancement of intracellular calcium mobilisation. Diabetes 1995; 44: 767–774.
27. Holz G G, Leech C A, Habener J F. Activation of a cAMP-regulated $Ca^{2+}$-signaling pathway in pancreatic β-cells by the insulinotropic hormone glucagon-like peptide-1. J Biol Chem, 1996; 270:17749–17759.
28. Holz G G, Kühitreiber W M, Habener J F. Pancreatic beta-cells are rendered glucose competent by the insulinotropic hormone glucagon-like peptide-1(7-37). Nature 1993;361:362–365.
29. Ørskov C, Hoist J J, Nielsen O V: Effect of truncated glucagon-like peptide-1 (proglucagon 78–107 amide) on endocrine secretion from pig pancreas, antrum and stomach. Endocrinology 1988;123:2009–2013.
30. Hvidberg A, Toft Nielsen M, Hilsted J, Ørskov C, Hoist J J. Effect of glucagon-like peptide-1 (proglucagon 78–107amide) on hepatic glucose production in healthy man. Metabolism 1994;43:104–108.
31. Qualmann C, Nauck M, Hoist J J, Ørskov C, Creutzfeldt W. Insulinotropic actions of intravenous glucagon-like peptide-1 [7-36 amide] in the fasting state in healthy subjects. Acta Diabetologica, 1995; 32: 13–16.
32. Nauck M A, Heimesaat M M, Ørskov C, Hoist J J, Ebert R, Creutzfeldt W. Preserved incretin activity of GLP-1(7-36amide) but not of synthetic human GIP in patients with type 2-diabetes mellitus. J Clin Invest 1993;91:301–307.
33. Nauck M A, Kleine N, Ørskov C, Hoist J J, Wilims B, Creutzfeldt W. Normalisation of fasting hyperglycaemia by exogenous GLP-1(7-36amide) in type 2-diabetic patients. Diabetologia 1993;36:741–744.
34. Creutzfeldt W, Kleine N, Willms B, Ørskov C, Hoist J J, Nauck M A. Glucagonostatic actions and reduction of fasting hyperglycaemia by exogenous glucagon-liem, peptide-1 (7-36 amide) in type I diabetic patients. Diabetes Care 1996; 19: 580–586.
35. Schjoldager B T G, Mortensen P E, Christiansen J, Ørskov C, Hoist J J. GLP-1 (glucagon-like peptide-1) and truncated GLP-1, fragments of human proglucagon, inhibit gastric acid secretion in man. Dig. Dis. Sci. 1989; 35:703–708.
36. Wettergren A, Schjoldager B, Mortensen P E, Myhre J, Christiansen J, Holst J J. Truncated GLP-1 (proglucagon 72-107 amide) inhibits gastric and pancreatic functions in man. Dig Dis Sci 1993;38:665–673.
37. Layer P, Hoist J J, Grandt D, Goebell H: heal release of glucagon-like peptide-1 (GLP-1): association with inhibition of gastric acid in humans. Dig Dis Sci 1995; 40: 1074–1082.
38. Layer P, Holst J J. GLP-1: A humoral mediator of the ileal brake in humans? Digestion 1993; 54: 385–386.
39. Nauck M, Ettler R, Niedereichholz U, Ørskov C, Hoist J J, Schmiegel W. Inhibition of gastric emptying by GLP-1(7-36 amide) or (7-37): effects on postprandial glycaemia and insulin secretion. Abstract. Gut 1995; 37 (suppl. 2): A124.
40. Schick R R, vorm Walde T, Zimmermann J P, Schusdziarra V, Classen M. Glucagon-like peptide 1—a novel brain peptide involved in feeding regulation. in Ditschuneit H, Gries F A, Hauner H, Schusdziarra V, Wechsler J G (eds.) Obesity in Europe. John Libbey & Company ltd, 1994; pp. 363-367.
41. Tang-Christensen M, Larsen P J, Göke R, Fink-Jensen A, Jessop D S, Møller M, Sheikh S. Brain GLP-1(7-36) amide receptors play a major role in regulation of food and water intake. Am. J. Physiol., 1996, in press.
42. Turton M D, O'Shea D, Gunn I, Beak S A, Edwards C M B, Meeran K, et al. A role for glucagon-like peptide-1 in the regulation of feeding. Nature 1996; 379: 69–72.
43. Willms B, Werner J, Creutzfeldt W, Ørskov C, Holst J J, Nauck M. Inhibition of gastric emptying by glucagon-like peptide-1 (7-36 amide) in patients with type-2-diabetes mellitus. Diabetologia 1994; 37, suppl. 1: A118.
44. Larsen J, Jallad N, Damsbo P. One-week continuous infusion of GLP-1(7-37) improves glycaemic control in NIDDM. Diabetes 1996; 45, suppl. 2: 233A.
45. Ritzel R, Ørskov C, Hoist J J, Nauck M A. Pharmacokinetic, insulinotropic, and glucagonostatic properties of GLP-1 [7-36 amide] after subcutaneous injection in healthy volunteers. Dose-response relationships. Diabetologia 1995; 38: 720–725.
46. Deacon C F, Johnsen A H, Hoist J J. Degradation of glucagon-like peptide-1 by human plasma in vitro yields an N-terminally truncated peptide that is a major endogenous metabolite in vivo. J Clin Endocrinol Metab 1995; 80: 952–957.
47. Deacon C F, Nauck M A, Toft-Nielsen M, Pridal L, Willms B, Hoist J J. 1995. Both subcutaneous and intravenously administered glucagon-like peptide-1 are rapidly degraded from the amino terminus in type II diabetic patients and in healthy subjects. Diabetes 44: 1126–1131.

What is claimed is:

1. A pharmaceutical composition comprising a glucagon like peptide-1 (GLP-1) derivative and a dual Peroxisome Proliferator-Activated Receptor-α/Peroxisome Proliferator Activated Receptor-γ (PPARα/PPAR-γ) activator wherein the dual PPAR-α/PPAR-γ activator is a compound of formula (I)

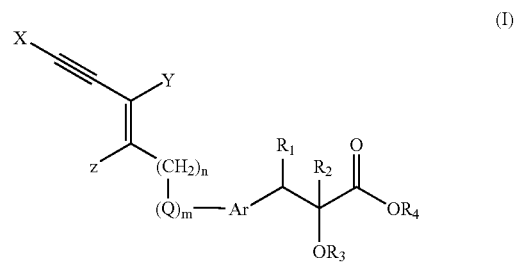

wherein X is hydrogen or
X is $C_{1-2}$-alkyl, $C_{2-12}$-alkenyl, $C_{2-12}$-alkynyl, aryl, heteroaryl, aralkyl, heteroaralkyl or heterocyclyl each of which is optionally substituted with one or more substituents selected from halogen, perhalomethyl, hydroxy, $C_{1-6}$-alkyl, $C_{2-6}$-alkenyl, $C_{2-6}$-alkynyl, hydroxy, $C_{1-6}$-alkoxy, $C_{1-6}$-alkylthio, aryl, aryloxy, arylthio, acyl, aralkyl, aralkoxy, heteroaryl, heteroaralkyl, heteroaryloxy, heteroaralkoxy, $C_{1-6}$-alkylthio, cyano, amino, $C_{1-6}$-alkylamino, $C_{1-6}$-dialkylamino, carboxy or $C_{1-6}$-alkylester; and
Y is hydrogen or
Y is $C_{1-12}$-alkyl, $C_{2-12}$-alkenyl, $C_{2-12}$-alkynyl, $C_{4-12}$-alkenynyl, aryl, heteroaryl, aralkyl or heteroaralkyl each of which is optionally substituted with one or more substituents selected from halogen, $C_{1-6}$alkyl, perhalomethyl, hydroxy, aryl, heteroaryl, amino, carboxy or $C_{1-6}$alkylester; and
Z is hydrogen, halogen, hydroxy or
Z is $C_{1-6}$alkyl or $C_{1-6}$alkoxy each of which is optionally substituted with one or more substituents selected from $C_{1-6}$-alkoxy, halogen, hydroxy, carboxy, amino or cyano; and
Q is O, S or $NR_5$, wherein $R_5$ is hydrogen, $C_{1-6}$alkyl, $C_{2-6}$-alkenyl, $C_{2-6}$-alkynyl, $C_{4-6}$-alkenynyl, aralkyl or heteroaralkyl and wherein $R_5$ is optionally substituted with one or more substituents selected from halogen, hydroxy, $C_{1-6}$-alkoxy, amino or carboxy; and
Ar is arylene, heteroarylene or a divalent heterocyclic group each of which can be optionally substituted with one or more substituents selected from $C_{1-6}$alkyl, aryl or $C_{1-6}$-alkoxy each of which can be optionally substituted with halogen, hydroxy, carboxy or $C_{1-6}$-alkylester; and $R_1$ is hydrogen, hydroxy or halogen; or $R_1$ forms a bond together with $R_2$; and $R_2$ is hydrogen or $C_{1-6}$-alkyl; or $R_2$ forms a bond together with $R_1$; and $R_3$ is hydrogen, $C_{1-6}$-alkyl, $C_{2-6}$-alkenyl, $C_{2-6}$-alkynyl, $C_{4-6}$-alkenynyl, aryl, aralkyl, $C_{1-6}$-alkoxy$C_{1-6}$-alkyl, acyl, heterocyclyl, heteroaryl or heteroaralkyl groups optionally substituted with one or more substituents selected from halogen, perhalomethyl, hydroxy, cyano, carboxy or $C_{1-6}$-alkylester; and $R_4$ is hydrogen, $C_{1-6}$alkyl, $C_{2-6}$-alkenyl, $C_{2-6}$-alkynyl, $C_{4-6}$-alkenynyl or aryl;

n is an integer ranging from 0 to 3; and m is an integer ranging from 0 to 1;

or a pharmaceutically acceptable salt thereof, or a pharmaceutically acceptable solvate thereof, or any tautomeric forms, stereoisomers, mixture of stereoisomers, racemic mixture, or polymorphs.

2. The pharmaceutical composition according to claim 1 wherein X is aryl, heteroaryl or heterocyclyl optionally substituted with one or more substituents selected from halogen, perhalomethyl, $C_{1-6}$-alkoxy, $C_{1-6}$alkylthio, aryl, aryloxy, arylthio, aralkyl, aralkoxy, heteroaryl, heteroaralkyl, heteroaryloxy or heteroaralkoxy.

3. The pharmaceutical composition according to claim 1 wherein X is aryl, heteroaryl or heterocyclyl each of which is optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

4. The pharmaceutical composition according to claim 1 wherein X is aryl optionally substituted with one or more substituents selected from halogen, perhalomethyl, $C_{1-6}$-alkoxy, $C_{1-6}$alkylthio, aryl, aryloxy, arylthio, aralkyl, aralkoxy, heteroaryl, heteroaralkyl, heteroaryloxy or heteroaralkoxy.

5. The pharmaceutical composition according to claim 1 wherein X is phenyl or naphthyl each of which is optionally substituted with one or more substituents selected from halogen or perhalomethyl.

6. The pharmaceutical composition according to claim 1 wherein X is phenyl optionally substituted with one or more substituents selected from halogen.

7. The pharmaceutical composition according to claim 1 wherein X is phenyl.

8. The pharmaceutical composition according to claim 1 wherein X is heteroaryl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

9. The pharmaceutical composition according to claim 1 wherein X is heterocyclyl optionally substituted with one or more substituents selected from halogen, perhalomethyl, $C_{1-6}$-alkoxy, $C_{1-6}$-alkylthio, aryl, aryloxy, arylthio, aralkyl, aralkoxy, heteroaryl, heteroaralkyl, heteroaryloxy or heteroaralkoxy.

10. The pharmaceutical composition according to claim 1 wherein Y is hydrogen, $C_{1-12}$-alkyl or aryl.

11. The pharmaceutical composition according to claim 1 wherein Y is hydrogen or methyl.

12. The pharmaceutical composition according to claim 1 wherein Y is hydrogen.

13. The pharmaceutical composition according to claim 1 wherein Z is hydrogen or $C_{1-6}$-alkoxy.

14. The pharmaceutical composition according to claim 1 wherein Z is hydrogen.

15. The pharmaceutical composition according to claim 1 wherein Q is O.

16. The pharmaceutical composition according to claim 1 wherein Ar is arylene optionally substituted with one or more substituents selected from $C_{1-6}$-alkyl or $C_{1-6}$-alkoxy each of which can be optionally substituted with carboxy.

17. The pharmaceutical composition according to claim 1 wherein Ar is phenylene.

18. The pharmaceutical composition according to claim 1 wherein $R_1$ is hydrogen or $R_1$ forms a bond together with $R_2$.

19. The pharmaceutical composition according to claim 1 wherein $R_1$ is hydrogen.

20. The pharmaceutical composition according to claim 1 wherein $R_2$ is hydrogen or $R_2$ forms a bond together with $R_1$.

21. The pharmaceutical composition according to claim 1 wherein $R_2$ is hydrogen.

22. The pharmaceutical composition according to claim 1 wherein $R_3$ is $C_{1-6}$-alkyl.

23. The pharmaceutical composition according to claim 1 wherein $R_3$ is $C_{1-2}$-alkyl.

24. The pharmaceutical composition according to claim 1 wherein $R_4$ is hydrogen.

25. The pharmaceutical composition according to claim 1 wherein n is 1.

26. The pharmaceutical composition according to claim 1 wherein m is 1.

27. The pharmaceutical composition according to claim 1 wherein alkyl is methyl or ethyl.

28. The pharmaceutical composition according to claim 1 wherein alkenyl is vinyl or 1-propenyl.

29. The pharmaceutical composition according to claim 1 wherein alkynyl is 1-propynyl.

30. The pharmaceutical composition according to claim 1 wherein alkenynyl is 1-pentene-4-yne.

31. The pharmaceutical composition according to claim 1 wherein alkoxy is methoxy, ethoxy, isopropoxy or cyclopropoxy.

32. The pharmaceutical composition according to claim 1 wherein aryl is phenyl or naphthyl optionally substituted with halogen.

33. The pharmaceutical composition according to claim 1 wherein arylene is phenylene.

34. The pharmaceutical composition according to claim 1 wherein halogen is chlorine.

35. The pharmaceutical composition according to claim 1 wherein perhalomethyl is trifluoromethyl.

36. The pharmaceutical composition according to claim 1 wherein heteroaryl is furan, pyrrole, pyridine, indole or benzofuran.

37. The pharmaceutical composition according to claim 1 wherein heteroarylene is furan, pyrrole, pyridine, indole or benzofuran.

38. The pharmaceutical composition according to claim 1 wherein aralkyl is benzyl.

39. The pharmaceutical composition according to claim 1 wherein aryloxy is phenoxy.

40. The pharmaceutical composition according to claim 1 wherein aralkoxy is benzyloxy.

41. The pharmaceutical composition according to claim 1 wherein n is an integer ranging from 1 to 3 and m is 1.

42. The pharmaceutical composition according to claim 1 wherein the substituents Z and Y are arranged in a trans-configuration.

43. The pharmaceutical composition according to claim 1 wherein the substituents Z and Y are arranged in a cis-configuration.

44. The pharmaceutical composition according to claim 1 wherein the dual PPAR-α/PPAR-γ activator of formula (I) is selected from the following:
(E)-(S)-2-Ethoxy-3-[4-(5-phenyl-pent-2-en-4-ynyloxy)-phenyl]-propionic acid ethyl ester,
(E)-(S)-2-Ethoxy-3-[4-(5-phenyl-pent-2-en-4-ynyloxy)-phenyl]-propionic acid,
(Z)-(S)-2-Ethoxy-3-[4-(3-methyl-5-phenyl-pent-2-en-4-ynyloxy)-phenyl]-propionic acid ethyl ester,
(Z)-(S)-2-Ethoxy-3-[4-(3-methyl-5-phenyl-pent-2-en-4-ynyloxy)-phenyl]-propionic acid,
(E)-(S)-2-Ethoxy-3-[4-(3-methyl-5-phenyl-pent-2-en-4-ynyloxy)-phenyl]-propionic acid ethyl ester, and
(E)-(S)-2-ethoxy-3-[4-(3-methyl-5-phenyl-pent-2-en-4-ynyloxy)-phenyl]-propionic acid;
or a pharmaceutically acceptable salt thereof.

45. The pharmaceutical composition according to claim 1 wherein the dual PPAR-α/PPAR-γ activator of formula (I) is selected from the following:
Ethyl (E)-(S)-2-ethoxy-3-[4-(3-methyl-5-(3,5-dichloro-phenyl)-pent-2-en-4-ynyloxy)-phenyl]-propionate,
(E)-(S)-2-ethoxy-3-[4-(3-methyl-5-(3,5-dichloro-phenyl)-pent-2-en-4-ynyloxy)-phenyl]-propionic acid,
Ethyl (Z)-(S)-2-ethoxy-3-[4-(3-methyl-5-(3,5-dichloro-phenyl)-pent-2-en-4-ynyloxy)-phenyl]-propionate,
(Z)-(S)-2-ethoxy-3-[4-(3-methyl-5-(3,5-dichloro-phenyl)-pent-2-en-4-ynyloxy)-phenyl]-propionic acid,
Ethyl (E)-(S)-2-ethoxy-3-[4-(3-methyl-5-(3-trifluoromethyl-phenyl)-pent-2-en-4-ynyloxy)-phenyl]-propionate,
(E)-(S)-2-ethoxy-3-[4-(3-methyl-5-(3-trifluoromethyl-phenyl)-pent-2-en-4-ynyloxy)-phenyl]-propionic acid,
Ethyl (Z)-(S)-2-ethoxy-3-[4-(3-methyl-5-(3-trifluoromethyl-phenyl)-pent-2-en-4-ynyloxy)-phenyl]-propionate, and
(Z)-(S)-2-ethoxy-3-[4-(3-methyl-5-(3-trifluoromethyl-phenyl)-pent-2-en-4-ynyloxy)-phenyl]-propionic acid;
or a pharmaceutically acceptable salt thereof.

46. The pharmaceutical composition according to claim 1 wherein the dual PPAR-α/PPAR-γ activator of formula (I) is selected from the following:
Ethyl (E)-(S)-2-ethoxy-3-[4-(3-methyl-5-(1-naphthyl)-pent-2-en-4-ynyloxy)-phenyl]-propionate,
(E)-(S)-2-ethoxy-3-[4-(3-methyl-5-(1-naphthyl)-pent-2-en-4-ynyloxy)-phenyl]-propionic acid,
Ethyl (Z)-(S)-2-ethoxy-3-[4-(3-methyl-5-(1-naphthyl)-pent-2-en-4-ynyloxy)-phenyl]-propionate,
(Z)-(S)-2-ethoxy-3-[4-(3-methyl-5-(1-naphthyl)-pent-2-en-4-ynyloxy)-phenyl]-propionic acid,
Ethyl (E)-(S)-2-ethoxy-3-[4-(-5-(3,5-dichloro-phenyl)-pent-2-en-4-ynyloxy)-phenyl]-propionate,
(E)-(S)-2-ethoxy-3-[4-(5-(3,5-dichloro-phenyl)-pent-2-en-4-ynyloxy)-phenyl]-propionic acid,
Ethyl (Z)-(S)-2-ethoxy-3-[4-(3-methyl-5-(3,5-dichloro-phenyl)-pent-2-en-4-ynyloxy)-phenyl]-propionate, and
(Z)-(S)-2-ethoxy-3-[4-(3-methyl-5-(3,5-dichloro-phenyl)-pent-2-en-4-ynyloxy)-phenyl]-propionic acid;
or a pharmaceutically acceptable salt thereof.

47. The pharmaceutical composition according to claim 1 wherein the dual PPAR-α/PPAR-γ activator of formula (I) is selected from the following:
(Z)-(S)-2-Ethoxy-3-[4-(5-phenyl-pent-2-en-4-ynyloxy)-phenyl]-propionic acid ethyl ester,
(Z)-(S)-2-Ethoxy-3-[4-(5-phenyl-pent-2-en-4-ynyloxy)-phenyl]-propionic acid, and
(E)-(RS)-2-Ethoxy-3-[3-(5-phenyl-pent-2-en-4-ynyloxy)-phenyl]-propionic acid ethyl ester;
or a pharmaceutically acceptable salt thereof.

48. The pharmaceutical composition according to claim 1 wherein the dual PPAR-α/PPAR-γ activator of formula (I) is selected from the following:
(E)-(S)-3-{4-[5-(1,3-Difluoro-phenyl)-pent-2-en-4-ynyloxy]-phenyl}-2-ethoxy-propionic acid,
(E)-(S)-3-{4-[5-(1,3-Dibromo-phenyl)-pent-2-en-4-ynyloxy]-phenyl}-2-ethoxy-propionic acid,
(E)-(S)-3-{4-[5-(1,3-Diiodo-phenyl)-pent-2-en-4-ynyloxy]-phenyl}-2-ethoxy-propionic acid,
(E)-(S)-3-{4-[5-(1,3-Bis-trifluoromethyl-phenyl)-pent-2-en-4-ynyloxy]-phenyl}-2-ethoxy-propionic acid,
(E)-(S)-3-{4-[5-(1,3-Dimethoxy-phenyl)-pent-2-en-4-ynyloxy]-phenyl}-2-ethoxy-propionic acid,
(E)-(S)-3-{4-[5-(1,3-Diethoxy-phenyl)-pent-2-en-4-ynyloxy]-phenyl}-2-ethoxy-propionic acid,
(E)-(S)-3-{4-[5-(1,3-Bis-(2,2,2-trifluoromethoxy)-phenyl)-pent-2-en-4-ynyloxy]-phenyl}-2-ethoxy-propionic acid,
(E)-(S)-3-{4-[5-(1,3-Bis-(2,2,2-trifluoroethoxy)-phenyl)-pent-2-en-4-ynyloxy]-phenyl}-2-ethoxy-propionic acid,
(E)-(S)-3-{4-[5-(3,5-Difluoro-phenyl)-pent-2-en-4-ynyloxy]-phenyl}-2-ethoxy-propionic acid,
(E)-(S)-3-{4-[5-(3,5-Dibromo-phenyl)-pent-2-en-4-ynyloxy]-phenyl}-2-ethoxy-propionic acid,
(E)-(S)-3-{4-[5-(3,5-Diiodo-phenyl)-pent-2-en-4-ynyloxy]-phenyl}-2-ethoxy-propionic acid,
(E)-(S)-3-{4-[5-(3,5-Bis-trifluoromethyl-phenyl)-pent-2-en-4-ynyloxy]-phenyl}-2-ethoxy-propionic acid,
(E)-(S)-3-{4-[5-(3,5-Dimethoxy-phenyl)-pent-2-en-4-ynyloxy]-phenyl}-2-ethoxy-propionic acid,
(E)-(S)-3-{4-[5-(3,5-Diethoxy-phenyl)-pent-2-en-4-ynyloxy]-phenyl}-2-ethoxy-propionic acid,
(E)-(S)-3-{4-[5-(3,5-Bis-(2,2,2-trifluoromethoxy)-phenyl)-pent-2-en-4-ynyloxy]-phenyl}-2-ethoxy-propionic acid,
(E)-(S)-3-{4-[5-(3,5-Bis-(2,2,2-trifluoroethoxy)-phenyl)-pent-2-en-4-ynyloxy]-phenyl}-2-ethoxy-propionic acid,
(E)-(S)-3-{4-[5-(1,3-Difluoro-phenyl)-3-methyl-pent-2-en-4-ynyloxy]-phenyl}-2-ethoxy-propionic acid,
(E)-(S)-3-{4-[5-(1,3-Dibromo-phenyl)-3-methyl-pent-2-en-4-ynyloxy]-phenyl}-2-ethoxy-propionic acid,
(E)-(S)-3-{4-[5-(1,3-Diiodo-phenyl)-3-methyl-pent-2-en-4-ynyloxy]-phenyl}-2-ethoxy-propionic acid,
(E)-(S)-3-{4-[5-(1,3-Bis-trifluoromethyl-phenyl)-3-methyl-pent-2-en-4-ynyloxy]-phenyl}-2-ethoxy-propionic acid,
(E)-(S)-3-{4-[5-(1,3-Dimethoxy-phenyl)-pent-2-en-4-ynyloxy]-phenyl}-3-methyl-2-ethoxy-propionic acid,
(E)-(S)-3-{4-[5-(1,3-Diethoxy-phenyl)-3-methyl-pent-2-en-4-ynyloxy]-phenyl}-2-ethoxy-propionic acid,
(E)-(S)-3-{4-[5-(1,3-Bis-(2,2,2-trifluoromethoxy)-phenyl)-3-methyl pent-2-en-4-ynyloxy]-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-phenyl}-2-ethoxy-propionic acid,
(E)-(S)-3-{4-[5-(3,5-Difluoro-phenyl)-3-methyl-pent-2-en-4-ynyloxy]-phenyl}-2-ethoxy-propionic acid,
(E)-(S)-3-{4-[5-(3,5-Dibromo-phenyl)-3-methyl-pent-2-en-4-ynyloxy]-phenyl}-2-ethoxy-propionic acid, (E)-(S)-3-{4-[5-(3,5-Diiodo-phenyl)-3-methyl-pent-2-en-4-ynyloxy]-phenyl}-2-ethoxy-propionic acid,
(E)-(S)-3-{4-[5-(3,5-Bis-trifluoromethyl-phenyl)-3-methyl-pent-2-en-4-ynyloxy]-phenyl}-2-ethoxy-propionic acid,
(E)-(S)-3-{4-[5-(3,5-Dimethoxy-phenyl)-3-methyl-pent-2-en-4-ynyloxy]-phenyl}-2-ethoxy-propionic acid,
(E)-(S)-3-{4-[5-(3,5-Diethoxy-phenyl)-3-methyl-pent-2-en-4-ynyloxy]-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-phenyl}-2-ethoxy-propionic acid,
(E)-(S)-3-{4-[5-(1,3-Difluoro-phenyl)-pent-2-en-4-ynyloxy]-3-chloro-phenyl}-2-ethoxy-propionic acid,
(E)-(S)-3-{4-[5-(1,3-Dibromo-phenyl)-pent-2-en-4-ynyloxy]-3-chloro-phenyl}-2-ethoxy-propionic acid,
(E)-(S)-3-{4-[5-(1,3-Diiodo-phenyl)-pent-2-en-4-ynyloxy]-3-chloro-phenyl}-2-ethoxy-propionic acid,
(E)-(S)-3-{4-[5-(1,3-Bis-trifluoromethyl-phenyl)-pent-2-en-4-ynyloxy]-3-chloro-phenyl}-2-ethoxy-propionic acid,
(E)-(S)-3-{4-[5-(1,3-Dimethoxy-phenyl)-pent-2-en-4-ynyloxy]-3-chloro-phenyl}-2-ethoxy-propionic acid,
(E)-(S)-3-{4-[5-(1,3-Diethoxy-phenyl)-pent-2-en-4-ynyloxy]-3-chloro-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-chloro-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-chloro-phenyl}-2-ethoxy-propionic acid,
(E)-(S)-3-{4-[5-(3,5-Difluoro-phenyl)-pent-2-en-4-ynyloxy]-3-chloro-phenyl}-2-ethoxy-propionic acid,
(E)-(S)-3-{4-[5-(3,5-Dibromo-phenyl)-pent-2-en-4-ynyloxy]-3-chloro-phenyl}-2-ethoxy-propionic acid,
(E)-(S)-3-{4-[5-(3,5-Diiodo-phenyl)-pent-2-en-4-ynyloxy]-3-chloro-phenyl}-2-ethoxy-propionic acid,
(E)-(S)-3-{4-[5-(3,5-Bis-trifluoromethyl-phenyl)-pent-2-en-4-ynyloxy]-3-chloro-phenyl}-2-ethoxy-propionic acid,
(E)-(S)-3-{4-[5-(3,5-Dimethoxy-phenyl)-pent-2-en-4-ynyloxy]-3-chloro-phenyl}-2-ethoxy-propionic acid,
(E)-(S)-3-{4-[5-(3,5-Diethoxy-phenyl)-pent-2-en-4-ynyloxy]-3-chloro-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-chloro-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-chloro-phenyl}-2-ethoxy-propionic acid,
(E)-(S)-3-{4-[5-(1,3-Difluoro-phenyl)-3-methyl-pent-2-en-4-ynyloxy]-3-chloro-phenyl}-2-ethoxy-propionic acid,
(E)-(S)-3-{4-[5-(1,3-Dibromo-phenyl)-3-methyl-pent-2-en-4-ynyloxy]-3-chloro-phenyl}-2-ethoxy-propionic acid,
(E)-(S)-3-{4-[5-(1,3-Diiodo-phenyl)-3-methyl-pent-2-en-4-ynyloxy]-3-chloro-phenyl}-2-ethoxy-propionic acid,
(E)-(S)-3-{4-[5-(1,3-Bis-trifluoromethyl-phenyl)-3-methyl-pent-2-en-4-ynyloxy]-3-chloro-phenyl}-2-ethoxy-propionic acid,
(E)-(S)-3-{4-[5-(1,3-Dimethoxy-phenyl)-pent-2-en-4-ynyloxy]-3-chloro-phenyl}-3-methyl-2-ethoxy-propionic acid,
(E)-(S)-3-{4-[5-(1,3-Diethoxy-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{4-[5-(3,5-Difluoro-phenyl)-3-methyl-pent-2-en-4-ynyloxy]-3-chloro-phenyl}-2-ethoxy-propionic acid,
(E)-(S)-3-{4-[5-(3,5-Dibromo-phenyl)-3-methyl-pent-2-en-4-ynyloxy]-3-chloro-phenyl}-2-ethoxy-propionic acid,
(E)-(S)-3-{4-[5-(3,5-Diiodo-phenyl)-3-methyl-pent-2-en-4-ynyloxy]-3-chloro-phenyl}-2-ethoxy-propionic acid,
(E)-(S)-3-{4-[5-(3,5-Bis-trifluoromethyl-phenyl)-3-methyl-pent-2-en-4-ynyloxy]-3-chloro-phenyl}-2-ethoxy-propionic acid,
(E)-(S)-3-{4-[5-(3,5-Dimethoxy-phenyl)-3-methyl-pent-2-en-4-ynyloxy]-3-chloro-phenyl}-2-ethoxy-propionic acid,
(E)-(S)-3-{4-[5-(3,5-Diethoxy-phenyl)-3-methyl-pent-2-en-4-ynyloxy]-3-chloro-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-chloro-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid,
(E)-(S)-3-{4-[5-(1,3-Difluoro-phenyl)-pent-2-en-4-ynyloxy]-3-bromo-phenyl}-2-ethoxy-propionic acid,
(E)-(S)-3-{4-[5-(1,3-Dibromo-phenyl)-pent-2-en-4-ynyloxy]-3-bromo-phenyl}-2-ethoxy-propionic acid,
(E)-(S)-3-{4-[5-(1,3-Diiodo-phenyl)-pent-2-en-4-ynyloxy]-3-bromo-phenyl}-2-ethoxy-propionic acid,
(E)-(S)-3-{4-[5-(1,3-Bis-trifluoromethyl-phenyl)-pent-2-en-4-ynyloxy]-3-bromo-phenyl}-2-ethoxy-propionic acid,
(E)-(S)-3-{4-[5-(1,3-Dimethoxy-phenyl)-pent-2-en-4-ynyloxy]-3-bromo-phenyl}-2-ethoxy-propionic acid,
(E)-(S)-3-{4-[5-(1,3-Diethoxy-phenyl)-pent-2-en-4-ynyloxy]-3-bromo-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-bromo-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(3,5-Difluoro-phenyl)-pent-2-en-4-ynyloxy]-3-bromo-phenyl}-2-ethoxy-propionic acid,
(E)-(S)-3-{4-[5-(3,5-Dibromo-phenyl)-pent-2-en-4-ynyloxy]-3-bromo-phenyl}-2-ethoxy-propionic acid,
(E)-(S)-3-{4-[5-(3,5-Diiodo-phenyl)-pent-2-en-4-ynyloxy]-3-bromo-phenyl}-2-ethoxy-propionic acid,
(E)-(S)-3-{4-[5-(3,5-Bis-trifluoromethyl-phenyl)-pent-2-en-4-ynyloxy]-3-bromo-phenyl}-2-ethoxy-propionic acid,
(E)-(S)-3-{4-[5-(3,5-Dimethoxy-phenyl)-pent-2-en-4-ynyloxy]-3-bromo-phenyl}-2-ethoxy-propionic acid,
(E)-(S)-3-{4-[5-(3,5-Diethoxy-phenyl)-pent-2-en-4-ynyloxy]-3-bromo-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-bromo-phenyl}-2-ethoxy-propionic acid, (E)-(S)-3-{4-[5-(3,5-Bis-(2,2,2-trifluoroethoxy)-phenyl)-pent-2-en-4-ynyloxy]-3-bromo-phenyl}-2-ethoxy-propionic acid,
(E)-(S)-3-{4-[5-(1,3-Difluoro-phenyl)-3-methyl-pent-2-en-4-ynyloxy]-3-bromo-phenyl}-2-ethoxy-propionic acid,
(E)-(S)-3-{4-[5-(1,3-Dibromo-phenyl)-3-methyl-pent-2-en-4-ynyloxy]-3-bromo-phenyl}-2-ethoxy-propionic acid,
(E)-(S)-3-{4-[5-(1,3-Diiodo-phenyl)-3-methyl-pent-2-en-4-ynyloxy]-3-bromo-phenyl}-2-ethoxy-propionic acid,
(E)-(S)-3-{4-[5-(1,3-Bis-trifluoromethyl-phenyl)-3-methyl-pent-2-en-4-ynyloxy]-3-bromo-phenyl}-2-ethoxy-propionic acid,
(E)-(S)-3-{4-[5-(1,3-Dimethoxy-phenyl)-pent-2-en-4-ynyloxy]-3-bromo-phenyl}-3-methyl-2-ethoxy-propionic acid,
(E)-(S)-3-{4-[5-(1,3-Diethoxy-phenyl)-3-methyl-pent-2-en-4-ynyloxy]-3-bromo-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-bromo-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid,
(E)-(S)-3-{4-[5-(3,5-Difluoro-phenyl)-3-methyl-pent-2-en-4-ynyloxy]-3-bromo-phenyl}-2-ethoxy-propionic acid,
(E)-(S)-3-{4-[5-(3,5-Dibromo-phenyl)-3-methyl-pent-2-en-4-ynyloxy]-3-bromo-phenyl}-2-ethoxy-propionic acid,
(E)-(S)-3-{4-[5-(3,5-Diiodo-phenyl)-3-methyl-pent-2-en-4-ynyloxy]-3-bromo-phenyl}-2-ethoxy-propionic acid,
(E)-(S)-3-{4-[5-(3,5-Bis-trifluoromethyl-phenyl)-3-methyl-pent-2-en-4-ynyloxy]-3-bromo-phenyl}-2-ethoxy-propionic acid,
(E)-(S)-3-{4-[5-(3,5-Dimethoxy-phenyl)-3-methyl-pent-2-en-4-ynyloxy]-3-bromo-phenyl}-2-ethoxy-propionic acid,
(E)-(S)-3-{4-[5-(3,5-Diethoxy-phenyl)-3-methyl-pent-2-en-4-ynyloxy]-3-bromo-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-bromo-phenyl}-2-ethoxy-propionic acid,
(E)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid,
(E)-(S)-3-{4-[5-(1,3-Difluoro-phenyl)-pent-2-en-4-ynyloxy]-3-iodo-phenyl}-2-ethoxy-propionic acid,
(E)-(S)-3-{4-[5-(1,3-Dibromo-phenyl)-pent-2-en-4-ynyloxy]-3-iodo-phenyl}-2-ethoxy-propionic acid,
(E)-(S)-3-{4-[5-(1,3-Diiodo-phenyl)-pent-2-en-4-ynyloxy]-3-iodo-phenyl}-2-ethoxy-propionic acid,
(E)-(S)-3-{4-[5-(1,3-Bis-trifluoromethyl-phenyl)-pent-2-en-4-ynyloxy]-3-iodo-phenyl}-2-ethoxy-propionic acid,
(E)-(S)-3-{4-[5-(1,3-Dimethoxy-phenyl)-pent-2-en-4-ynyloxy]-3-iodo-phenyl}-2-ethoxy-propionic acid,
(E)-(S)-3-{4-[5-(1,3-Diethoxy-phenyl)-pent-2-en-4-ynyloxy]-3-iodo-phenyl}-2-ethoxy-propionic acid,
(E)-(S)-3-{4-[5-(1,3-Bis-(2,2,2-trifluoromethoxy)-phenyl)-pent-2-en-4-ynyloxy]-3-iodo-phenyl}-2-ethoxy-propionic acid,
(E)-(S)-3-{4-[5-(1,3-Bis-(2,2,2-trifluoroethoxy)-phenyl)-pent-2-en-4-ynyloxy]-3-iodo-phenyl}-2-ethoxy-propionic acid,
(E)-(S)-3-{4-[5-(3,5-Difluoro-phenyl)-pent-2-en-4-ynyloxy]-3-iodo-phenyl}-2-ethoxy-propionic acid,
(E)-(S)-3-{4-[5-(3,5-Dibromo-phenyl)-pent-2-en-4-ynyloxy]-3-iodo-phenyl}-2-ethoxy-propionic acid,
(E)-(S)-3-{4-[5-(3,5-Diiodo-phenyl)-pent-2-en-4-ynyloxy]-3-iodo-phenyl}-2-ethoxy-propionic acid,
(E)-(S)-3-{4-[5-(3,5-Bis-trifluoromethyl-phenyl)-pent-2-en-4-ynyloxy]-3-iodo-phenyl}-2-ethoxy-propionic acid,
(E)-(S)-3-{4-[5-(3,5-Dimethoxy-phenyl)-pent-2-en-4-ynyloxy]-3-iodo-phenyl}-2-ethoxy-propionic acid,
(E)-(S)-3-{4-[5-(3,5-Diethoxy-phenyl)-pent-2-en-4-ynyloxy]-3-iodo-phenyl}-2-ethoxy-propionic acid,
(E)-(S)-3-{4-[5-(3,5-Bis-(2,2,2-trifluoromethoxy)-phenyl)-pent-2-en-4-ynyloxy]-3-iodo-phenyl}-2-ethoxy-propionic acid,
(E)-(S)-3-{4-[5-(3,5-Bis-(2,2,2-trifluoroethoxy)-phenyl)-pent-2-en-4-ynyloxy]-3-iodo-phenyl}-2-ethoxy-propionic acid,
(E)-(S)-3-{4-[5-(1,3-Difluoro-phenyl)-3-methyl-pent-2-en-4-ynyloxy]-3-iodo-phenyl}-2-ethoxy-propionic acid,
(E)-(S)-3-{4-[5-(1,3-Dibromo-phenyl)-3-methyl-pent-2-en-4-ynyloxy]-3-iodo-phenyl}-2-ethoxy-propionic acid,
(E)-(S)-3-{4-[5-(1,3-Diiodo-phenyl)-3-methyl-pent-2-en-4-ynyloxy]-3-iodo-phenyl}-2-ethoxy-propionic acid,
(E)-(S)-3-{4-[5-(1,3-Bis-trifluoromethyl-phenyl)-3-methyl-pent-2-en-4-ynyloxy]-3-iodo-phenyl}-2-ethoxy-propionic acid,
(E)-(S)-3-{4-[5-(1,3-Dimethoxy-phenyl)-pent-2-en-4-ynyloxy]-3-iodo-phenyl}-3-methyl-2-ethoxy-propionic acid,
(E)-(S)-3-{4-[5-(1,3-Diethoxy-phenyl)-3-methyl-pent-2-en-4-ynyloxy]-3-iodo-phenyl}-2-ethoxy-propionic acid,
(E)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid,
(E)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid,
(E)-(S)-3-{4-[5-(3,5-Difluoro-phenyl)-3-methyl-pent-2-en-4-ynyloxy]-3-iodo-phenyl}-2-ethoxy-propionic acid,
(E)-(S)-3-{4-[5-(3,5-Dibromo-phenyl)-3-methyl-pent-2-en-4-ynyloxy]-3-iodo-phenyl}-2-ethoxy-propionic acid,
(E)-(S)-3-{4-[5-(3,5-Diiodo-phenyl)-3-methyl-pent-2-en-4-ynyloxy]-3-iodo-phenyl}-2-ethoxy-propionic acid,
(E)-(S)-3-{4-[5-(3,5-Bis-trifluoromethyl-phenyl)-3-methyl-pent-2-en-4-ynyloxy]-3-iodo-phenyl}-2-ethoxy-propionic acid,
(E)-(S)-3-{4-[5-(3,5-Dimethoxy-phenyl)-3-methyl-pent-2-en-4-ynyloxy]-3-iodo-phenyl}-2-ethoxy-propionic acid,
(E)-(S)-3-{4-[5-(3,5-Diethoxy-phenyl)-3-methyl-pent-2-en-4-ynyloxy]-3-iodo-phenyl}-2-ethoxy-propionic acid,
(E)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid, and (E)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;

or a pharmaceutically acceptable salt thereof.

49. The pharmaceutical composition according to claim 1 wherein the dual PPAR-α/PPAR-γ activator of formula (I) is selected from the following:

(Z)-(S)-3-{4-[5-(1,3-Difluoro-phenyl)-pent-2-en-4-ynyloxy]-phenyl}-2-ethoxy-propionic acid,
(Z)-(S)-3-{4-[5-(1,3-Dibromo-phenyl)-pent-2-en-4-ynyloxy]-phenyl}-2-ethoxy-propionic acid,
(Z)-(S)-3-{4-[5-(1,3-Diiodo-phenyl)-pent-2-en-4-ynyloxy]-phenyl}-2-ethoxy-propionic acid,
(Z)-(S)-3-{4-[5-(1,3-Bis-trifluoromethyl-phenyl)-pent-2-en-4-ynyloxy]-phenyl}-2-ethoxy-propionic acid,
(Z)-(S)-3-{4-[5-(1,3-Dimethoxy-phenyl)-pent-2-en-4-ynyloxy]-phenyl}-2-ethoxy-propionic acid,
(Z)-(S)-3-{4-[5-(1,3-Diethoxy-phenyl)-pent-2-en-4-ynyloxy]-phenyl}-2-ethoxy-propionic acid,
(Z)-(S)-3-{4-[5-(1,3-Bis-(2,2,2-trifluoromethoxy)-phenyl)-pent-2-en-4-ynyloxy]-phenyl}-2-ethoxy-propionic acid,
(Z)-(S)-3-{4-[5-(1,3-Bis-(2,2,2-trifluoroethoxy)-phenyl)-pent-2-en-4-ynyloxy]-phenyl}-2-ethoxy-propionic acid,
(Z)-(S)-3-{4-[5-(3,5-Difluoro-phenyl)-pent-2-en-4-ynyloxy]-phenyl}-2-ethoxy-propionic acid,
(Z)-(S)-3-{4-[5-(3,5-Dibromo-phenyl)-pent-2-en-4-ynyloxy]-phenyl}-2-ethoxy-propionic acid,
(Z)-(S)-3-{4-[5-(3,5-Diiodo-phenyl)-pent-2-en-4-ynyloxy]-phenyl}-2-ethoxy-propionic acid,
(Z)-(S)-3-{4-[5-(3,5-Bis-trifluoromethyl-phenyl)-pent-2-en-4-ynyloxy]-phenyl}-2-ethoxy-propionic acid,
(Z)-(S)-3-{4-[5-(3,5-Dimethoxy-phenyl)-pent-2-en-4-ynyloxy]-phenyl}-2-ethoxy-propionic acid,
(Z)-(S)-3-{4-[5-(3,5-Diethoxy-phenyl)-pent-2-en-4-ynyloxy]-phenyl}-2-ethoxy-propionic acid,
(Z)-(S)-3-{4-[5-(3,5-Bis-(2,2,2-trifluoromethoxy)-phenyl)-pent-2-en-4-ynyloxy]-phenyl}-2-ethoxy-propionic acid,
(Z)-(S)-3-{4-[5-(3,5-Bis-(2,2,2-trifluoroethoxy)-phenyl)-pent-2-en-4-ynyloxy]-phenyl}-2-ethoxy-propionic acid,
(Z)-(S)-3-{4-[5-(1,3-Difluoro-phenyl)-3-methyl-pent-2-en-4-ynyloxy]-phenyl}-2-ethoxy-propionic acid,
(Z)-(S)-3-{4-[5-(1,3-Dibromo-phenyl)-3-methyl-pent-2-en-4-ynyloxy]-phenyl}-2-ethoxy-propionic acid,
(Z)-(S)-3-{4-[5-(1,3-Diiodo-phenyl)-3-methyl-pent-2-en-4-ynyloxy]-phenyl}-2-ethoxy-propionic acid,
(Z)-(S)-3-{4-[5-(1,3-Bis-trifluoromethyl-phenyl)-3-methyl-pent-2-en-4-ynyloxy]-phenyl}-2-ethoxy-propionic acid,
(Z)-(S)-3-{4-[5-(1,3-Dimethoxy-phenyl)-pent-2-en-4-ynyloxy]-phenyl}-3-methyl-2-ethoxy-propionic acid,
(Z)-(S)-3-{4-[5-(1,3-Diethoxy-phenyl)-3-methyl-pent-2-en-4-ynyloxy]-phenyl}-2-ethoxy-propionic acid,
(Z)-(S)-3-{4-[5-(1,3-Bis-(2,2,2-trifluoromethoxy)-phenyl)-3-methyl pent-2-en-4-ynyloxy]-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-phenyl}-2-ethoxy-propionic acid,
(Z)-(S)-3-{4-[5-(3,5-Difluoro-phenyl)-3-methyl-pent-2-en-4-ynyloxy]-phenyl}-2-ethoxy-propionic acid,
(Z)-(S)-3-{4-[5-(3,5-Dibromo-phenyl)-3-methyl-pent-2-en-4-ynyloxy]-phenyl}-2-ethoxy-propionic acid,
(Z)-(S)-3-{4-[5-(3,5-Diiodo-phenyl)-3-methyl-pent-2-en-4-ynyloxy]-phenyl}-2-ethoxy-propionic acid,
(Z)-(S)-3-{4-[5-(3,5-Bis-trifluoromethyl-phenyl)-3-methyl-pent-2-en-4-ynyloxy]-phenyl}-2-ethoxy-propionic acid,
(Z)-(S)-3-{4-[5-(3,5-Dimethoxy-phenyl)-3-methyl-pent-2-en-4-ynyloxy]-phenyl}-2-ethoxy-propionic acid,
(Z)-(S)-3-{4-[5-(3,5-Diethoxy-phenyl)-3-methyl-pent-2-en-4-ynyloxy]-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-phenyl}-2-ethoxy-propionic acid,
(Z)-(S)-3-{4-[5-(1,3-Difluoro-phenyl)-pent-2-en-4-ynyloxy]-3-chloro-phenyl}-2-ethoxy-propionic acid,
(Z)-(S)-3-{4-[5-(1,3-Dibromo-phenyl)-pent-2-en-4-ynyloxy]-3-chloro-phenyl}-2-ethoxy-propionic acid,
(Z)-(S)-3-{4-[5-(1,3-Diiodo-phenyl)-pent-2-en-4-ynyloxy]-3-chloro-phenyl}-2-ethoxy-propionic acid,
(Z)-(S)-3-{4-[5-(1,3-Bis-trifluoromethyl-phenyl)-pent-2-en-4-ynyloxy]-3-chloro-phenyl}-2-ethoxy-propionic acid,
(Z)-(S)-3-{4-[5-(1,3-Dimethoxy-phenyl)-pent-2-en-4-ynyloxy]-3-chloro-phenyl}-2-ethoxy-propionic acid,
(Z)-(S)-3-{4-[5-(1,3-Diethoxy-phenyl)-pent-2-en-4-ynyloxy]-3-chloro-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-chloro-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-chloro-phenyl}-2-ethoxy-propionic acid,
(Z)-(S)-3-{4-[5-(3,5-Difluoro-phenyl)-pent-2-en-4-ynyloxy]-3-chloro-phenyl}-2-ethoxy-propionic acid,
(Z)-(S)-3-{4-[5-(3,5-Dibromo-phenyl)-pent-2-en-4-ynyloxy]-3-chloro-phenyl}-2-ethoxy-propionic acid,
(Z)-(S)-3-{4-[5-(3,5-Diiodo-phenyl)-pent-2-en-4-ynyloxy]-3-chloro-phenyl}-2-ethoxy-propionic acid,
(Z)-(S)-3-{4-[5-(3,5-Bis-trifluoromethyl-phenyl)-pent-2-en-4-ynyloxy]-3-chloro-phenyl}-2-ethoxy-propionic acid,
(Z)-(S)-3-{4-[5-(3,5-Dimethoxy-phenyl)-pent-2-en-4-ynyloxy]-3-chloro-phenyl}-2-ethoxy-propionic acid,
(Z)-(S)-3-{4-[5-(3,5-Diethoxy-phenyl)-pent-2-en-4-ynyloxy]-3-chloro-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-chloro-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-chloro-phenyl}-2-ethoxy-propionic acid,
(Z)-(S)-3-{4-[5-(1,3-Difluoro-phenyl)-3-methyl-pent-2-en-4-ynyloxy]-3-chloro-phenyl}-2-ethoxy-propionic acid,
(Z)-(S)-3-{4-[5-(1,3-Dibromo-phenyl)-3-methyl-pent-2-en-4-ynyloxy]-3-chloro-phenyl}-2-ethoxy-propionic acid,
(Z)-(S)-3-{4-[5-(1,3-Diiodo-phenyl)-3-methyl-pent-2-en-4-ynyloxy]-3-chloro-phenyl}-2-ethoxy-propionic acid,
(Z)-(S)-3-{4-[5-(1,3-Bis-trifluoromethyl-phenyl)-3-methyl-pent-2-en-4-ynyloxy]-3-chloro-phenyl}-2-ethoxy-propionic acid,
(Z)-(S)-3-{4-[5-(1,3-Dimethoxy-phenyl)-pent-2-en-4-ynyloxy]-3-chloro-phenyl}-3-methyl-2-ethoxy-propionic acid, (Z)-(S)-3-{4-[5-(1,3-Diethoxy-phenyl)-3-methyl-pent-2-en-4-ynyloxy]-3-chloro-phenyl}-2-ethoxy-propionic acid,
(Z)-(S)-3-{4-[5-(1,3-Bis-(2,2,2-trifluoromethoxy)-phenyl)-3-methyl-pent-2-en-4-ynyloxy]-3-chloro-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-chloro-phenyl}-2-ethoxy-propionic acid,
(Z)-(S)-3-{4-[5-(3,5-Difluoro-phenyl)-3-methyl-pent-2-en-4-ynyloxy]-3-chloro-phenyl}-2-ethoxy-propionic acid,
(Z)-(S)-3-{4-[5-(3,5-Dibromo-phenyl)-3-methyl-pent-2-en-4-ynyloxy]-3-chloro-phenyl}-2-ethoxy-propionic acid,
(Z)-(S)-3-{4-[5-(3,5-Diiodo-phenyl)-3-methyl-pent-2-en-4-ynyloxy]-3-chloro-phenyl}-2-ethoxy-propionic acid,
(Z)-(S)-3-{4-[5-(3,5-Bis-trifluoromethyl-phenyl)-3-methyl-pent-2-en-4-ynyloxy]-3-chloro-phenyl}-2-ethoxy-propionic acid,
(Z)-(S)-3-{4-[5-(3,5-Dimethoxy-phenyl)-3-methyl-pent-2-en-4-ynyloxy]-3-chloro-phenyl}-2-ethoxy-propionic acid,
(Z)-(S)-3-{4-[5-(3,5-Diethoxy-phenyl)-3-methyl-pent-2-en-4-ynyloxy]-3-chloro-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-3-chloro-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-3-chloro-phenyl}-2-ethoxy-propionic acid,
(Z)-(S)-3-{4-[5-(1,3-Difluoro-phenyl)-pent-2-en-4-ynyloxy]-3-bromo-phenyl}-2-ethoxy-propionic acid,
(Z)-(S)-3-{4-[5-(1,3-Dibromo-phenyl)-pent-2-en-4-ynyloxy]-3-bromo-phenyl}-2-ethoxy-propionic acid,
(Z)-(S)-3-{4-[5-(1,3-Diiodo-phenyl)-pent-2-en-4-ynyloxy]-3-bromo-phenyl}-2-ethoxy-propionic acid,
(Z)-(S)-3-{4-[5-(1,3-Bis-trifluoromethyl-phenyl)-pent-2-en-4-ynyloxy]-3-bromo-phenyl}-2-ethoxy-propionic acid,
(Z)-(S)-3-{4-[5-(1,3-Dimethoxy-phenyl)-pent-2-en-4-ynyloxy]-3-bromo-phenyl}-2-ethoxy-propionic acid,
(Z)-(S)-3-{4-[5-(1,3-Diethoxy-phenyl)-pent-2-en-4-ynyloxy]-3-bromo-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-bromo-phenyl}-2-ethoxy-propionic acid,
(Z)-(S)-3-{4-[5-(1,3-Bis-(2,2,2-trifluoroethoxy)-phenyl)-pent-2-en-4-ynyloxy]-3-bromo-phenyl}-2-ethoxy-propionic acid,
(Z)-(S)-3-{4-[5-(3,5-Difluoro-phenyl)-pent-2-en-4-ynyloxy]-3-bromo-phenyl}-2-ethoxy-propionic acid,
(Z)-(S)-3-{4-[5-(3,5-Dibromo-phenyl)-pent-2-en-4-ynyloxy]-3-bromo-phenyl}-2-ethoxy-propionic acid,
(Z)-(S)-3-{4-[5-(3,5-Diiodo-phenyl)-pent-2-en-4-ynyloxy]-3-bromo-phenyl}-2-ethoxy-propionic acid,
(Z)-(S)-3-{4-[5-(3,5-Bis-trifluoromethyl-phenyl)-pent-2-en-4-ynyloxy]-3-bromo-phenyl}-2-ethoxy-propionic acid,
(Z)-(S)-3-{4-[5-(3,5-Dimethoxy-phenyl)-pent-2-en-4-ynyloxy]-3-bromo-phenyl}-2-ethoxy-propionic acid,
(Z)-(S)-3-{4-[5-(3,5-Diethoxy-phenyl)-pent-2-en-4-ynyloxy]-3-bromo-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-bromo-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-bromo-phenyl}-2-ethoxy-propionic acid,
(Z)-(S)-3-{4-[5-(1,3-Difluoro-phenyl)-3-methyl-pent-2-en-4-ynyloxy]-3-bromo-phenyl}-2-ethoxy-propionic acid,
(Z)-(S)-3-{4-[5-(1,3-Dibromo-phenyl)-3-methyl-pent-2-en-4-ynyloxy]-3-bromo-phenyl}-2-ethoxy-propionic acid,
(Z)-(S)-3-{4-[5-(1,3-Diiodo-phenyl)-3-methyl-pent-2-en-4-ynyloxy]-3-bromo-phenyl}-2-ethoxy-propionic acid,
(Z)-(S)-3-{4-[5-(1,3-Bis-trifluoromethyl-phenyl)-3-methyl-pent-2-en-4-ynyloxy]-3-bromo-phenyl}-2-ethoxy-propionic acid,
(Z)-(S)-3-{4-[5-(1,3-Dimethoxy-phenyl)-pent-2-en-4-ynyloxy]-3-bromo-phenyl}-3-methyl-2-ethoxy-propionic acid,
(Z)-(S)-3-{4-[5-(1,3-Diethoxy-phenyl)-3-methyl-pent-2-en-4-ynyloxy]-3-bromo-phenyl}-2-ethoxy-propionic acid,
(Z)-(S)-3-{4-[5-(1,3-Bis-(2,2,2-trifluoromethoxy)-phenyl)-3-methyl-pent-2-en-4-ynyloxy]-3-bromo-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-bromo-phenyl}-2-ethoxy-propionic acid,
(Z)-(S)-3-{4-[5-(3,5-Difluoro-phenyl)-3-methyl-pent-2-en-4-ynyloxy]-3-bromo-phenyl}-2-ethoxy-propionic acid,
(Z)-(S)-3-{4-[5-(3,5-Dibromo-phenyl)-3-methyl-pent-2-en-4-ynyloxy]-3-bromo-phenyl}-2-ethoxy-propionic acid,
(Z)-(S)-3-{4-[5-(3,5-Diiodo-phenyl)-3-methyl-pent-2-en-4-ynyloxy]-3-bromo-phenyl}-2-ethoxy-propionic acid,
(Z)-(S)-3-{4-[5-(3,5-Bis-trifluoromethyl-phenyl)-3-methyl-pent-2-en-4-ynyloxy]-3-bromo-phenyl}-2-ethoxy-propionic acid,
(Z)-(S)-3-{4-[5-(3,5-Dimethoxy-phenyl)-3-methyl-pent-2-en-4-ynyloxy]-3-bromo-phenyl}-2-ethoxy-propionic acid,
(Z)-(S)-3-{4-[5-(3,5-Diethoxy-phenyl)-3-methyl-pent-2-en-4-ynyloxy]-3-bromo-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-3-bromo-phenyl}-2-ethoxy-propionic acid,
(Z)-(S)-3-{4-[5-(3,5-Bis-(2,2,2-trifluoroethoxy)-phenyl)-3-methyl-pent-2-en-4-ynyloxy]-3-bromo-phenyl}-2-ethoxy-propionic acid,
(Z)-(S)-3-{4-[5-(1,3-Difluoro-phenyl)-pent-2-en-4-ynyloxy]-3-iodo-phenyl}-2-ethoxy-propionic acid,
(Z)-(S)-3-{4-[5-(1,3-Dibromo-phenyl)-pent-2-en-4-ynyloxy]-3-iodo-phenyl}-2-ethoxy-propionic acid,
(Z)-(S)-3-{4-[5-(1,3-Diiodo-phenyl)-pent-2-en-4-ynyloxy]-3-iodo-phenyl}-2-ethoxy-propionic acid,
(Z)-(S)-3-{4-[5-(1,3-Bis-trifluoromethyl-phenyl)-pent-2-en-4-ynyloxy]-3-iodo-phenyl}-2-ethoxy-propionic acid,
(Z)-(S)-3-{4-[5-(1,3-Dimethoxy-phenyl)-pent-2-en-4-ynyloxy]-3-iodo-phenyl}-2-ethoxy-propionic acid,
(Z)-(S)-3-{4-[5-(1,3-Diethoxy-phenyl)-pent-2-en-4-ynyloxy]-3-iodo-phenyl}-2-ethoxy-propionic acid,
(Z)-(S)-3-{4-[5-(1,3-Bis-(2,2,2-trifluoromethoxy)-phenyl)-pent-2-en-4-ynyloxy]-3-iodo-phenyl}-2-ethoxy-propionic acid, (Z)-(S)-3-{4-[5-(1,3-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(3,5-Difluoro-phenyl)-pent-2-en-4-ynyloxy]-3-iodo-phenyl}-2-ethoxy-propionic acid,
(Z)-(S)-3-{4-[5-(3,5-Dibromo-phenyl)-pent-2-en-4-ynyloxy]-3-iodo-phenyl}-2-ethoxy-propionic acid,
(Z)-(S)-3-{(4-[5-(3,5-Diiodo-phenyl)-pent-2-en-4-ynyloxy]-3-iodo-phenyl}-2-ethoxy-propionic acid,
(Z)-(S)-3-{4-[5-(3,5-Bis-trifluoromethyl-phenyl)-pent-2-en-4-ynyloxy]-3-iodo-phenyl}-2-ethoxy-propionic acid,
(Z)-(S)-3-{4-[5-(3,5-Dimethoxy-phenyl)-pent-2-en-4-ynyloxy]-3-iodo-phenyl}-2-ethoxy-propionic acid,
(Z)-(S)-3-{4-[5-(3,5-Diethoxy-phenyl)-pent-2-en-4-ynyloxy]-3-iodo-phenyl}-2-ethoxy-propionic acid,
(Z)-(S)-3-{4-[5-(3,5-Bis-(2,2,2-trifluoromethoxy)-phenyl)-pent-2-en-4-ynyloxy]-3-iodo-phenyl}-2-ethoxy-propionic acid,
(Z)-(S)-3-{4-[5-(3,5-Bis-(2,2,2-trifluoroethoxy)-phenyl)-pent-2-en-4-ynyloxy]-3-iodo-phenyl}-2-ethoxy-propionic acid,
(Z)-(S)-3-{4-[5-(1,3-Difluoro-phenyl)-3-methyl-pent-2-en-4-ynyloxy]-3-iodo-phenyl}-2-ethoxy-propionic acid,
(Z)-(S)-3-{4-[5-(1,3-Dibromo-phenyl)-3-methyl-pent-2-en-4-ynyloxy]-3-iodo-phenyl}-2-ethoxy-propionic acid,
(Z)-(S)-3-{4-[5-(1,3-Diiodo-phenyl)-3-methyl-pent-2-en-4-ynyloxy]-3-iodo-phenyl}-2-ethoxy-propionic acid,
(Z)-(S)-3-{4-[5-(1,3-Bis-trifluoromethyl-phenyl)-3-methyl-pent-2-en-4-ynyloxy]-3-iodo-phenyl}-2-ethoxy-propionic acid,
(Z)-(S)-3-{4-[5-(1,3-Dimethoxy-phenyl)-pent-2-en-4-ynyloxy]-3-iodo-phenyl}-3-methyl-2-ethoxy-propionic acid,
(Z)-(S)-3-{4-[5-(1,3-Diethoxy-phenyl)-3-methyl-pent-2-en-4-ynyloxy]-3-iodo-phenyl}-2-ethoxy-propionic acid,
(Z)-(S)-3-{4-[5-(1,3-Bis-(2,2,2-trifluoromethoxy)-phenyl)-3-methyl-pent-2-en-4-ynyloxy]-3-iodo-phenyl}-2-ethoxy-propionic acid,
(Z)-(S)-3-{4-[5-(1,3-Bis-(2,2,2-trifluoroethoxy)-phenyl)-3-methyl-pent-2-en-4-ynyloxy]-3-iodo-phenyl}-2-ethoxy-propionic acid,
(Z)-(S)-3-{4-[5-(3,5-Difluoro-phenyl)-3-methyl-pent-2-en-4-ynyloxy]-3-iodo-phenyl}-2-ethoxy-propionic acid,
(Z)-(S)-3-{4-[5-(3,5-Dibromo-phenyl)-3-methyl-pent-2-en-4-ynyloxy]-3-iodo-phenyl}-2-ethoxy-propionic acid,
(Z)-(S)-3-{4-[5-(3,5-Diiodo-phenyl)-3-methyl-pent-2-en-4-ynyloxy]-3-iodo-phenyl}-2-ethoxy-propionic acid,
(Z)-(S)-3-{4-[5-(3,5-Bis-trifluoromethyl-phenyl)-3-methyl-pent-2-en-4-ynyloxy]-3-iodo-phenyl}-2-ethoxy-propionic acid,
(Z)-(S)-3-{4-[5-(3,5-Dimethoxy-phenyl)-3-methyl-pent-2-en-4-ynyloxy]-3-iodo-phenyl}-2-ethoxy-propionic acid,
(Z)-(S)-3-{4-[5-(3,5-Diethoxy-phenyl)-3-methyl-pent-2-en-4-ynyloxy]-3-iodo-phenyl}-2-ethoxy-propionic acid,
(Z)-(S)-3-{4-[5-(3,5-Bis-(2,2,2-trifluoromethoxy)-phenyl)-3-methyl-pent-2-en-4-ynyloxy]-3-iodo-phenyl}-2-ethoxy-propionic acid, and
(Z)-(S)-3-{4-[5-(3,5-Bis-(2,2,2-trifluoroethoxy)-phenyl)-3-methyl-pent-2-en-4-ynyloxy]-3-iodo-phenyl}-2-ethoxy-propionic acid;

or a pharmaceutically acceptable salt thereof.

50. The pharmaceutical composition according to claim 1 wherein the GLP-1 derivative comprises a sequence wherein at least one amino acid residue of the sequence has a lipophilic substituent attached, with the proviso that if only one lipophilic substituent is present and this substituent is attached to the N-terminal or to the C-terminal amino acid residue of the parent peptide then this substituent is an alkyl group or a group which has an ω-carboxylic acid group.

51. The pharmaceutical composition according to claim 50 wherein the GLP-1 derivative comprises a peptide selected from the group GLP-1(1-35); GLP-1(1-36); GLP-1(1-36)amide; GLP-1(1-37); GLP-1(1-38); GLP-1(1-39); GLP-1(1-40); GLP-1(1-41).

52. The pharmaceutical composition according to claim 50 wherein the GLP-1 derivative comprises a peptide selected from the group GLP-1(7-35); GLP-1(7-36); GLP-1(7-36)amide; GLP-1(7-37); GLP-1(7-38); GLP-1(7-39); GLP-1(740) and GLP-1(7-41).

53. The pharmaceutical composition according to claim 50 wherein the GLP-1 derivative comprises a peptide selected from the group: $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26,34}Lys^{38}$GLP-1(7–38); $Arg^{26,34}Lys^{39}$-GLP-1(7–39); $Arg^{26,34}Lys^{40}$-GLP-1(7-40); $Arg^{26}Lys^{36}$-GLP-1(7-37); $Arg^{34}Lys^{36}$-GLP-1(7-37); $Arg^{26}Lys^{39}$-GLP-1(7-39); $Arg^{34}Lys^{40}$-GLP-1(7-40); $Arg^{26,34}Lys^{36,39}$-GLP-1(7-39); $Arg^{26,34}Lys^{3640}$-GLP-1(7-40); $Gly^8Arg26$-GLP-1(7-37); $Gly^8Arg^{34}$-GLP-1(7-37); $Gly^8Lys^{36}$-GLP-1(7-37); $Gly^8Arg^{26,34}Lys^{36}$-GLP-1(7-37); $Gly^8Arg^{26,34}Lys^{39}$-GLP-1(7-39); $Gly^8Arg^{26,34}Lys^{40}$-GLP-1(7-40); $Gly^8Arg^{26}Lys^{36}$-GLP-1(7-37); $Gly^8Arg^{34}Lys^{36}$-GLP-1(7-37); $Gly^8Arg^{26}Lys^9$-GLP-1(7-39); $Gly^8Arg^{34}Lys^{40}$-GLP-1(7-40); $Gly^8Arg^{26,34}Lys^{36,39}$-GLP-1(7-39) and $Gly^8Arg^{26,34}Lys^{36,40}$-GLP-1(7-40).

54. The pharmaceutical composition according to claim 53 wherein the GLP-1 derivative is $Arg^{34}$-GLP-1(7-37), wherein
 (a) the ε-amino group of Lys at position 26 is substituted with a lipophilic substituent optionally via a spacer, and
 (b) the lipophilic substituent is (i) $CH_3(CH_2)_nCO$— wherein n is 6, 8, 10,12, 14, 16, 18, 20 or 22, (ii) $HOOC(CH_2)_mCO$— wherein m is 10, 12, 14, 16, 18, 20 or 22, or (iii) lithocholyl, and
 when present, the spacer is an amino acid residue except Cys, or the spacer is γ-aminobutanoyl.

55. The pharmaceutical composition of claim 54, wherein the lipophilic substituent is linked to the ε-amino group of Lys via a spacer.

56. The pharmaceutical composition of claim 55, wherein the spacer is selected from the group: γ-glutamyl, β-aspar-agyl, glycyl, and β-alanyl.

57. The pharmaceutical composition according to claim 54 wherein the GLP-1 derivative is selected from the following:
 $Lys^{26}$ (N$^ε$-tetradecanoyl)-GLP-1(7-37),
 $Arg^{34}Lys^{26}$(N$^ε$-lithocholyl)-GLP-1(7-37)-OH,
 $Arg^{34}Lys^{26}$(N$^ε$-(γ-glutamyl(N$^α$-hexadecanoyl)))-GLP-1(7-37)-OH, and
 $Arg^{34}Lys^{26}$(N$^ε$-(γ-glutamyl(N$^α$-tetradecanoyl)))-GLP-1(7-37)-OH.

58. A pharmaceutical composition comprising the composition of claim 1 together with a pharmaceutically acceptable carrier or diluent.

59. A pharmaceutical composition comprising the pharmaceutical composition of claim 50 together with a pharmaceutically acceptable carrier or diluent.

60. A pharmaceutical composition according to claim 59 in unit dosage form, comprising from about 0.05 to about 100 mg of the compound of formula (I) or a pharmaceutically acceptable salt thereof.

61. A pharmaceutical composition according to claim 59 for oral, nasal, transdermal, pulmonal, or parenteral administration.

62. A pharmaceutical composition according to claim 60 in unit dosage form, comprising from about 0.1 mg to about 50 mg of the compound of formula (I) or a pharmacetically acceptable salt thereof.

* * * * *